US005807670A

United States Patent [19]
Muerhoff et al.

[11] Patent Number: 5,807,670
[45] Date of Patent: *Sep. 15, 1998

[54] DETECTION OF HEPATITIS GB VIRUS GENOTYPES

[75] Inventors: Anthony Scott Muerhoff, Kenosha, Wis.; John N. Simons, Grayslake, Ill.; Thomas P. Leary, Kenosha, Wis.; Larry Birkenmeyer, Chicago, Ill.; James C. Erker, Hainesville, Ill.; Michelle Chalmers, Lake Villa, Ill.; George J. Dawson; Suresh M. Desai, both of Libertyville, Ill.; Isa K. Mushahwar, Grayslake, Ill.

[73] Assignee: Abbott Laboratories, Abbott Park, Ill.

[*] Notice: The term of this patent shall not extend beyond the expiration date of Pat. No. 5,709,997.

[21] Appl. No.: 580,038

[22] Filed: Dec. 21, 1995

Related U.S. Application Data

[60] Provisional application No. 60/002,625 Aug. 22, 1995.
[51] Int. Cl.⁶ ..................................................... C12Q 1/70
[52] U.S. Cl. .......................... 435/5; 536/23.72; 536/24.32
[58] Field of Search ................. 435/5, 320.1; 536/23.72, 536/24.32, 24.33

[56] References Cited

U.S. PATENT DOCUMENTS

| | | |
|---|---|---|
| 4,743,535 | 5/1988 | Carrico . |
| 4,876,187 | 10/1989 | Duck et al. . |
| 5,275,947 | 1/1994 | Arima et al. ........................ 435/252.33 |
| 5,399,346 | 3/1995 | Anderson et al. .................... 424/93.21 |
| 5,527,669 | 6/1996 | Resnick et al. .............................. 435/5 |
| 5,576,302 | 11/1996 | Cook et al. ................................. 514/44 |
| 8,246,985 | 5/1994 | Kim et al. . |
| 8,285,558 | 8/1994 | Kim et al. . |
| 8,329,729 | 10/1994 | Kim et al. . |
| 8,344,271 | 11/1994 | Fry et al. . |
| 8,357,509 | 12/1994 | Kim et al. . |
| 8,389,886 | 1/1995 | Kim et al. . |

FOREIGN PATENT DOCUMENTS

| | | |
|---|---|---|
| 0318216 | 5/1989 | European Pat. Off. . |
| 9000597 | 1/1990 | WIPO . |
| 9408002 | 4/1994 | WIPO . |
| 9418217 | 8/1994 | WIPO . |
| 9532290 | 11/1995 | WIPO . |
| 9532291 | 11/1995 | WIPO . |
| 9532292 | 11/1995 | WIPO . |
| 9506266 | 5/1996 | WIPO . |

OTHER PUBLICATIONS

S. Chan et al., Journal of General Virology, 73:1131–1141 (1992).
A. Muerhoff et al., *Journal of Virology* 69 (9), 5621–5630 (1995).
Gura, *Science* vol. 270 pp. 575–577 (1995).
Brown, *Washington Post* pp. 1 & A22 (Dec. 8, 1995).
Choo et al., *Proc. Natl. Acad. Sci. USA,* vol. 88, pp. 2451–2455 (1991).
Okamoto et al., "Polyprotein precursor—hepatitis C virus", EMBL Sequence Accession No. S40770, Submitted Mar. 1992.
Okamoto et al., Virology, vol. 188, pp. 331–341 (1992).
A. Takamizawa et al., *Journal of Virology,* vol. 65, No. 3, pp. 1105–1113 (1991).
S. K. Kuwada et al., *The American Journal of Gastroenterology,* vol. 89, No. 1, pp. 57–61 (1994).
A. S. Muerhoff et al., *Journal of Virological Methods,* vol. 62, No. 1, pp. 55–62 (1996).
P. Tijssen, "Practice and Theory of Enzyme Immunoassays" Elsevier, Amsterdam, pp. 333–340 (1985).
S. Vijayasarathy, *Nucleic Acids Research,* vol. 18, No. 10, pp. 296–2975 (1990).
T. Peters et al., *Frequency of Hepatitis C in Acute Post–Transfusion Hepatitis After Open–Heart Surgery: A Prospective Study in 1,476 Patients, Journal of Medical Virology* vol. 39:139–145 (1993).
R. Purcell, *The Discovery of the Hepatitis Viruses, Gastroenterology* vol. 104 No. 4:955–963 (1993).
G. Dawson et al., *Solid–phase enzyme–linked immunosobent assay for hepatitis E virus IgG and IgM antibodies utilizing recombinant antigens and synthetic peptides, Journal of Virological Methods* vol. 38:175–186 (1992).
P. Yarbough et al., Hepatitis E Virus: Identification of Type–Common Epitopes, *Journal of Virology* vol. 65 No. 11:p. 5790–5797 (1991).
H. Alter et al., Detection of Antibody to Hepatitis C Virus in Prospectively Followed Transfusion Recipients with Acute and Chronic Non–A, Non–B Hepatitis, *The New England Journal of Medicine* vol. 321 No. 22:p 1494–1500 (1989).
M. Alter et al., Risk Factors for Acute Non–A, Non–B Hepatitis in the United States an Association with Hepatitis C Virus Infection, *JAMA* vol. 264 No. 17:p. 2231–2235 (1990).
J. Dienstag, Hepatitis Non–A, Non–B:C at last, *Gastrointerology* vol. 99 No. 4:pp. 1177–1180 (1990).
G. Reyes et al., Isolation of a cDNA from the Virus Responsible for Enterically Transmitted Non–A, Non–B Hepatitis, *Science* vol. 247:pp.1335–1339 (1990)
G. Kuo et al., An Assay for Circulating Antibodies to a Major Etiologic Virus of Human Non–A, Non–B Hepatitis, *Science* vol. 244:pp. 362–364 (1989).
A. Weiner et al., Detection of hepatitis C viral sequences in non–A, non–B hepatitis, *The Lancet* vol. 335:pp. 1–3 (1990).
G. Schlauder et al., Viraemia in Egyptian children with hepatitis E virus infection, *The Lancet* vol. 341:pp. 378 (1993).
N. Lisitsyn et al., Cloning the Differences Between Two Complex Genomes, *Science* vol. 259:pp. 946–951 (1993).

(List continued on next page.)

Primary Examiner—Scott W. Houtteman
Attorney, Agent, or Firm—Priscilla E. Porembski; Dianne Casuto

[57] ABSTRACT

HGBV-C oligonucleotides from the 5' end of HGBV-C useful for the detection and genotyping of HGBV-C isolates. Also provided are assays which utilize these oligonucleotides.

23 Claims, 13 Drawing Sheets

OTHER PUBLICATIONS

V. Thiers et al., Post–transfusional anti–HCV–negative non–A and non–B hepatitis (II) serological and polymerase chain reaction analysis for hepatitis C and hepatitis B viruses, *Journal of Hepatology* vol. 18:pp.34–39 (1993).

Hepatitis C virus upstanding, *The Lancet* vol. 335:pp. 1431–1432 (1990).

W. Parks et al., Attempted Isolation of Hepatitis Viruses in Marmosets, *The Journal of Infectious Diseases* vol. 120 No. 5:539–547 (1969).

A. Holmes et al., Specific Neutralization of Human Hepatitis Type A in Marmoset Monkeys, *Nature* vol. 243:pp. 419–420 (1973).

P. Provost et al., Physical, Chemical and Morphologic Dimensions of Human Hepatitis A Virus Strain CR326 (38578), *Proceeding of the Society for Experimental Biology and Medicine* vol. 148:pp. 532–539 (1975).

Q. Choo et al., Isolation of a cDNA Clone Derived from a Blood–Borne Non–A, Non–B Viral Hepatitis Genome, *Science* vol. 244:pp. 359–361 (1989).

J. Almeida et al., Morphology of the GB hepatitis agent, *Nature* vol. 261:pp. 608–609(1976).

F. Deinhart et al., Studies on the Transmission of Human Viral Hepatitis to Marmoset Monkeys, *Journal of Experimental Medicine* vol. 125:pp. 673–688, Plate 81–86 (1966).

J. Dienstag, Non–A, Non–B Hepatitis. II. Experimental Transmission, Putative Virus Agents and Markers, and Prevention, *Gastroenterology* vol. 85 No. 3:pp. 743–768 (1983).

F. Hollinger et al., Transfusion–Transmitted Viruses Study: Experimental Evidence for Two Non–A Non–B Hepatitis Agents, *Journal of Infectious Diseases* vol. 142 No. 3:pp. 400–407 (1980).

D. Bradley, Transmission, Etiology, and Pathogenesis of Viral Hepatitis Non–A, Non–B in Non–Human Primates, *Advances in Hepatitis Research*: pp. 268–280 (1984).

F. Deinhardt et al., Hepatitis in marmosets, *The American Journal of the Medical Sciences* vol. 270:pp. 73–80 (1975).

S. Kalter, Comparison of Infectivity of Human Non–A/Non–B Hepatitis and the GB Hepatitis Agent in Marmosets, *Viral and Immunological Diseases in Nonhuman Primates*;:pp. 221–224 (1983).

E. Tabor et al., Transmission of Human Non–A, Non–B Hepatitis to Chimpanzees Following Failure to Transmit GB Agent Hepatitis, *Journal of Medical Virology*:pp. 103–108 (1980).

D. Bradley et al., Posttransfusion Non–A, Non–B Hepatitis: Physicochemical Properties of Two Distinct Agents, *The Journal of Infectious Diseases* vol. 148 No. 2:pp. 254–265 (1983).

J. Dienstag, Virus–like particles and GB agent hepatitis, *Nature* vol. 264:pp. 260–261 (1976).

P. Karayiannis et al. Studies of GB Hepatitis Agent in Tamarins, *Hepatology* vol. 9 No. 2:pp. 186–192 (1989).

J. Melnick, Classification of Hepatitis A Virus as Enterovirus Type 72 and of Hepatitis B Virus as Hepadnavirus Type 1, *Intervirology* vol. 18:pp. 105–106 (1982).

W. Parks et al., Characterization of Marmoset Hepatitis virus, *The Journal of Infectious Diseases* vol. 120 No. 5:pp. 548–559 (1969).

S. Feinstone et al., Hepatitis A: Detection by Immune electron Microscopy of a Viruslike Antigen Associated with Acute Illness, *Science* Vol. 182:pp. 1026–1028 (1973).

E. Tabor et al., Lack of Susceptibility of Marmosets to human Non–A, Non–B Hepatitis, *The Journal of Infectious Diseases* vol. 140 No. 5:pp. 794–797 (1979).

E. Fagan et al., Toga Virus–Like Particles in Acute Liver Failure Attributed to Sporadic Non–A, Non–B Hepatitis and Recurrence After Liver Transplantation, *Journal of Medical Virology* vol. 38:pp. 71–77 (1992).

J. Dienstag, Virus particles in marmoset hepatitis, *Nature* Vol. 267:pp. 729–730. (1977).

F.Deinhardt et al., Hepatitis in Marmosets, *The Journal of Infectious Diseases* vol. 121 No. 3:pp. 351–354 (1970).

F Deinhardt et al., The Mythology of Various Hepatitis A Virus Isolates, *International Symposium on Viral Hepatitis*:pp. 390–404 (1975).

M. Alter et al., The Natural History of Community–Acquired Hepatitis C in the United States, *The New England Journal of Medicine* vol. 327 No. 27:pp. 1899–1905 (1992).

R. Gibbs, Polymerase chain reaction techniques, *Analytical Biotechnology*:pp. 69–75 (1991).

S. Friedman et al., The core element of the EcoRII methylase as defined by protease digestion and deletion analysis, *Nucleic Acids Research* vol. 19 No. 19:pp. 5403–5408 (1991).

A. Rosenthal et al., Genomic walking and sequencing by oligo–cassette mediated polymerase chain reaction, *Nucleic Acids Research* vol. 18 No. 10:pp.3095–3096 (1990).

A. Akowitz, Protected endogenous retroviral sequences copurify with infectivity in experimental Creutzfeldt–Jakob disease, *Archives of Virology* vol. 130:pp.301–316 (1993).

Non–A, Non–B?, *The Lancet* vol. 2:pp. 64–65 (1975).

F. Hollinger, Non–A, Non–B Hepatitis Viruses, *Virology*:pp.2239–2273 (1990).

J. Dienstag, Non–A, Non–B Hepatitis I. Recognition, Epidemiology, and Clinical Features, *Gastroenterology* vol. 85 No. 2:pp. 439–462 (1983).

J. Strauss et al., Structure and Function of the Flavivirus and Pestivirus Genomes, *Viral Hepatitis and Liver Disease*:pp. 333–344 (1990).

H. Alter et al., Posttransfusion Hepatitis After Exclusion of Commercial and Hepatitis–B Antigen–Positive Donors, *Annals of Internal Medicine* vol. 77 No. 5:pp. 691–699 (1972).

H. Alter et al., Clinical and Serological Analysis of Transfusion–Associated Hepatitis, *The Lancet*:pp. 838–841 (1975).

S. Feinstone et al., Transfusion–Associated Hepatitis Not Due to Viral Hepatitis Type A or B, *The New England Journal of Medicine* vol. 292 No. 15:pp. 767–770 (1975).

J. Simons et al., Identification of two flavivirus–like genomes in the GB Hepatitis agent, *Proc. Natl. Acad. Sci. USA* vol. 92:pp. 3401–3405 (1995).

J. Simons et al., Isolation of novel virus–like sequences associated with human hepatitis, *Nature Medicine* vol. 1 No. 6:pp. 564–568 (1995).

G. Schlauder et al., Molecular and Serologic Analysis in the Transmission of the GB Hepatitis Agents, *Journal of Medical Virology* vol. 46:pp. 81–90 (1995).

M. Yoshiba et al., Detection of the GBV–C hepatitis virus genome in serum from patients with fulminant hepatitis of unknown aetiology, *The Lancet* vol. 346:pp. 1131–1132 (1995).

J. Linnen et al., Molecular Cloning and Disease Association of Hepatitis G Virus: A Transfusion–Transmissible Agent, *Science* vol. 271:pp. 505–508 (1996).

A. Zuckerman, The new GB hepatitis viruses, *The Lancet* vol. 345:pp. 1453–1455 (1995).

L. Altman., Three Newly Discovered Viruses May Cause Unexplained Hepatitis, *The New York Times Medical Science*, Apr. 11, 1995.

L. Altman., Newly Found Viruses May Cause Hepatitis, *The New York Times Medical Science*, Apr. 10, 1995.

T. Leary et al., Sequence and Genomic Organization of GBV–C: A novel Member of the Flaviviridae Associated with Human Non–A–E Hepetitis, *Journal of Medical Virology* vol. 48:pp. 80–87 (1996).

G. Caetano–Anolles et al., DNA Amplification Fingerprinting Using Arbitrary Oligonucleotide Primers, *Applied Biochemistry and Biotechnology* vol. 42:pp. 189–200 (1993).

B. Bassam, DNA amplification fingerprinting of bacteria, *Applied Microbiology and Biotechnology* vol. 38:pp. 70–76 (1992).

G. Caetano–Anolles et al., DNA Amplification Fingerprinting Using Very Short Arbitrary Oligonucleotide Primers, *Biotechnology* vol. 9:pp. 553–557 (1991).

J. Welsh et al., Fingerprinting genomes using PCR with arbitrary primers*, *Nucleic Acids Research* vol. 18 No. 24:pp. 7213–7218 (1990).

J. Welsh et al., Arbitrarily Primed PCR fingerprinting of RNA, *Nucleic Acids Research* vol. 20 No. 19:pp. 4965–4970 (1992).

J. Williams et al., DNA polymorphisms amplified by arbitrary primers are useful as genetic markers, *Nucleic Acids Research* vol. 18 No. 22:pp. 6531–6535 (1990).

P. Liang et al., Differential Display of Eukaryotic Messenger RNA by Means of the Polymerase Chain Reaction, *Science* vol. 257:pp. 967–971 (1992).

P. Liang et al., Distribution and cloning of eukaryotic mRNAs by means of differential display: refinements and optimization, *Nucleic Acids Research* vol. 21 No. 14:pp. 3269–3275 (1993).

```
        1                                                      50
76      -----------A----------TG--AG-C-C-----A-A-T-------
75      -----------A----------TG---G-C-C-----A-A-T-------
 2      -----------A----------TG---G-C-C-----A-A-T-------
83      -----------A--A-------TG---G-C-C------A-T--------
73      -----------A--A-------TG---G-C-T------A----------
77      -----------A--A-------TG---G-C-T------A----------
 3      -----------G----------TG---G-C-C------A----------
80      ..................................................
 5      ----------CTG---------T----G-C-C-GC----A---------
65      ----------CTA--------------G-C-C-------A---------
74      ----------CTA--------------G-C-C-------A---------
66      ----------CTA--------------G-C-C-------A---------
 4      ----------CTG--------------G-C-C-------A---------
67      ----------CTG--------------G-C-A-------A---------
68      ----------CTA--------------G-C-A-------A---------
69      ----------CTA--------------GTC-A-------A---------
71      ----------CTA--------------GTC-A-------A---------
70      ----------CTA--------------GTC-A-------A---------
72      ----------CTA--------------GTC-A-------A---------
64      ----------CTA--------------GTC-A-------A---------
 6      ----------CTA--------------G-T-A-------A---------
63      --------T---AC-----TT----AC----------------------
78      --------T---AC-----TT----AC----------------------
16      ---------------------------T---------------------
17      ---------------------------T---------------------
18      ---------------------------T---------------------
21      ---------------------------T-T-TT----------------
22      ---------------------------T---------------------
19      ---------------------------T---------------------
20      ---------------------------T---------------------
82      ---------------------------T---------------------
24      ---------------------------T---------------------
79      ..................................................
13      ---------------------------T-------A--T----------
84      ---------------------------T----------T----------
60      ---------------------------T----------T----------
85      ---------------------------T-------A--T----------
62      ..................................................
86      ------------------------G--T----------T----------
 9      ---------------------------T----------T----------
10      ---------------------------T----------T----------
11      ---------------------------T----------T----------
14      ---------------------------T----------T----------
15      -------T-------------------T----------T----------
81      ---------------------------T----------T----------
61      
CONS    ACCGACGCCTATCTAAGTAGACGCAATGAC-CGGCGCCGACCCGGCGACC
```

```
        151                                                   200
76    -----C-C--T-A---A----A-----------------------------
75    -----C-C--T-A---A----A-----------------------------
 2    -----C-C--T-A---A----A-----------------------------
83    -----C-C--T-AC--A----A---------T-------------------
73    -----C-C--T-AC--A----AG------------------------T---
77    -----C-C--T-AC--A----AG------------------------T---
 3    -----C-C--T-----A----A-------------------------T---
80    -------C--T-A---A-GA-C-------------------------T---
 5    -------C--A-A---A-GA-A-------------------------T---
65    ----------------A-G--A-------------------------T---
74    ----------------A-G--A-------------------------T---
66    ----------------A-G--A-------------------------T---
 4    ----------------A-G--AC------------------------T---
67    ---------T-A---AAG--A-------------------------AT---
68    ---------T-A---AAG--A-------------------------AT---
69    ------------A---A-G--A------------------------AT---
71    ------------A---A-G--A------------------------AT---
70    ------------A---A-G--A------------------------AT---
72    ------------A---A-G--A------------------------AT---
64    ------C---CA---A-G--A--------------------------.G---
 6    ------C--T-A---AAG--A--------------------------.G---
63    -----G-C--T---------A------------------------------
78    -----A-C--T---------A------------------------------
16    ------------------C--------------------------------
17    ------------------C--------------------------------
18    ------------------C--------------------------------
21    ------------------C--------------------------------
22    ------------------CG-------------------------------
19    ------------------C--------------------------------
20    ------------------C--------------------------------
82    ------------------C--------------------------------
24    ------------------C--------------------------------
79    -------------C-------CC----------------------------
13    -------------C-------CC----------------------------
84    -------------C-------CC---------------C-----T--
60    -------------C-------CC---------------C-----T--
85    -------------C-------CC----------------------------
62    -------------C-------CC----------------------------
86    ------C------C-------CC----------G------A---------
 9    -------------C-------CC----------------------------
10    -------------C-------CC----------------------------
11    -------------C-------CC----------------------------
14    -------------C-------CC----------------------------
15    -------------C-------ACA--------------------G------
81    -------------C-------CC----------------------------
61    -------------C-------CC----------------------------
CONS  CCTCTTGTGCCTGTGGCGAGA-AGCGCACGGTCCACAGGTGTTGGCCCTA
```

```
        251                                                              300
76      -----C-----------------------------C--------------
75      -----C-----------------------------C--------------
2       -----CT----------------------------C--------------
83      -----T-----------------------------C--------------
73      --A--C------------------------------T-------------
77      --A--C------------------------------T-------------
3       --A--C--------------------T-----C-T---------------
80      -----T--------------------------------------------
5       ---T-C--------------------------------------------
65      --T--C-----------------------------C-T------------
74      --T-TC-----------------------------C-A------------
66      G-A--C--------------------T---------T-------------
4       --T--C--------------------T-----C-T---------------
67      -G---CT-------------------------------------------
68      -G---CT-------------------------------------------
69      -----CT----T----------------------------------A---
71      -----CT----T----------------------------------A---
70      -----CT----T----------------------------------A---
72      -----CT----T----------------------------------A---
64      -----CT----T--------------------------------------
6       --T--CT-------------------T-----------------------
63      ----------------------------------------------A---
78      ----------------A-----------------------------A---
16      C-------------------------------------------------
17      C-------------------------------------------------
18      C-------------------------T-----------------------
21      C-------------------------------------------------
22      C-------------------------------------------------
19      C-------------------------------------------------
20      C-------------------------T-----------------------
82      C-------------------------------------------------
24      CC-------------------G---T--T---------------------
79      C----------------------------------T--------------
13      C----------------------------------T--------------
84      --------------------------------------------------
60      --------------------------------------------------
85      C-------------------------T-----------------------
62      C-------------------------------------------------
86      C---------------T---------------------------------
9       C-------------------------------------------------
10      C-------------------------------------------------
11      C-T--G-------T------------------------------------
14      --------------------------------------------------
15      AC------------------------------------------------
81      C----------G--------------------------------------
61      -C---G--------------------------------------------
CONS    TACCCACCTGGGCAAACGACGCCCACGTACGGTCCACGTCGCCCTTCAAT
```

FIG. 1C(2)

```
        301                                                                   350
  76    ---------------------...C-AT-------------------G-----
  75    ---------------------...C-AT-------------------G-----
   2    ---------------------...CAAT-------------------G-----
  83    ---------------------...CAAT-------------------G-----
  73    ---------------------...CAAT------------------------
  77    ---------------------...CAAT------------------------
   3    ---------------------...CAAT-------------------G-----
  80    ---------------------...-CTA------------------------
   5    ---------------------...CG--------------------------
  65    ---------------------...CG---------------------G-----
  74    ---------------------...C----------------------T-G---
  66    ---------------------...CG-----------------G---A-----
   4    ---------------------...C------------------G----G----
  67    ---------------------...C--T------------------------
  68    ---------------------...C--T------------------------
  69    ---------------------...C---------------------------
  71    ---------------------...C---------------------------
  70    ---------------------...C---------------------------
  72    ---------------------...C---------------------------
  64    ---------------------...C---------------------------
   6    -C-------G-----------...----T-----------------------
  63    ---------------------...C--T------------------------
  78    ---------------------...C--T------------------------
  16    --------------------CT--G.C-------------------------
  17    --------------------CT--G.C-------------------------
  18    --------------------CG--G.C-------------------------
  21    ---------------------...-----------------------------
  22    ---------------------...-----------------------------
  19    ---------------------...-----------------------------
  20    ---------------------...-----------------------------
  82    ---------------------...-----------------------------
  24    ---------------------...-----------------------------
  79    -C-------G-----------...----T-----------------------
  13    -C-------G-----------...----T-----------------------
  84    ---------------------...-----------------------------
  60    ---------------------...-----------------------------
  85    ---------------------...-----------------------------
  62    ---------------------...-----------------------------
  86    ---------------------...-----------------------------
   9    ---------------------...----T-----------------------
  10    ---------------------...----T-----------------------
  11    ---------------------...--C-T-----------------------
  14    ---------------------.A--CGT------------------------
  15    -----C---------------...----T-----------------------
  81    -C-------G--------A-A--CCT-----------G--------------
  61    ---------------------...--C-T-----------------------
CONS    GTCTCTCTTGACCAATAGGGCCTTTAGCCGGCGAGTTGACAAGGACCAGT
```

```
       401                                                  450
 76    ------------------------------------C---A---------
 75    ------------------------------------C---A---------
  2    ----------------------------------------A---------
 83    --A-------------------------------------A---------
 73    -T--------------------------------------A---------
 77    -T--------------------------------------A---------
  3    -T--------------------------------------A
 80    ------------------------------------GCAT--........
  5    A---------------------------------------A---------
 65    -A--------------------------------------A---------
 74    -A--------------------------------------A---------
 66    -T----A---------------------------------A---------
  4    -A----A---------------------------------A---------
 67    ----------------------------------------A---------
 68    ----------------------------------------A---------
 69    ----------------------------------------A---------
 71    ----------------------------------------A---------
 70    ----------------------------------------A---------
 72    ----------------------------------------A---------
 64    ----------------------------------------A---------
  6    -A--------------------------------------A---------
 63    ---T----------------------------------------------
 78    ---T---G-------------------------.................
 16    --A-----------------------------------------------
 17    --A-----------------------------------------------
 18    --A-----------------------------------------------
 21    --A-----------------------------------------------
 22    --A-----------------------------------------------
 19    --A-----------------------------------------------
 20    --A-----------------------------------------------
 82    --A-----------------------------------------------
 24    --A-----------------------------------------------
 79    -AA----------------------------------.............
 13    -AA-----------------------------------------------
 84    --C-----------------------------------------------
 60    --C-----------------------------------------------
 85    --C-----------------------------------------------
 62    --C------------------------------.................
 86    --C-----------------------------------------------
  9    --C-----------------------------------------------
 10    --C-----------------------------------------------
 11    -AC-----------------------------------------------
 14    --------------------------------------------------
 15    --A-----------------------------------------------
 81    --C-----------------------------------------------
 61    --Y------------------------------GCAT--GGCCACC-A-..
CONS   GGGCGGGAAATGCATGGGGCCACCCAGCTCCGCGGCGGCCTGCAGCCGGG
```

```
                551                                                              597
     76         ------------------A---------A-T--T--A---------C---
     75         ------------------A---------G-T--T--A---------C---
      2         ------------------A--T------A-T--T--A---------C---
     83         ---------------------T------A-C--T--A-------------
     73         --T------------------T----CA-T--A--G----------C---
     77         --T------------------T----CA-T--A--G----------C---
      3         ------------------A---------A-C--A--G----------C---
     80         ....................................................
      5         --T-A----------------T------A-C-----A--------------
     65         ------------------A--T------A-T--T--G--------------
     74         --T------------------T------A-T--T--A--------------
     66         --T------------------T------A-T--TGG---------------
      4         --T------------------T------A-C-----G--------------
     67         ---------------------T------A-T-----G--------------
     68         ---------------------T------A-T-----G--------------
     69         ---------------------T------G-T---C-G--A-----------
     71         ---------------------T------G-T---C-G--A-----------
     70         ---------------------T------G-T---C-G--A-----------
     72         ------------------TA--------G-T---C-G--A-----------
     64         --T------------------T------A-T---C-G--A-----------
      6         ---------------------T------A-C-----G--------------
     63         ------------------A---------G----------------------
     78         ....................................................
     16         ----------------------------------TG----------------
     17         ----------------------------------TG----------------
     18         ----------------------------------TG----------------
     21         -----------------------------G----------------C---
     22         -----------------------------G----------------C---
     19         ---------------------------C-----TG----A------------
     20         -----------------------------G--TG------------------
     82         ------------------------------TGG------------------
     24         --T--------------------------G--TG-----------------
     79         .................................C..................
     13         ---------------------------------------------------
     84         --------------------------G------------------------
     60         --------------------------G------------------------
     85         ---------------------------------------------C---
     62         ....................................................
     86         --T------------------------------------------------
      9         ----------------------------------------------C---
     10         ----------------------------------------------C---
     11         ---------------------------------------------------
     14         --T------------------T-----------------------------
     15         ---------------------------------------------------
     81         -------------------A-------------------------------
     61         ....................................................
    CONS        TTCTGGCCCCGGCCACCCACGCTTGTCGAGCGAATGGGCAATATTTC
```

DETECTION OF HEPATITIS GB VIRUS GENOTYPES

RELATED APPLICATIONS

This application claims the benefit of U.S. provisional application Ser. No. 60/002,265, filed Aug. 14, 1995 which is incorporated herein by reference.

This application is related in subject matter to the following applications, which enjoy common ownership and are incorporated herein by reference: U.S. Ser. No. 60/002,255 filed Aug. 14, 1995; U.S. Ser. No. 08/480,995 filed Jun. 7, 1995, U.S. Ser. No. 08/473,475 filed Jun. 7, 1995, and U.S. Ser. No. 08/417,629, filed Apr. 6, 1995, which are continuation-in-part applications of U.S. Ser. No. 08/377, 557 filed Jan. 30, 1995, which is a continuation-in-part of U.S. Ser. No. 08/424,550 filed Jun. 5, 1995, which is a nationalization of P.C.T. application PCT/US95/02118 filed Feb. 14, 1995, which is a continuation in part application of U.S. Ser. No. 08/344,185 filed Nov. 23, 1994 and U.S. Ser. No. 08/344,190 filed Nov. 23, 1994, which are continuation-in-part applications of 08/283,314 filed Jul. 29, 1994, which is a continuation-in-part application of U.S. Ser. No. 08/242, 654, filed May 13, 1994, which is a continuation-in-part application of U.S. Ser. No. 08/196,030 filed Feb. 14, 1994.

BACKGROUND OF THE INVENTION

This invention relates generally to hepatitis GB virus and more particularly, relates to oligonucleotide primers and probes useful for detection of genotypes of hepatitis GB virus.

Several lines of epidemiological and laboratory evidence have suggested the existence of more than one parenterally transmitted non-A, non-B (NANB) hepatitis-causing agent, including multiple attacks of acute NANBH in intravenous drug users, distinct incubation periods of patients acquiring NANBH post-transfusion, the outcome of cross-challenge chimpanzee experiments, the ultrastructural liver pathology of infected chimpanzees and the differential resistance of the putative agents to chloroform. J. L. Dienstag, *Gastroenterology* 85:439–462 (1983); J. L. Dienstag, *Gastroenterology* 85:743–768 (1983); F. B. Hollinger et al., *J. Infect. Dis.* 142:400–407 (1980); D. W. Bradley in F. Chisari, ed., *Advances in Hepatitis Research*, Masson, N.Y., pp. 268–280 (1984); and D. W. Bradley et al., *J. Infect. Dis.* 148:254–265 (1983).

The detection of hepatitis C virus (HCV) antibody in donor samples now eliminates 70 to 80% of NANBH infected blood in the blood supply system. Thus, the detection of HCV has not totally prevented the transmission of hepatitis. H. Alter et al., *New Eng. J. Med.* 321:1494–1500 (1989). Recent publications also have questioned whether additional hepatitis agents may be responsible for post-transfusion hepatitis (PTH) and for community acquired acute and/or chronic hepatitis that is not associated with PTH. For example, of 181 patients monitored in a prospective clinical survey conducted in France from 1988 to 1990, investigators noted a total of 18 cases of PTH. Thirteen of these 18 patients tested negative for anti-HCV antibodies, hepatitis B virus surface antigen (HBsAg), hepatitis B virus (HBV) and HCV nucleic acids. The authors speculated as to the potential importance of a non-A, non-B, non-C agent causing PTH. V. Thiers et al., *J. Hepatology* 18:34–39 (1993). Also, of 1,476 patients monitored in another study conducted in Germany from 1985 to 1988, 22 cases of documented cases of PTH were not related to infection with HBV or HCV. T. Peters et al., *J. Med. Virol.* 39:139–145 (1993).

Recently, a new family of flaviviruses detected in patients with clinically diagnosed hepatitis was reported. This new family of viruses has been named the "GB" viruses, after the initials of the patient first infected with the virus. These viruses have been reported by J. N. Simons et al., *Proc. Natl. Acad. Sci. USA* 92:3401–3405 (1995); and J. N. Simons et al., *Nature Medicine* 1(6):564–569 (1995). Studies currently are underway to determine the clinical and epidemiological significance of these viruses.

As has been noted with hepatitis C virus, genotypes vary in nucleotide and amino acid sequence as well as in severity of the disease and geographical location. See, for example, G. Dawson et al., "Recent Developments in the Molecular Biology of the Hepatitis Virus," in *Current Hepatology*, G. Gitnick, ed., Mosby Publishers (1995, in press). Thus, detection of genotypes of HGBV can aid in the clinical and epidemiological understanding of the virus.

The detection of HGBV in test samples can be enhanced by the use of DNA hybridization assays which utilize DNA oligomers as hybridization probes. Since the amount of DNA target nucleotides present in a test sample may be in minute amounts, target DNA usually is amplified and then detected. Methods for amplifying and detecting a target nucleic acid sequence that may be present in a test sample are well-known in the art. Such methods include the polymerase chain reaction (PCR) described in U.S. Pat. Nos. 4,683,195 and 4,683,202 which are incorporated herein by reference, the ligase chain reaction (LCR) described in EP-A-320 308, gap LCR (GLCR) described in European Patent Application EP-A-439 182 and U.S. Pat. No. 5,427, 930 which are incorporated herein by reference, multiplex LCR described in International Patent Application No. WO 93/20227, NASBA and the like. These methods have found widespread application in the medical diagnostic field as well as in the fields of genetics, molecular biology and biochemistry.

It would be advantageous to provide DNA probes derived from HGBV which can detect HGBV in test samples of individuals suspected of being infected with HGBV and test kits which utilize these probes. Such probes could greatly enhance the ability of the medical community to more accurately diagnose acute and/or chronic viral hepatitis and could provide a safer blood and organ supply by detecting non-A, non-B and non-C hepatitis in these blood and organ donations, and could provide a better understanding of the prevalence of HGBV in the population, epidemiology of the disease caused by HGBV and the prognosis of infected individuals.

SUMMARY OF THE INVENTION

The present invention provides unique primers for HGBV-C detection. These primers are identified as SEQUENCE ID NO 51, SEQUENCE ID NO 53, SEQUENCE ID NO 54, SEQUENCE ID NO 55, SEQUENCE ID NO 56, SEQUENCE ID NO 57, and SEQUENCE ID NO 87, and complements thereof. The primer(s) disclosed herein can detect the presence of HGBV-C and are not reactive with HGBV-A or HGBV-B.

The present invention also provides a method of detection target HGBV-C nucleotides in a test sample, comprising contacting a target HGBV nucleotide with at least one oligonucleotide and detecting the presence of the target in the test sample. The oligonucleotides can be selected from the group consisting of SEQUENCE ID NO 51, SEQUENCE ID NO 53, SEQUENCE ID NO 54, SEQUENCE ID NO 55, SEQUENCE ID NO 56, SEQUENCE ID NO 57, and SEQUENCE ID NO 87, and complements thereof. The oligonucleotides utilized also can be selected from the group consisting of SEQUENCE ID NO 2, SEQUENCE ID NO 3, SEQUENCE ID NO 4, SEQUENCE ID NO 5, SEQUENCE ID NO 6, SEQUENCE ID NO 9, SEQUENCE ID NO 10, SEQUENCE ID NO 11, SEQUENCE ID NO 13, SEQUENCE ID NO 13, SEQUENCE ID NO 14, SEQUENCE ID NO 15, SEQUENCE ID NO 16, SEQUENCE ID NO 17, SEQUENCE ID NO 18, SEQUENCE ID NO 19, SEQUENCE ID NO 20, SEQUENCE ID NO 21, SEQUENCE ID NO 22, SEQUENCE ID NO 23, SEQUENCE ID NO 24, SEQUENCE ID NO 60, SEQUENCE ID NO 61, SEQUENCE ID NO 62, SEQUENCE ID NO 63, SEQUENCE ID NO 64, SEQUENCE ID NO 65, SEQUENCE ID NO 66, SEQUENCE ID NO 67, SEQUENCE ID NO 68, SEQUENCE ID NO 69, SEQUENCE ID NO 70, SEQUENCE ID NO 71, SEQUENCE ID NO 72, SEQUENCE ID NO 73, SEQUENCE ID NO 74, SEQUENCE ID NO 75, SEQUENCE ID NO 76, SEQUENCE ID NO 77, SEQUENCE ID NO 78, SEQUENCE ID NO 79, SEQUENCE ID NO 80, SEQUENCE ID NO 81, SEQUENCE ID NO 82, SEQUENCE ID NO 83, SEQUENCE ID NO 84, SEQUENCE ID NO 85 and SEQUENCE ID NO 86.

The present invention also provides a method of amplifying 5' end cDNA of hepatitis GB-C (HGBV-C) virus in a test sample, comprising performing reverse transcription with random primers and test sample, amplifying the cDNA so obtained by using other oligonucleotide primers as sense and antisense primers in a first stage PCR to obtain amplified cDNA of HGBV-C, and detecting the presence of the amplicon (amplified cDNA) in the test sample. At least one oligonucleotide used as a sense primer can be selected from the group consisting of SEQUENCE ID NO.51, SEQUENCE ID NO 53 and SEQUENCE ID NO 56. At least one oligonucleotide used as an antisense primer can be selected from the group consisting of SEQUENCE ID NO 54, SEQUENCE ID NO 55, SEQUENCE ID NO 57 and SEQUENCE ID NO 87.

The present invention also provides a method for detecting target hepatitis GB-C virus (HGBV-C) in a test sample suspected of containing target HGBV-C, comprising contacting the test sample with at least one oligonucleotide of HGBV-C as a sense primer and at least one oligonucleotide of HGBV-C as an anti-sense primer and amplifying same to obtain a first stage reaction product; then contacting the first stage reaction product with at least one of the oligonucleotides used previously and a second oligonucleotide, with the proviso that the second oligonucleotide is located 3' to the first oligonucleotide utilized and is of opposite sense to the first oligonucleotide, and then detecting the HGBV target. The first stage PCR reaction can comprise utilizing at least one oligonucleotide selected from the group consisting of SEQUENCE ID NO 51, SEQUENCE ID NO 56 and SEQUENCE ID NO 53 as a sense primer and utilizing at least one oligonucleotide selected from the group consisting of SEQUENCE ID NO 54, SEQUENCE ID NO 55, SEQUENCE ID NO 57 and SEQUENCE ID NO 87 as an anti-sense primer. The products of this first stage PCR then can be further amplified in a second stage PCR reaction which comprises utilizing at least one oligonucleotide selected from the group consisting of SEQUENCE ID NO 56 and SEQUENCE ID NO 53 as a sense primer, and utilizing at least one oligonucleotide selected from the group consisting of SEQUENCE ID NO 54, SEQUENCE ID NO 55 and SEQUENCE ID NO 57 as an anti-sense primer, with the proviso that the second oligonucleotide is located 3' to the first oligonucleotide utilized and is of opposite sense to the first oligonucleotide.

The amplification in all methods can be performed by the polymerase chain reaction (PCR). The test sample in these methods can be attached to a solid phase prior to performing the methods steps outlined hereinabove. Further, the detection step of these methods can comprise utilizing a detectable measurable signal generating compound (label) which generates a measurable signal. Moreover, the label can be attached to a solid phase.

GAP LCR also can be performed according to the invention, utilizing SEQUENCE ID NO 35, SEQUENCE ID NO 36, SEQUENCE ID NO 37, SEQUENCE ID NO 38, SEQUENCE ID NO 39, SEQUENCE ID NO 40, SEQUENCE ID NO 41, SEQUENCE ID NO 42, SEQUENCE ID NO 43, SEQUENCE ID NO 44, SEQUENCE ID NO 45, SEQUENCE ID NO 46, SEQUENCE ID NO 47, SEQUENCE ID NO 48, SEQUENCE ID NO 49 and SEQUENCE ID NO 50, for genotype differentiation.

BRIEF DESCRIPTION OF THE DRAWINGS

Figure 1A:
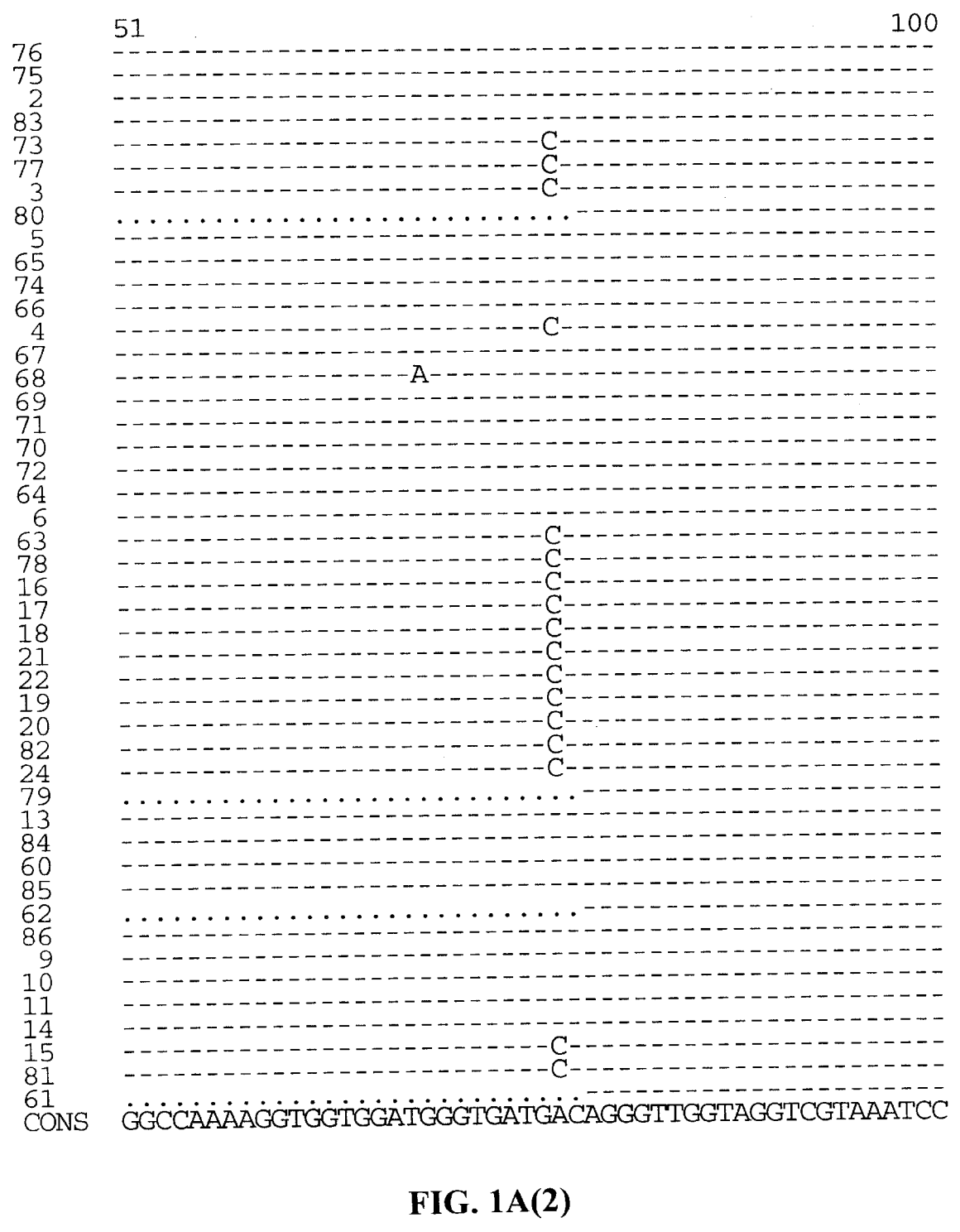
Figure 1B:
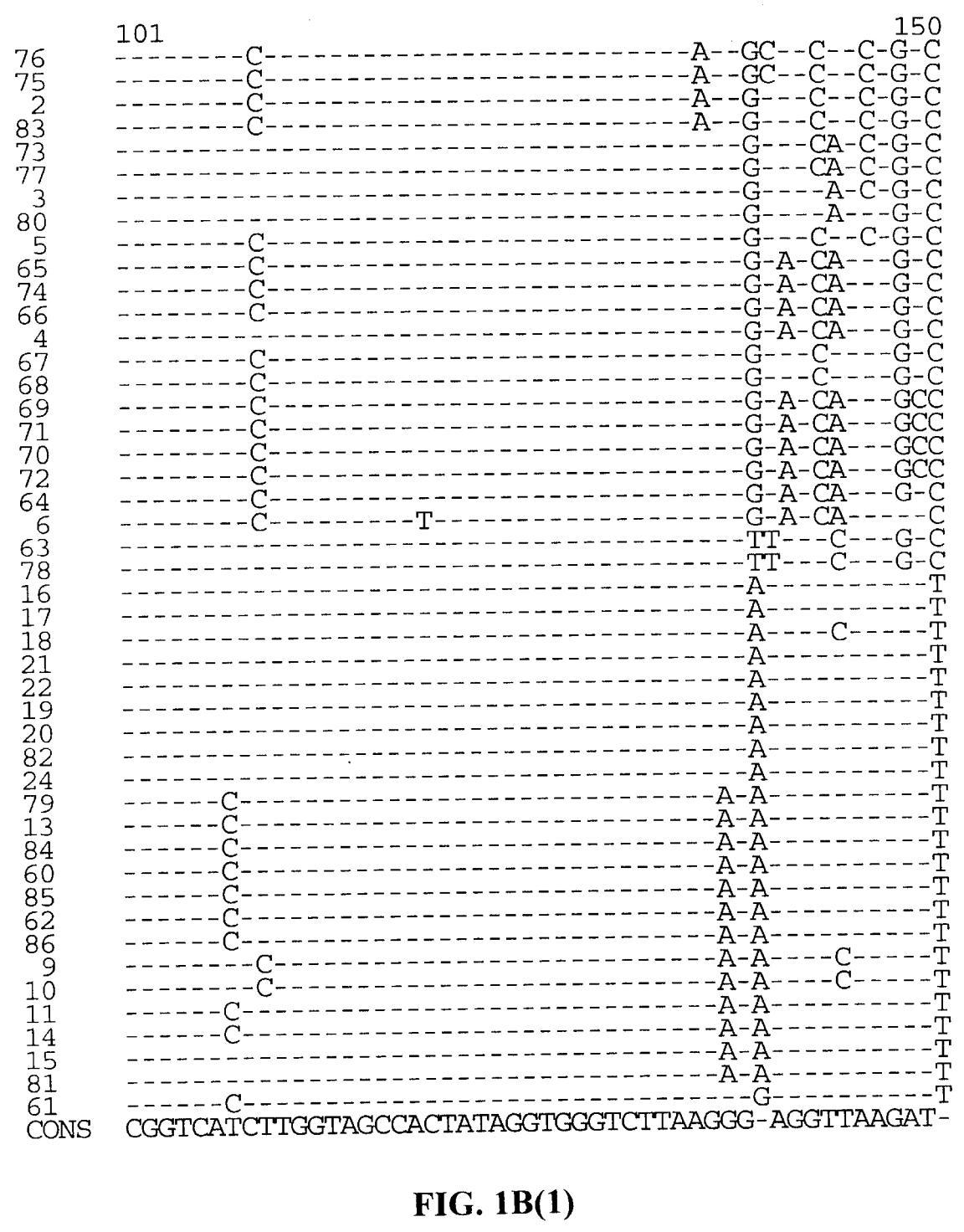
Figure 1C:
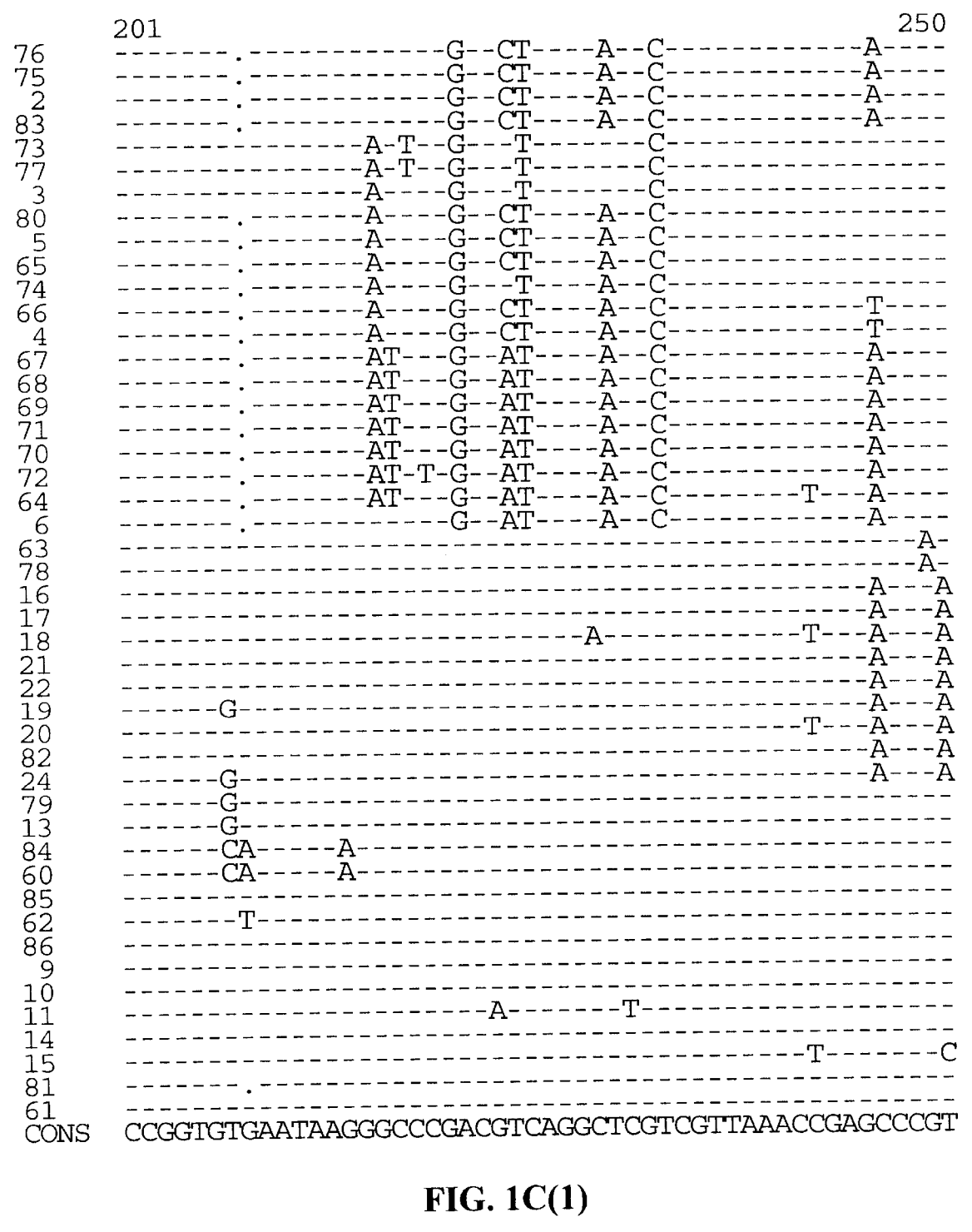
Figure 1D:
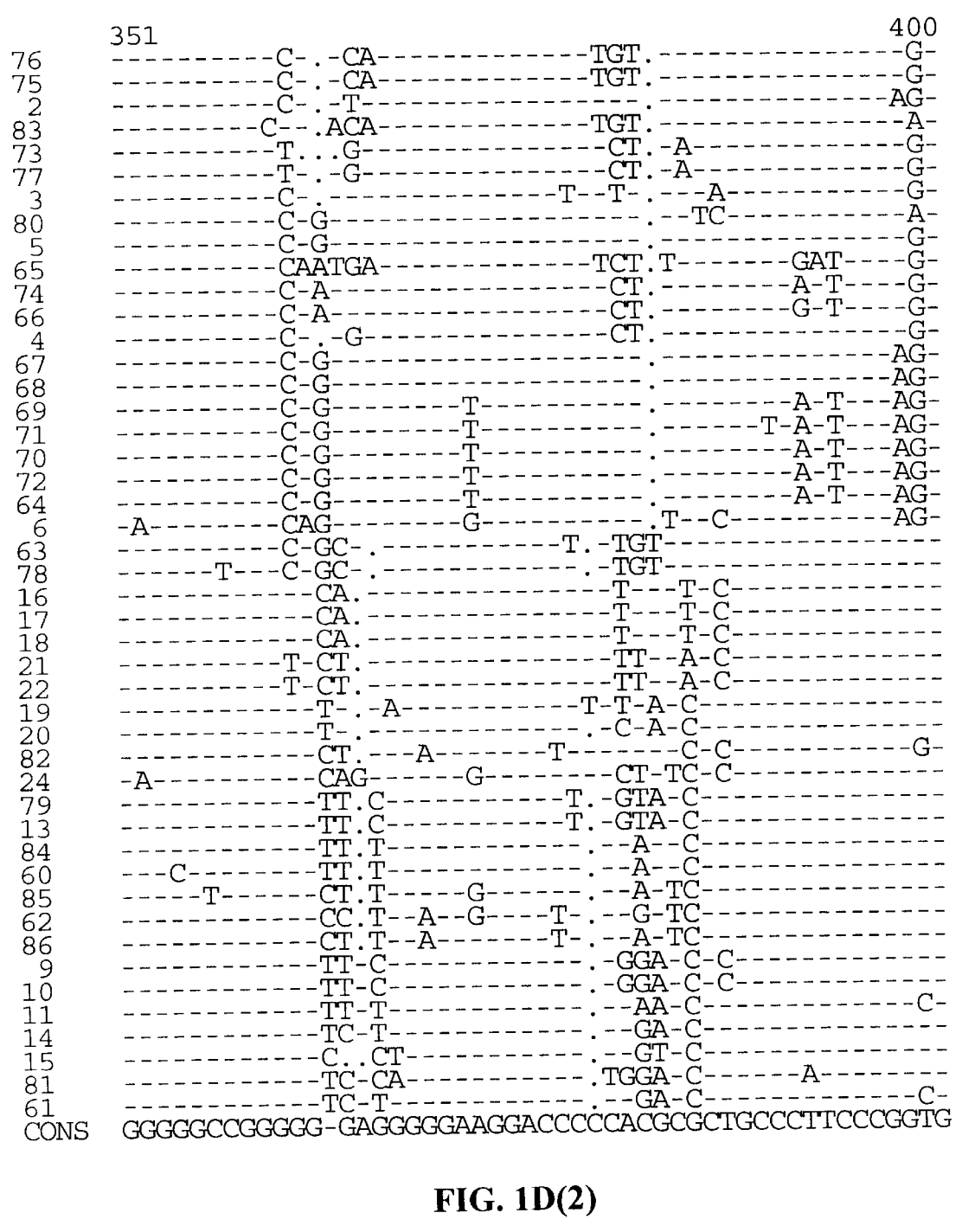
Figure 1E:
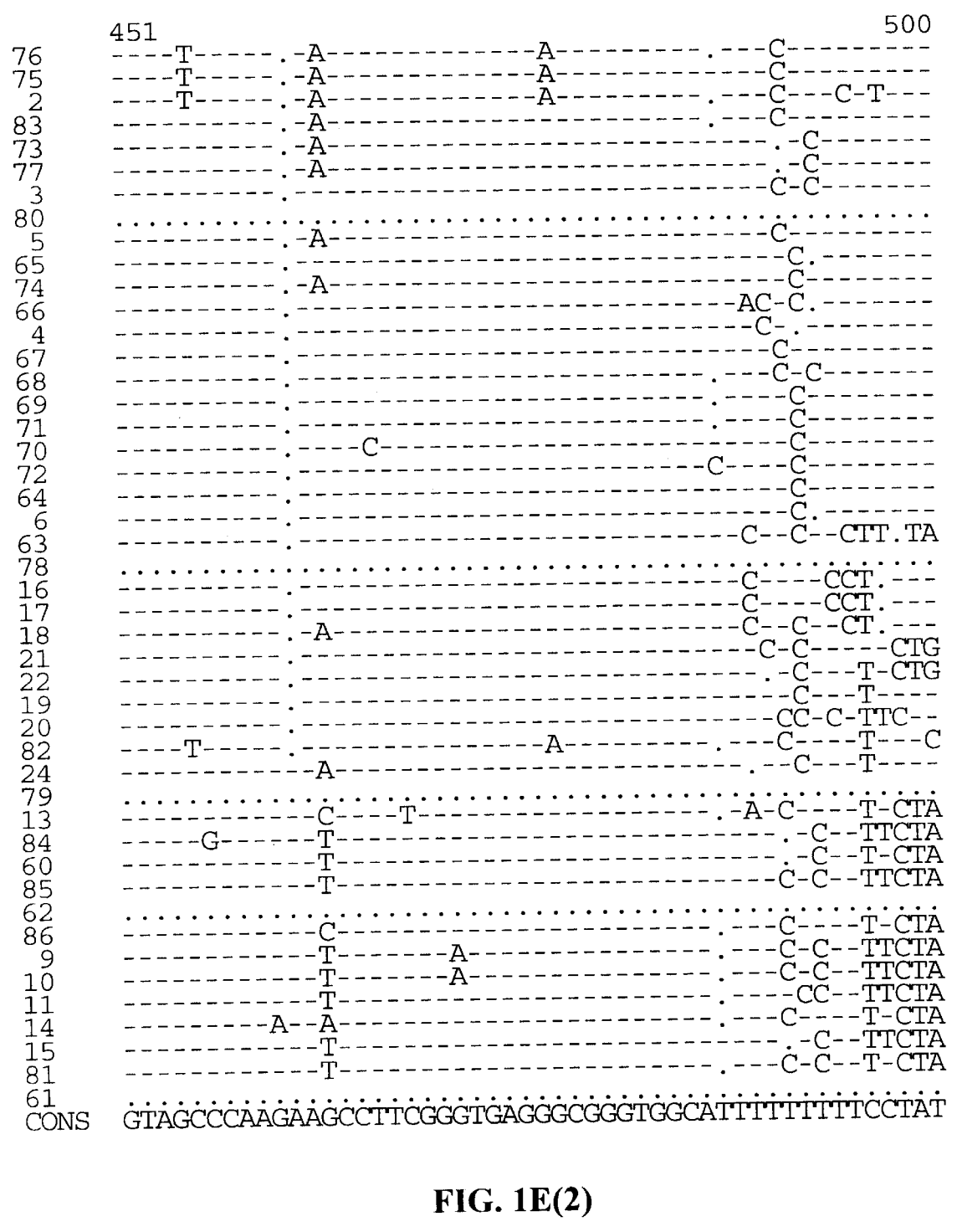
Figure 1F:
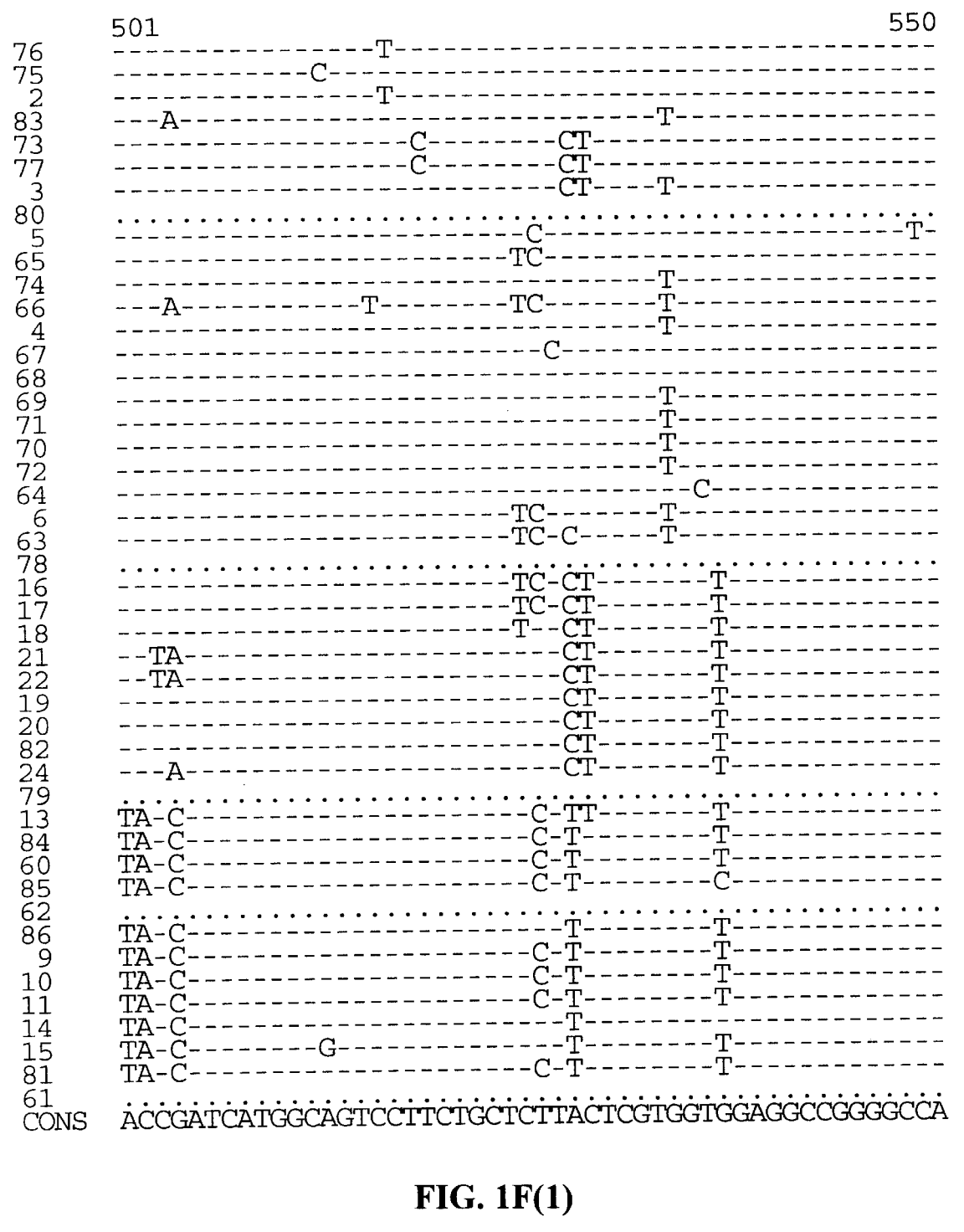

FIGS. 1A through FIG. 1F show the nucleotide alignment of the HGBV-C isolates.

DETAILED DESCRIPTION OF THE INVENTION

Figure 2:
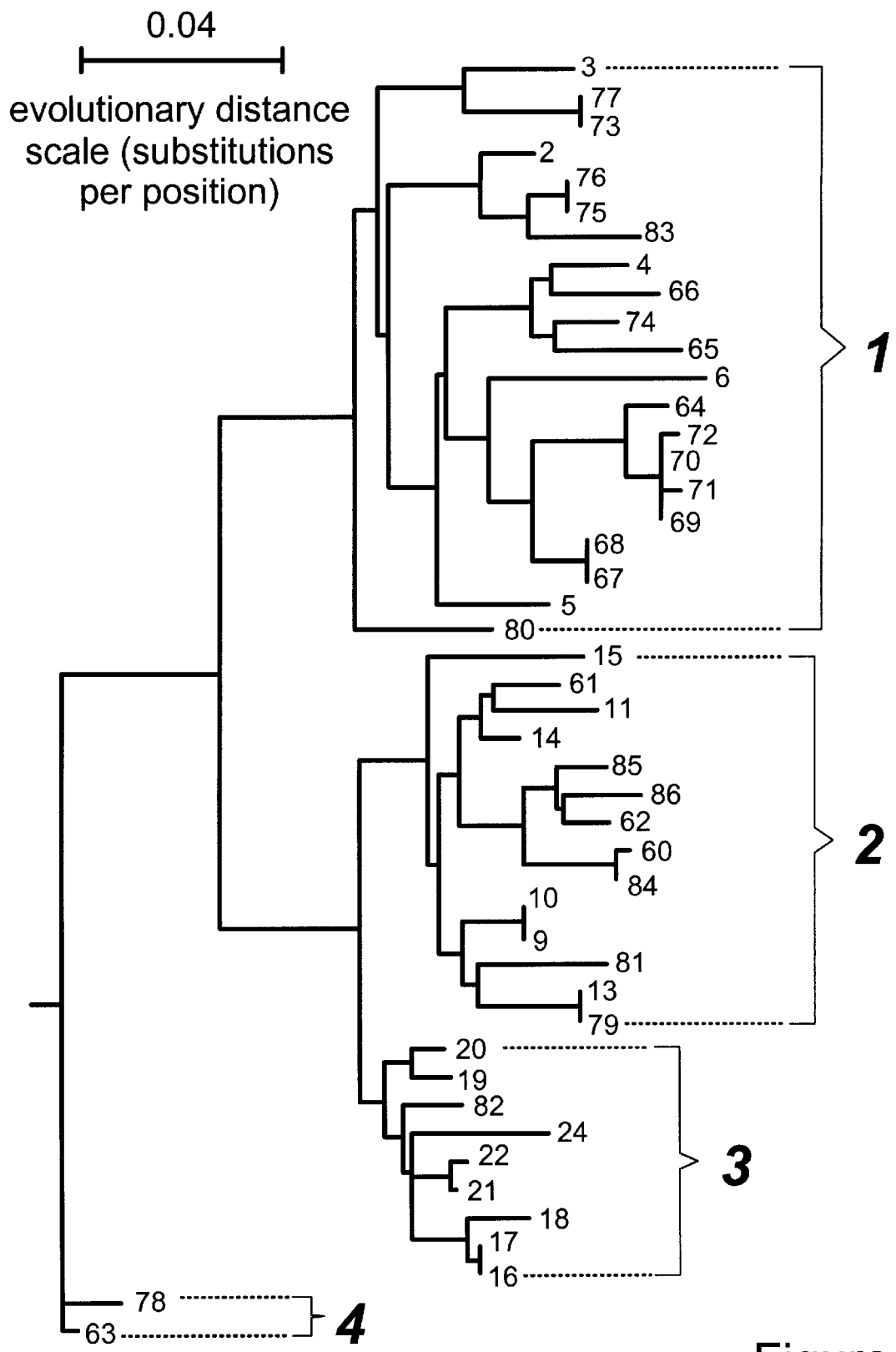
FIG. 2 shows a phylogenetic tree of the genotypes of HGBV-C.

The present invention provides characterization of a newly ascertained genotypes of etiological agents of non-A, non-B, non-C, non-D and non-E hepatitis-causing agents, collectively so-termed "Hepatitis GB Virus," or "HGBV." The present invention provides a method for detecting HGBV genotypes, oligonucleotides useful for detecting HGBV and oligonucleotides useful for differentiating HGBV-C genotypes. The present invention provides kits containing reagents which can be used for the detection of HGBV genotypes, such reagents comprising a polynucleotide probe containing a nucleotide sequence from HGBV of about 8 or more nucleotides in a suitable container The term "Hepatitis GB Virus" or "HGBV", as used herein, collectively denotes a viral species which causes non-A, non-B, non-C, non-D, non-E hepatitis in man, and attenuated strains or defective interfering particles derived therefrom. This may include acute viral hepatitis transmitted by contaminated foodstuffs, drinking water, and the like; hepatitis due to HGBV transmitted via person to person contact (including sexual transmission, respiratory and parenteral routes) or via intravenous drug use. The methods as described herein will allow the identification of individuals who have acquired HGBV. Individually, the HGBV isolates are specifically referred to as "HGBV-A", "HGBV-B" and "HGBV-C." As described herein, the HGBV genome is comprised of RNA. Analysis of the nucleotide sequence and deduced amino acid sequence of the HGBV reveals that viruses of this group have a genome organization similar to that of the Flaviridae family. Based primarily, but not exclusively, upon similarities in genome organization, the International Committee on the Taxonomy of Viruses has recommended that this family be composed of three genera: Flavivirus, Pestivirus, and the hepatitis C group. Similarity searches at the amino acid level reveal that the hepatitis GB virus subclones have some, albeit low, sequence resemblance to hepatitis C virus. It now has been demonstrated that HGBV-C is not a genotype of HCV. See, for example, U.S. Ser. No. 08/417,629, filed Apr. 6, 1995, previously incorporated herein by reference.

The term "similarity" and/or "identity" are used herein to describe the degree of relatedness between two polynucleotides or polypeptide sequences. The techniques for determining amino acid sequence "similarity" and/or "identity" are well-known in the art and include, for example, directly determining the amino acid sequence and comparing it to the sequences provided herein; determining the nucleotide sequence of the genomic material of the putative HGBV (usually via a cDNA intermediate), and determining the amino acid sequence encoded therein, and comparing the corresponding regions. In general, by "identity" is meant the exact match-up of either the nucleotide sequence of HGBV and that of another strain(s) or the amino acid sequence of HGBV and that of another strain(s) at the appropriate place on each genome. Also, in general, by "similarity" is meant the exact match-up of amino acid sequence of HGBV and that of another strain(s) at the appropriate place, where the amino acids are identical or possess similar chemical and/or physical properties such as charge or hydrophobicity. The programs available in the Wisconsin Sequence Analysis Package, Version 8 (available from the Genetics Computer Group, Madison, Wis., 53711), for example, the GAP program, are capable of calculating both the identity and similarity between two polynucleotide or two polypeptide sequences. Other programs for calculating identity and similarity between two sequences are known in the art.

Additionally, the following parameters are applicable, either alone or in combination, in identifying a strain of HGBV-A, HGBV-B or HGBV-C. It is expected that the overall nucleotide sequence identity of the genomes between HGBV-A, HGBV-B or HGBV-C and a strain of one of these hepatitis GB viruses will be about 45% or greater, since it is now believed that the HGBV strains may be genetically related, preferably about 60% or greater, and more preferably, about 80% or greater.

Also, it is expected that the overall sequence identity of the genomes between HGBV-A and a strain of HGBV-A at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-B and a strain of HGBV-B at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-C and a strain of HGBV-C at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence.

A polynucleotide "derived from" a designated sequence for example, the HGBV cDNA, or from the HGBV genome, refers to a polynucleotide sequence which is comprised of a sequence of approximately at least about 6 nucleotides, is preferably at least about 8 nucleotides, is more preferably at least about 10–12 nucleotides, and even more preferably is at least about 15–20 nucleotides corresponding, i.e., similar to or complementary to, a region of the designated nucleotide sequence. Preferably, the sequence of the region from which the polynucleotide is derived is similar to or complementary to a sequence which is unique to the HGBV genome. Whether or not a sequence is complementary to or similar to a sequence which is unique to an HGBV genome can be determined by techniques known to those skilled in the art. Comparisons to sequences in databanks, for example, can be used as a method to determine the uniqueness of a designated sequence. Regions from which sequences may be derived include but are not limited to regions encoding specific epitopes, as well as non-translated and/or non-transcribed regions.

The derived polynucleotide will not necessarily be derived physically from the nucleotide sequence of HGBV, but may be generated in any manner, including but not limited to chemical synthesis, replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, either by methylation and/or by capping, and unmodified forms of the polynucleotide.

The terms "polynucleotide," "oligomer," "oligonucleotide," "oligo" and "primer" are used interchangeably herein.

"HGBV containing a sequence corresponding to a cDNA" means that the HGBV contains a polynucleotide sequence which is similar to or complementary to a sequence in the designated DNA. The degree of similarity or complementarity to the cDNA will be approximately 50% or greater, will preferably be at least about 70%, and even more preferably will be at least about 90%. The sequence which corresponds will be at least about 70 nucleotides, preferably at least about 80 nucleotides, and even more preferably at least about 90 nucleotides in length. The correspondence between the HGBV and the cDNA can be determined by methods known in the art, and include, for example, a direct comparison of the sequenced material with the cDNAs described, or hybridization and digestion with single strand nucleases, followed by size determination of the digested fragments.

"Purified viral polynucleotide" refers to an HGBV genome or fragment thereof which is essentially free, i.e., contains less than about 50%, preferably less than about 70%, and even more preferably, less than about 90% of polypeptides with which the viral polynucleotide is naturally associated. Techniques for purifying viral polynucleotides are well known in the art and include, for example, disruption of the particle with a chaotropic agent, and separation of the polynucleotide(s) and polypeptides by ion-exchange chromatography, affinity chromatography, and sedimentation according to density. Thus, "purified viral polypeptide" means an HGBV polypeptide or fragment thereof which is essentially free, that is, contains less than about 50%, preferably less than about 70%, and even more preferably, less than about 90% of cellular components with which the viral polypeptide is naturally associated. Methods for purifying are known to the routineer.

"Polypeptide" as used herein indicates a molecular chain of amino acids and does not refer to a specific length of the product. Thus, peptides, oligopeptides, and proteins are included within the definition of polypeptide. This term, however, is not intended to refer to post-expression modifications of the polypeptide, for example, glycosylations, acetylations, phosphorylations and the like.

A "polypeptide" or "amino acid sequence derived from a designated nucleic acid sequence or from the HGBV genome refers to a polypeptide having an amino acid sequence identical to that of a polypeptide encoded in the sequence or a portion thereof wherein the portion consists of at least 3 to 5 amino acids, and more preferably at least 8 to 10 amino acids, and even more preferably 15 to 20 amino acids, or which is immunologically identifiable with a polypeptide encoded in the sequence.

A "recombinant polypeptide" as used herein means at least a polypeptide of genomic, semisynthetic or synthetic origin which by virtue of its origin or manipulation is not associated with all or a portion of the polypeptide with which it is associated in nature or in the form of a library and/or is linked to a polynucleotide other than that to which it is linked in nature. A recombinant or derived polypeptide is not necessarily translated from a designated nucleic acid sequence of HGBV or from an HGBV genome. It also may be generated in any manner, including chemical synthesis or expression of a recombinant expression system, or isolation from mutated HGBV.

The term "synthetic peptide" as used herein means a polymeric form of amino acids of any length, which may be chemically synthesized by methods wellknown to the routineer. These synthetic peptides are useful in various applications.

"Recombinant host cells," "host cells," "cells," "cell lines," "cell cultures," and other such terms denoting microorganisms or higher eucaryotic cell lines cultured as unicellular entities refer to cells which can be, or have been, used as recipients for recombinant vector or other transfer DNA, and include the original progeny of the original cell which has been transfected.

As used herein "replicon" means any genetic element, such as a plasmid, a chromosome or a virus, that behaves as an autonomous unit of polynucleotide replication within a cell. That is, it is capable of replication under its own control.

A "vector" is a replicon in which another polynucleotide segment is attached, such as to bring about the replication and/or expression of the attached segment.

The term "control sequence refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, MRNA, cDNA, and recombinant polynucleotide sequences.

The term "immunologically identifiable with/as" refers to the presence of epitope(s) and polypeptide(s) which also are present in and are unique to the designated polypeptide(s), usually HGBV proteins. Immunological identity may be determined by antibody binding and/or competition in binding. These techniques are known to the routineer and also are described herein. The uniqueness of an epitope also can be determined by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

The term "individual" as used herein refers to vertebrates, particularly members of the mammalian species and includes but is not limited to domestic animals, sports animals, primates and humans; more particularly the term refers to tamarins and humans.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an HGBV epitope" means naturally occurring HGBV polypeptides or fragments thereof, as well as polypeptides prepared by other means, for example, chemical synthesis or the expression of the polypeptide in a recombinant organism.

The term "transformation" refers to the insertion of an exogenous polynucleotide into a host cell, irrespective of the method used for the insertion. For example, direct uptake, transduction, or f-mating are included. The exogenous polynucleotide may be maintained as a non-integrated vector, for example, a plasmid, or alternatively, may be integrated into the host genome.

"Treatment" refers to prophylaxis and/or therapy.

The term "plus strand" (or "+") as used herein denotes a nucleic acid that contains the sequence that encodes the polypeptide. The term "minus strand" (or "−") denotes a nucleic acid that contains a sequence that is complementary to that of the "plus" strand.

"Positive stranded genome" of a virus denotes that the genome, whether RNA or DNA, is single-stranded and encodes a viral polypeptide(s).

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens.

"Purified HGBV" refers to a preparation of HGBV which has been isolated from the cellular constituents with which the virus is normally associated, and from other types of viruses which may be present in the infected tissue. The techniques for isolating viruses are known to those skilled in the art and include, for example, centrifugation and affinity chromatography.

"PNA" denotes a "peptide nucleic analog" which may be utilized in a procedure such as an assay described herein to determine the presence of a target. PNAs are neutrally charged moieties which can be directed against RNA targets or DNA. PNA probes used in assays in place of, for example, the DNA probes of the present invention, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with such signal generating compounds as fluorescein, radionucleotides, chemiluminescent compounds, and the like. PNAs or other nucleic acid analogs such as morpholino compounds thus can be used in assay methods in place of DNA or RNA. Although assays are described herein utilizing DNA probes, it is within the scope of the routineer that PNAs or morpholino compounds can be substituted for RNA or DNA with appropriate changes if and as needed in assay reagents.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, Duracytes® (derivatized red blood cells, available from Abbott Laboratories, Abbott Park, Ill. and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing probes on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include but are not limited to natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen; synthetic polymers which may be prepared with suitably porous structures, such as vinyl polymers; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 227,272.

The "indicator reagent" comprises a "signal generating compound" (also termed a "label") which is capable of generating and generates a measurable signal detectable by external means conjugated (attached) to a specific binding member for HGBV. "Specific binding member" as used herein means a member of a specific binding pair. That is, two different molecules where one of the molecules through chemical or physical means specifically binds to the second molecule. In addition to being an antibody member of a specific binding pair for HGBV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. Furthermore, specific binding pairs can include members that are analogs of the original specific binding members, for example, an analyte-analog. An immunoreactive specific binding member can be an antibody or fragment thereof, an antigen or fragment thereof, or an antibody/antigen complex including those formed by recombinant DNA molecules that is capable of binding either to HGBV as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that direct labels may require additional components such as but not limited to substrates, triggering reagents, light, and the like to enable detection of the label. When indirect labels are used for detection, they are typically used in combination with a conjugate. A "conjugate" is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label.

The term "hapten", as used herein, refers to a partial antigen or non-protein binding member which is capable of binding to an antibody, but which is not capable of eliciting antibody formation unless coupled to a carrier protein. Examples of haptens include biotin, avidin, adamantine and carbazole.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances such as target nucleotide sequences, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a nucleotide target of RNA or DNA or of PNA, and the like.

Embodiments which utilize ion capture procedures for immobilizing an immobilizable reaction complex with a negatively charged polymer, described in co-pending U.S. patent application Ser. No. 150,278 corresponding to EP publication 0326100 and U.S. patent application Ser. No. 375,029 (EP publication no. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115.

Also, the methods of the present invention can be adapted for use in systems which utilize microparticle technology including in automated and semi-automated systems wherein the solid phase comprises a microparticle (magnetic or non-magnetic). Such systems include those described in pending U.S. patent applications Ser. No. 425,651 and 425,643, which correspond to published EPO applications Nos. EP 0 425 633 and EP 0 424 634, respectively.

The use of scanning probe microscopy (SPM) for analyte detection also is adaptable. In scanning probe microscopy, in particular in atomic force microscopy, the capture phase is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. Such a system is described in pending U. S. patent application Ser. No. 662,147.

It is contemplated and within the scope of the present invention that the HGBV group of viruses may be detectable in assays by use of a synthetic, recombinant or native probe that is common to all HGBV viruses. It also is within the scope of the present invention that different synthetic, recombinant or native probes identifying different epitopes from HGBV-A, HGBV-B, HGBV-C, or yet other HGBV viruses, can be used in assay formats. In the later case, these can be coated onto one solid phase, or each separate probe may be coated on separate solid phases, such as microparticles, and then combined to form a mixture of probes which can be later used in assays. Such variations of assay formats are known to those of ordinary skill in the art and are discussed hereinbelow.

The reagents and methods of the present invention are made possible by the provision of a family of closely related nucleotide sequences present in the plasma, serum or liver homogenate of an HGBV infected individual, either tamarin or human. This family of nucleotide sequences is not of human or tamarin origin, since it hybridizes to neither human nor tamarin genomic DNA from uninfected individuals, since nucleotides of this family of sequences are present only in liver (or liver homogenates), plasma or serum of individuals infected with HGBV, and since the sequence is not present in GenBank®. In addition, the family of sequences will show no significant identity at the nucleic acid level to sequences contained within the HAV, HBV, HCV, HDV and HEV genome, and low level identity, considered not significant, as translation products. Infectious sera, plasma or liver homogenates from HGBV infected humans contain these polynucleotide sequences, whereas sera, plasma or liver homogenates from non-infected humans do not contain these sequences. Northern blot analysis of infected liver with some of these polynucleotide sequences demonstrate that they are derived from a large RNA transcript similar in size to a viral genome. Sera, plasma or liver homogenates from HGBV-infected humans contain antibodies which bind to this polypeptide, whereas sera, plasma or liver homogenates from non-infected humans do not contain antibodies to this polypeptide; these antibodies are induced in individuals following acute non-A, non-B, non-C, non-D and non-E hepatitis infection. By these criteria, it is believed that the sequence is a viral sequence, wherein the virus causes or is associated with non-A, non-B, non-C, non-D and non-E hepatitis.

The availability of this family of nucleic acid sequences permits the construction of DNA probes and polypeptides useful in diagnosing non-A, non-B, non-C, non-D, non-E hepatitis due to HGBV infections, and in screening blood donors, donated blood, blood products and individuals for infection. For example, from the sequence it is possible to synthesize DNA oligomers of about eight to ten nucleotides, or larger, which are useful as hybridization probes or PCR primers to detect the presence of the viral genome in, for example, sera of subjects suspected of harboring the virus, or for screening donated blood for the presence of the virus. The family of nucleic acid sequences also allows the design and production of HGBV specific polypeptides which are useful as diagnostic reagents for the presence of antibodies raised during infection with HGBV. Antibodies to purified polypeptides derived from the nucleic acid sequences may also be used to detect viral antigens in infected individuals and in blood. These nucleic acid sequences also enable the design and production of polypeptides which may be used as vaccines against HGBV, and also for the production of antibodies, which then may be used for protection of the disease, and/or for therapy of HGBV infected individuals.

Using determined portions of the isolated HGBV nucleic acid sequences as a basis, oligomers of approximately eight nucleotides or more can be prepared, either by excision or synthetically, which hybridize with the HGBV genome and are useful in identification of the viral agent(s), further characterization of the viral genome, as well as in detection of the virus(es) in diseased individuals. The natural or derived probes for HGBV polynucleotides are a length which allows the detection of unique viral sequences by hybridization. While six to eight nucleotides may be a workable length, sequences of ten to twelve nucleotides are preferred, and those of about 20 nucleotides may be most preferred. These sequences preferably will derive from regions which lack heterogeneity. These probes can be prepared using routine, standard methods including automated oligonucleotide synthetic methods. A complement of any unique portion of the HGBV genome will be satisfactory. Complete complementarity is desirable for use as probes, although it may be unnecessary as the length of the fragment is increased.

When used as diagnostic reagents, the test sample to be analyzed, such as blood or serum, may be treated such as to extract the nucleic acids contained therein. The resulting nucleic acid from the sample may be subjected to gel electrophoresis or other size separation techniques; or, the nucleic acid sample may be dot-blotted without size separation. The probes then are labeled. Suitable labels and methods for attaching labels to probes are known in the art, and include but are not limited to radioactive labels incorporated by nick translation or kinasing, biotin, fluorescent and chemiluminescent probes. Examples of many of these labels are disclosed herein. The nucleic acids extracted from the sample then are treated with the labeled probe under hybridization conditions of suitable stringencies.

The probes can be made completely complementary to the HGBV genome. Therefore, usually high stringency conditions are desirable in order to prevent false positives. However, conditions of high stringency should be used only if the probes are complementary to regions of the HGBV genome which lack heterogeneity. The stringency of hybridization is determined by a number of factors during the washing procedure, including temperature, ionic strength, length of time and concentration of formamide. See, for example, J. Sambrook (supra). Hybridization can be carried out by a number of various techniques. Amplification can be performed, for example, by Ligase Chain Reaction (LCR), Polymerase Chain Reaction (PCR), Q-beta replicase, NASBA, etc.

It is contemplated that the HGBV genome sequences may be present in serum of infected individuals at relatively low levels, for example, approximately $10^2$–$10^3$ sequences per ml. This level may require that amplification techniques such as the LCR or the PCR be used in hybridization assays. Such techniques are known in the art. For example, the "Bio-Bridge" system uses terminal deoxynucleotide transferase to add unmodified 3'-poly-dT-tails to a nucleic acid probe (Enzo Biochem. Corp.). The poly dt-tailed probe is hybridized to the target nucleotide sequence, and then to a biotin-modified poly-A. Also, in EP 124221 there is described a DNA hybridization assay wherein the analyte is annealed to a single-stranded DNA probe that is complementary to an enzyme-labeled oligonucleotide, and the resulting tailed duplex is hybridized to an enzyme-labeled oligonucleotide. EP 204510 describes a DNA hybridization assay in which analyte DNA is contacted with a probe that has a tail, such as a poly-dT-tail, an amplifier strand that has a sequence that hybridizes to the tail of the probe, such as a poly-A sequence, and which is capable of binding a plurality of labeled strands. The technique first may involve amplification of the target HGBV sequences in sera to approximately $10^6$ sequences/ml. This may be accomplished by following the methods described by Saiki et al., *Nature* 324:163 (1986). The amplified sequence(s) then may be detected using a hybridization assay such as those known in the art. The probes can be packaged in diagnostic kits which include the probe nucleic acid sequence which sequence may be labeled; alternatively, the probe may be unlabeled and the ingredients for labeling could be included with the kit. The kit also may contain other suitably packaged reagents and materials needed or desirable for the particular hybridization protocol, for example, standards as well as instructions for performing the assay.

Other known amplification methods which can be utilized herein include but are not limited to the so-called "NASBA" or "3SR" technique taught in *PNAS USA* 87:1874–1878 (1990) and also discussed in *Nature*: 350 (No. 6313):91–92 (1991) and Q-beta replicase.

Fluorescence in situ hybridization ("FISH") also can be performed utilizing the reagents described herein. In situ hybridization involves taking morphologically intact tissues, cells or chromosomes through the nucleic acid hybridization process to demonstrate the presence of a particular piece of genetic information and its specific location within individual cells. Since it does not require homogenization of cells and extraction of the target sequence, it provides precise localization and distribution of a sequence in cell populations. In situ hybridization can identify the sequence of interest concentrated in the cells containing it. It also can identify the type and fraction of the cells in a heterogeneous cell population containing the sequence of interest. DNA and RNA can be detected with the same assay reagents. PNAs or morpholino compounds can be utilized in FISH methods to detect targets without the need for amplification. If increased signal is desired, multiple fluorophores can be used to increase signal and thus, sensitivity of the method. Various methods of FISH are known, including a one-step method using multiple oligonucleotides or the conventional multi-step method. It is within the scope of the present invention that these types of methods can be automated by various means including flow cytometry and image analysis.

Assays as described herein may utilize one viral antigen derived from any clone-containing HGBV nucleic acid sequence, or from the composite nucleic acid sequences derived from the HGBV nucleic acid sequences in these clones, or from the HGBV genome from which the nucleic acid sequences in these clones are derived. Or, the assay may use a combination of viral antigens derived from these sources. It also may use, for example, a monoclonal antibody directed against the same viral antigen, or polyclonal antibodies directed against different viral antigens. Assays can include but are not limited to those based on competition, direct reaction or sandwich-type assays. Assays may use solid phases or may be performed by immunoprecipitation or any other methods which do not utilize solid phases. Examples of assays which utilize labels as the signal generating compound and those labels are described herein. Signals also may be amplified by using biotin and avidin, enzyme labels or biotin anti-biotin systems, such as that described in pending U.S. patent application Ser. Nos. 608,849; 070,647; 418,981; and 687,785.

The HGBV nucleic acid sequences may be used to gain further information on the sequence of the HGBV genome and for identification and isolation of the HGBV agent. Thus, it is contemplated that this knowledge will aid in the characterization of HGBV including the nature of the HGBV genome, the structure of the viral particle and the nature of the antigens of which it is composed. This information, in turn, can lead to additional polynucleotide probes, polypeptides derived from the HGBV genome, and antibodies directed against HGBV epitopes which would be useful for the diagnosis and/or treatment of HGBV caused non-A, non-B, non-C, non-D and non-E hepatitis.

Synthetic oligonucleotides may be prepared using an automated oligonucleotide synthesizer such as that described by Warner, *DNA* 3:401 (1984). If desired, the synthetic strands may be labeled with $^{32}$P by treatment with polynucleotide kinase in the presence of $^{32}$P-ATP, using standard conditions for the reaction. DNA sequences including those isolated from genomic or cDNA libraries, may be modified by known methods which include site directed mutagenesis as described by Zoller, *Nucleic Acids Res.* 10:6487 (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions suitable for hybridization with the correct strand, but not with the unmodified sequence. The sequences which have been identified by hybridization are recovered and cloned.

Polymerase chain reaction (PCR) and ligase chain reaction (LCR) are techniques for amplifying any desired nucleic acid sequence (target) contained in a nucleic acid or mixture thereof. In PCR, a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to geometrically increase the number of target sequence molecules. PCR is disclosed in U.S. Pat. Nos. 4,683,195 and 4,683,202.

LCR is an alternate mechanism for target amplification. In LCR, two sense (first and second) probes and two antisense (third and fourth) probes are employed in excess over the target. The first probe hybridizes to a first segment of the target strand and the second probe hybridizes to a second segment of the target strand, the first and second segments being positioned so that the primary probes can be ligated into a fused product. Further, a third (secondary) probe can hybridize to a portion of the first probe and a fourth (secondary) probe can hybridize to a portion of the second probe in a similar ligatable fashion. If the target is initially double stranded, the secondary probes will also hybridize to the target complement in the first instance. Once the fused strand of sense and antisense probes are separated from the target strand, it will hybridize with the third and fourth probes which can be ligated to form a complementary, secondary fused product. The fused products are functionally equivalent to either the target or its complement. By repeated cycles of hybridization and ligation, amplification of the target sequence is achieved. This technique is described in EP-A-320,308, hereby incorporated by reference. Other aspects of LCR technique are disclosed in EP-A-439,182, which is incorporated herein by reference.

Oligonucleotides are provided which are useful for the detection of HGBV-C. These oligonucleotides detect isolates of HGBV-C but do not detect isolates of HGBV-A or HGBV-B. These primers are designated as SEQUENCE ID NO. 51, SEQUENCE ID NOS 53–57 and SEQUENCE ID NO 87. Other primers, designated as SEQUENCE ID NO. 27 through SEQUENCE ID NO 35, are useful for classifying genotypes of HGBV-C. As a result of studying nucleotide sequences of HGBV-C isolates, it has been found that these isolates can be divided into at least four genotypes based upon the nucleotide sequences located near the 5' end of the genome.

The primers are useful in amplification procedures described previously herein such as PCR. Other primers which can differentiate between the genotypes can be used in PCR, while other primers are useful in GAP LCR. These are described in the following examples. These primers thus provide a method of detecting HGBV-C genotypes.

As detailed hereinbelow, 5' end cDNA was obtained by reverse transcription with random hexamer primers, and the cDNA was amplified using other oligonucleotide primer(s)

as a sense and antisense primer(s) in a PCR reaction. In some cases, this PCR reaction was followed by amplification using other primers as sense and antisense primers in a second stage PCR. As shown hereinbelow, we classified 46 HGBV-C isolates obtained from 39 individuals into four genotypes. These genotypes exhibited a maximum sequence divergence of 17.4%.

The HGBV-C oligonucleotides described herein are useful in detecting HGBV-C nucleic acids in a test sample. The genotyping of HGBV-C isolates also will aid in prognostic studies as well as in prevention and treatment of the disease caused by HGBV-C in humans.

The present invention will now be described by way of examples, which are meant to illustrate, but not to limit, the spirit and scope of the invention.

EXAMPLES

Example 1. Detection of HGBV-C RNA

As described by us previously in U.S. Ser. No. 08/473,475 (previously incorporated herein by reference), the generation of HGBV-C-specific ELISAs has allowed the identification of immunopositive sera in each of several categories of human populations, including intravenous drug users, residents of West Africa, volunteer blood donors and individuals with or at risk for non-A-E hepatitis. Sera from these seropositive individuals were tested for HGBV-C viremia by the RT-PCR assays described briefly as follows, and several serum samples were found to be positive for HGBV-C viral RNA. RT-PCR was performed using degenerative NS3 oligonucleotide primers (SEQUENCE ID NOS. 88 and 89) in a single round of amplification employing a thermocycling protocol designed to amplify specific products with oligonucleotide primers that may contain base pair mismatches with the template to be amplified (Roux, Bio/Techniques 16:812–814 [1994]). Specifically, reactions were thermocycled 43 times (94° C., 20 sec; 55° C. decreasing 0.3° C./cycle, 30 sec; 72° C., 1 min) followed by 10 cycles (94° C., 20 sec; 40° C., 30 sec; 72° C., 1 min) with a final extension at 72° C. for 10 minutes. PCR products were separated by agarose gel electrophoresis, visualized by UV irradiation after direct staining of the nucleic acid with ethidium bromide, then hybridized to a radiolabeled probe for GB-C (SEQUENCE ID NO 26, from position 4245 to 4432) after Southern transfer to Hybond-N+ nylon filter (available from Amersham Life Sciences, Arlington Heights, Ill.). Testing by RT-PCR of additional seropositive individuals from each of the populations listed above demonstrated a correlation between antibody presence and detection of viral RNA. At that time, the PCR amplified products from 26 of these individuals were cloned into the vector pT7Blue and sequenced, following methods as described in the art. Alignment of these sequences, each derived from the highly conserved portion of the HGBV-C NS3 helicase gene (i.e. nucleotides 4272–4407 of HGBV-C, SEQUENCE ID NO. 26; 135 nucleotides in length), and subsequent phylogenetic analysis did not demonstrate a significant grouping of the sequences into subtypes (data not shown).

Phylogenetic analysis has been applied to the hepatitis C viruses and has demonstrated that the variability among HCV isolates delineated six equally divergent main subtypes of sequences. See, for example, Simmonds, P. et al., *J. Gen. Virol.* 74:2391–2399 (1993) and Simmonds, P. et al., *J. Gen. Virol.* 75:1053–1061] (1994). This analysis resulted in the establishment of a system of nomenclature for the hepatitis C viruses, as reported by Simmonds, P. et al. *Hepatology,* 19:1321–1324 (1994), where the isolates were classified into genotypes based upon the evolutionary distance between groups of sequences. In the case of HCV, infection with specific viral genotypes has been correlated with severity of disease and responsiveness to treatment with antiviral drugs such as interferon-2alpha. See, for example, Dawson, G., et al. "Recent developments in the molecular biology of the hepatitis viruses" in *Current Hepatology,* G. Gitnick (Ed)., St. Louis, Mo., Mosby (1995). To examine the possible correlation between severity of disease or treatment outcomes and infection with specific HGBV-C subtypes, it was first necessary to determine whether such subtypes existed. However, the data obtained at that time from analysis of the NS3 sequences had not demonstrated the presence of genotypes (as described herein); this was due to the limited amount of sequence data obtained from each isolate (i.e., only 135 nucleotides). Thus, in order to obtain sufficient data to accurately determine the phylogenetic relationships between HGBV-C isolates, experiments were conducted to amplify extended regions from the 5'-end of the HGBV-C genome of various HGBV-C isolates.

Sera from individuals previously shown to be RT-PCR positive for HGBV-C as described hereinabove were used as the source of HGBV-C viral RNA. Specifically, two oligonucleotide primers, SEQUENCE ID NO. 51 (ntrC-S1) and SEQUENCE ID NO 52 (G131-E1wb2), located near the 5'-terminus of the HGBV-C genome and near the N-terminus of the putative E1 gene, respectively, were utilized in the thermocycling protocol known in the art and previously described hereinabove, on serum-derived cDNA products generated as known in the art. In some experiments, other oligonucleotide primers (i.e., ntrC-S2 [SEQUENCE ID NO 53] combined with ntrC-4R [SEQUENCE ID NO 57] and ntrC-S1 [SEQUENCE ID NO 51] combined with ntrC-4R [SEQUENCE ID NO 57] derived from the 5' end of the HGBV-C genome were used in PCR experiments detailed herein to amplify smaller regions of the HGBV-C genome. Using these primers, 46 PCR products (SEQUENCE ID NOS 2 through 6, SEQUENCE ID NO 9 through 11, SEQUENCE ID NO 13 through 24 and SEQUENCE ID NO 60 through 86) (TABLE 1) were obtained from 39 individuals previously shown to be HGBV-C RNA positive: Four of these isolates were from individuals classified as indeterminate for the presence of antibodies to hepatitis C virus proteins, 21 of these isolates were from individuals from a region of West Africa where infection with other hepatitis viruses is endemic (this includes the corresponding sequence from the HGBV-C genome, SEQUENCE ID NO 26, in TABLE 1, hereinbelow), four of these isolates were from non A–E hepatitis patients, five of these isolates were from patients diagnosed with aplastic anemia, six of these isolates were from multiply transfused individuals, three of these isolates were from normal blood donors from the U.S., one of these isolates was from an intravenous drug user (IVDU) and two of these isolates were from two individuals from southeast Asia. These products were cloned into the bacterial plasmid pTVBlue and sequenced following procedures known in the art. The HGBV-C isolates obtained are listed in TABLE 1, including a description of the individual from which the isolates were obtained. In some cases multiple isolates obtained from a single source were sequence analyzed; specifically: SEQUENCE ID NOS 16, 20 and 84 were obtained from an individual diagnosed with aplastic anemia; SEQUENCE ID NOS 21 and 22 were obtained from a multiply transfused individual; SEQUENCE ID NOS 67 and 68, 69 and 70, 75 and 76 were obtained from three individuals from West Africa, respectively.

TABLE 1

HGBV-C Isolates

| SEQ ID # | Genotype | Description | SEQ ID # | Genotype | Description |
| --- | --- | --- | --- | --- | --- |
| 2 | 1 | West Africa | 64 | 1 | West Africa |
| 3 | 1 | West Africa | 65 | 1 | West Africa |
| 4 | 1 | West Africa | 66 | 1 | West Africa |
| 5 | 1 | West Africa | 67 | 1 | West Africa |
| 6 | 1 | West Africa | 68 | 1 | West Africa |
| 9 | 2 | HCV Indeterminate | 69 | 1 | West Africa |
| 10 | 2 | Aplastic Anemia | 70 | 1 | West Africa |
| 11 | 2 | Normal Donor | 71 | 1 | West Africa |
| 13 | 2 | Multiply Transfused | 72 | 1 | West Africa |
| 14 | 2 | HCV Indeterminate | 73 | 1 | West Africa |
| 15 | 2 | HCV Indeterminate | 74 | 1 | West Africa |
| 16 | 3 | Aplastic Anemia | 75 | 1 | West Africa |
| 17 | 3 | Non-A-thru-Non-E‡ | 76 | 1 | West Africa |
| 18 | 3 | Non-A-thru-Non-E‡ | 77 | 1 | West Africa |
| 19 | 3 | Non-A-thru-Non-E‡ | 78 | 4 | Southeast Asia |
| 20 | 3 | HCV Indeterminate | 79 | 2 | Non-A-thru-Non-E‡ |
| 21 | 3 | Multiply Transfused | 80 | 1 | West Africa |
| 22 | 3 | Multiply Transfused | 81 | 2 | Aplastic Anemia |
| 24 | 3 | Multiply Transfused | 82 | 3 | Normal Donor |
| 60 | 2 | Aplastic Anemia | 83 | 1 | West Africa |
| 61 | 2 | Multiply Transfused | 84 | 2 | Aplastic Anemia |
| 62 | 2 | Multiply Transfused | 85 | 2 | Intravenous Drug User |
| 63 | 4 | Southeast Asia | 86 | 2 | Non-A-thru-Non-E‡ |

Alignment of these sequences was made using the program PILEUP of the Wisconsin Sequence Analysis Package (Version 8) and is shown in FIG. 1A–FIG. 1F. Referring to FIG. 1A–1F, the consensus nucleotide at each position in the alignment was determined by the base that occurred most frequently at that position. The consensus line does not necessarily represent the consensus sequence of the "prototype" GB virus C isolate. The dashes (-) in FIG. 1A–1F represent bases identical to that shown on the consensus line which is indicated as "cons" in this FIGURE. Base deletions are indicated by periods (.) in this FIGURE. For each isolate, bases are shown only at those positions in the alignment that differ from the consensus. The sequence of the PCR primers used to amplify the isolates are not shown the alignment of this FIGURE. The phylogenetic relationship between these GB virus C sequences (isolates) was examined by calculating the evolutionary distance between the aligned nucleotide sequences using the DNADIST program of the PHYLIP package (version 3.5c, 1993) kindly provided by J. Felsenstein (see Felsenstein, J. *Cladistics* 5:164–166 [1989]). These computed distances were used for the construction of phylogenetic trees using the program FITCH. A tree providing a graphical representation of the distance between sequences was plotted using the program DRAWGRAM and is shown in FIG. 2. The "root" of the tree is arbitrarily assigned to the midpoint of the longest branch of the tree for clarity of display, however, the tree shown is unrooted; i.e. the ancestor common to all sequences in the tree has not been established.

The results of this analysis indicated that there are at lease four distinct genotypes of GB virus C isolates. The relatedness of these individual sequences is presented graphically in FIG. 2. Two of these groups, i.e., genotypes 1 and 4, are significantly distant from each other and the other two groups, i.e., genotypes 2 and 3. Up to this time, Genotype 1 isolates of HGBV-C have been found exclusively among individuals from West Africa and have included the original HGBV-C isolate. Sequences belonging to Genotypes 2 and 3 isolates have not demonstrated, to date, a specific geographic distribution. Complete clinical information regarding disease status or treatment regimes has not been available for all of these individuals from which sequences were obtained. Thus, it has not been currently possible to correlate disease severity with infecting HGBV- C genotype. Collection of clinical information is ongoing. Of interest, however, is the observations that some individuals may be infected with more than one genotype of HGBV-C, since one patient diagnosed with aplastic anemia has been found to be infected with HGBV-C genotypes 2 and 3 (SEQUENCE ID NOS 12, 16 AND 60).

A large amount of sequence variation was found to be present in the various HGBV-C isolates from both the NS3 and 5'-terminal region. Although highly sensitive, PCR based assays for viral nucleic acids are dependent on the sequence match between oligonucleotide primers and the viral template. Therefore, because the PCR primers which were utilized to amplify sequences from the NS3 region and the 5'-terminal portion (GBV-C [SEQUENCE ID NO 51]-E1wb2 [SEQUENCE ID NO 52]) of the genome were located in regions that were not well conserved in all isolates, not all HGBV-C viremic samples tested may have been detected by the RT-PCR assays employed here. It was hypothesized that utilization of PCR primers from a highly conserved region of the HGBV-C genome, as have been found in the HCV 5' untranslated region [Cha, et al. *J. Clin. Microbiol.* 29:2528–2534 (1991)], should allow more accurate detection of HGBV-C viremic samples. Thus, examination of the aligned sequences presented in FIG. 1 generated from all 46 isolates demonstrated the presence of several regions of highly conserved nucleotide sequences among all the isolates. Primers prepared from these highly conserved regions of HGBV-C, ntrC-S2 (SEQUENCE ID NO 53), ntrC-A1 (SEQUENCE ID NO 54), ntrC-A2 (SEQUENCE ID NO 55), ntrC-3F (SEQUENCE ID NO 56), and ntrC-4R (SEQUENCE ID NO 57) were developed to examine the sensitivity and specificity of these universal HGBV-C primers versus the degenerate primers from the HGBV-C helicase gene. The primers ntrC-S1/ntrC-a1 (SEQUENCE ID NO 51 /SEQUENCE ID NO 54) and ntrC-S2/ntrC-a2 (SEQUENCE ID NO 53/SEQUENCE ID NO 55) were used in independent PCRs or in combination in a nested PCR experiment. The primers ntrC-3F/ntrC-4R (SEQUENCE ID NO 56/SEQUENCE ID NO 57) were used in combination in separate PCRs. These PCR amplification procedures, well-known to those of ordinary skill in the art, were as follows.

Briefly, the first round amplification was performed on serum cDNA products generated as described earlier, using 2 mM MgCl$_2$ and 1 μM primers (both sense and antisense), as follows. Reactions were subjected to 35–40 cycles of denaturation-annealing-extension (94° C., 20 sec; 55° C., 30 sec; 72° C., 45 sec) followed by a 10 min extension at 72° C. Completed reactions were held at 4° C. A second round of amplification performed as either a fully nested or a hemi-nested reaction, if necessary, was performed utilizing 2 mM MgCl$_2$, 1 μM sense and antisense primers and 4% of the first PCR products as template. The second round of amplification employed a thermocycling protocol identical that utilized in the first round of PCR. PCR products were separated by agarose gel electrophoresis and visualized by UV irradiation after direct staining of the nucleic acid with ethidium bromide. Unless a nested PCR reaction was performed, the products of a single round of PCR amplification were transferred to Hybond-N+ nylon filter and then hybridized to a radiolabeled probe for HGBV-C. Results obtained from these experiments confirmed the presence of HGBV-C RNA in 38 out of 39 individuals whose sera had previously tested positive for HGBV-C RNA by using the helicase region primers as stated hereinabove. We hypothesized that the single individual whose serum tested negative with the HGBV-C universal 5'-end primers may have originally been detected positive with the NS3 primers due to contamination of the serum sample with amplicon derived from another sample or with HGBV-C RNA-positive sera from another individual. However, primer pairs derived from highly conserved regions of these HGBV-C isolates have been shown to be useful as a method to test for or and/or confirm HGBV-C viremia.

In order to determine which oligonucleotide primers derived from highly conserved regions within the 5'-end of the HGBV-C genome would be the most useful for detecting HGBV-C RNA, RT-PCR experiments were conducted in which various sense primers (ntrC-S1 [SEQUENCE ID NO 51], ntrC-3F [SEQUENCE ID NO 56), ntrC-A1 [SEQUENCE ID NO 54], ntrC-A2 [SEQUENCE ID NO 55], ntrC-4R [SEQUENCE ID NO 57], ntrC-5R [SEQUENCE ID NO 87]). Human sera obtained from 12 commercial blood donors that had tested positive for GBV-C RNA with PCR primers derived from the NS3 helicase region (using SEQUENCE ID NOS 88 and 89 and amplification procedures disclosed hereinabove, data not shown) were retested by using eleven difference combinations of HGBV-C 5'-end sense/antisense primers. Briefly, amplification was performed on serum cDNA products generated as described hereinabove, using 2 mM $MgCl_2$ and 1 $\mu$M sense and antisense primers. PCR reactions utilized 40 cycles of denaturation-annealing-extension (94° C., 20 sec.; 55° C., 30 sec.; 72° C., 45 sec.) followed by a ten minute extension at 72° C. Completed reactions were held at 4° C. Amplification reactions utilized only 40% of the amount of cDNA used in the initial testing of these samples with NS3 degenerate primers. Thus, in order to compare the usefulness of the 5'-end derived primers with the NS3 degenerate primers, the samples were retested in parallel for HGBV-C RNA using primers derived from the NS3 helicase gene (SEQUENCE ID NOS 88 and 89) following the methods as described hereinbelow. Amplification with NS3 degenerate HGBV-C primers was conducted using a thermocycling protocol designed to amplify DNA sequences that may contain base pair mismatches between the template and the primer(s) as described by Roux, Bio/Techniques 16:812–814 (1994)]. Specifically, reactions were thermocycled 43 times (94° C., 20 sec; 55° C. decreasing 0.3° C./cycle, 30 sec; 72° C., 1 min) followed by 10 cycles (94° C., 20 sec; 40° C., 30 sec; 72° C., 1 min) with a final extension at 72° C. for 10 minutes. PCR products were separated by agarose gel electrophoresis and visualized by UV irradiation after direct staining of the nucleic acid with ethidium bromide. The nucleic acids then were transferred by Hybond-N+nylon filters (available from Amersham Life Sciences, Arlington Heights, Ill.) and then hybridized to the appropriate radiolabeled probe for HGBV-C (SEQUENCE ID NO 26, positions 13 to 631).

Results of these experiments are summarized in TABLES 2A and 2B. As the results demonstrate, the primer pair ntrC-S1/ntrC-2A (SEQUENCE ID NO 51/SEQUENCE ID NO 55) detected HGBV-C RNA in all 11/12 specimens as determined by ethidium bromide staining (TABLE 2A) and 12/12 specimens as determined by southern blot analysis (TABLE 2B). In contrast, ntr-C-3F/ntrC-4R (SEQUENCE ID NO 56/SEQUENCE ID NO 57) detected only 4/12 specimens as determined by ethidium bromide staining and 7/12 specimens as determined by southern hybridization. In addition, the NS3-derived HGBV-C degenerate primers (SEQUENCE ID NO 88 and SEQUENCE ID NO 89) detected RNA in 7/12 specimens as determined by ethidium bromide staining and 8/12 specimens by southern analysis. These data indicate that some HGBV-C 5'-end primers pairs may be more sensitive than others for detecting HGBV-C viremia, even though all 5'-end primers are derived from regions exhibiting a high degree of nucleotide sequence conservation among all HGBV-C isolates.

In addition, under the conditions utilized, the HGBV-C NS3 helicase derived PCR primers may not be as sensitive as the primers derived from the 5' end of the genome for the detection of HGBV-C nucleic acids. TABLES 2A and 2B indicate primer pairs wherein S1 corresponds to SEQUENCE ID NO 51, S2 corresponds to SEQUENCE ID NO 53, 5R corresponds to SEQUENCE ID NO 87, 3F corresponds to SEQUENCE ID NO 56, A1 corresponds to SEQUENCE ID NO 54, A2 corresponds to SEQUENCE ID NO 55, 4R corresponds to SEQUENCE ID NO 57 and NS3 corresponds to SEQUENCE ID NO 88 and 89.

TABLE 2A

Summary of GBV-C Primer Pair Testing: Ethidium Bromide Results

| Sample | S1/5R | S2/5R | 3F/5R | 3F/4R | S1/A1 | NS3 | S1/A2 | S1/4R | 3F/A1 | 3F/A2 | S2/A2 | S2/A1 |
|---|---|---|---|---|---|---|---|---|---|---|---|---|
| 1 | + | + | + | + | + | + | + | + | + | + | + | + |
| 2 | + | + | + | + | + | + | + | + | + | + | + | + |
| 3 | + | – | + | + | + | + | + | + | + | + | + | + |
| 4 | + | – | – | – | + | – | + | – | + | + | + | +/– |
| 5 | – | – | – | – | – | – | + | – | – | – | – | +/– |
| 6 | + | + | + | – | + | + | + | + | + | + | + | + |
| 7 | – | – | – | – | – | – | + | – | – | – | – | – |
| 8 | + | – | +/– | – | + | + | + | + | + | + | + | + |
| 9 | – | – | – | – | + | – | + | – | nd‡ | – | nd‡ | +/– |
| 10 | + | + | + | + | + | + | + | + | + | + | + | +/– |
| 11 | – | – | – | – | + | – | + | +/– | nd‡ | + | + | + |
| 12 | +/– | – | – | – | + | – | – | – | – | – | – | – |
| Totals | 8 | 4 | 6 | 4 | 10 | 7 | 11 | 7 | 7 | 8 | 8 | 10 |

‡nd means not determined.

TABLE 2B

Summary of GBV-C Primer Pair Testing: Southern Blotting Results

| | Primer Pairs | | | | | | | | | | | |
|---|---|---|---|---|---|---|---|---|---|---|---|---|
| Sample | S1/5R | S2/5R | 3F/5R | 3F/4R | S1/A1 | NS3 | S1/A2 | S1/4R | 3F/A1 | 3F/A2 | S2/A2 | S2/A1 |
| 1 | + | + | + | + | + | + | + | + | + | + | + | + |
| 2 | + | + | + | + | + | + | + | + | + | + | + | + |
| 3 | + | + | + | + | + | + | + | + | + | + | + | + |
| 4 | + | − | − | − | + | + | + | + | + | + | + | + |
| 5 | − | − | − | − | − | − | + | − | +/− | − | − | + |
| 6 | + | + | + | +/− | + | + | + | + | + | + | + | + |
| 7 | − | − | − | +/− | − | − | + | − | − | +/− | − | − |
| 8 | + | + | +/− | − | + | + | + | + | + | + | + | + |
| 9 | − | − | − | +/− | + | − | + | +/− | nd‡ | − | nd‡ | + |
| 10 | + | + | + | + | + | + | + | + | + | + | + | + |
| 11 | − | +/− | − | − | + | +/− | + | + | nd‡ | + | + | + |
| 12 | +/− | − | − | − | + | − | + | − | − | +/− | +/− | +/− |
| Totals | 8 | 7 | 6 | 7 | 10 | 8 | 12 | 9 | 8 | 10 | 9 | 11 |

‡nd means not determined.

Example 2. Differential detection of HGBV-C Genotypes 1, 2 and 3

Oligonucleotide primers are used in amplification reactions to differentially detect HGBV-C genotype 1 or 2 or 3, as follows. These primers, HGBV-C-1a-s1 (SEQUENCE ID NO 28), HGBV-C-1a-s2 (SEQUENCE ID NO 32), HGBV-C-1a-a1 (SEQUENCE ID NO 27), HGBV-C-1a-a2 (SEQUENCE ID NO 31), HGBV-C-1bc-s1 (SEQUENCE ID NO 29), HGBV-C-1bc-s2 (SEQUENCE ID NO 33), HGBV-C-1bc-a1 (SEQUENCE ID NO 30), HGBV-C-1bc-a2 (SEQUENCE ID NO 34), can be used in amplification reactions where each primer is paired with one of the sense or antisense primers listed above in Example 1 and following the PCR protocols presented in Example 1. Primers listed above with a "1a" designation are selective for HGBV-C genotype 1; primers with a "1b" designation are selective for HGBV-C genotype 2; primers with a "1c" designation are selective for HGBV-C genotype 3. The genotype of the particular HGBV-C isolate is determined by the presence or absence of a PCR amplification product of the predicted size as visualized by agarose gel electrophoresis and ethidium bromide staining. In addition, genotypes can be identified by determining the nucleic acid sequence of the PCR amplification product produced using one of the HGBV-C primer pairs. The determined sequence is then compared with the sequence from the homologous region of other HGBV-C isolates. This is accomplished by sequence alignment and subsequent phylogenetic analysis using methods known in the art.

Example 3: GAP LCR Detection of HGBV-C Genotypes

We have observed that some regions within the HGBV-C sequences are significantly different among the isolates. These sequences were utilized for the construction of oligonucleotide primers that can be used in a GAP-LCR assay to distinguish between members of HGBV-C genotypes 1, 2 or 3.

Briefly, double-gap LCR is performed as follows and as detailed in U.S. Pat. No. 5, 427,930, previously incorporated herein by reference. Double gaps are represented herein as "DG p, q" where in "p" is the number of bases in the gap of one strand, and "q" is the number of bases in the gap of the other strand. Thus, a preferred double gap embodiment has two bases missing from each of the two probes whose 5' end participates in the ligation, and is designated as DG2,2. In this preferred embodiment, the 3' ends of the other two probes do not overlap; rather, they terminate at the same point on the target strand (and its complement). The procedure is outlined as follows. Double gap LCR is performed for 30–50 cycles consisting of a 65 second incubation at 85° C. and a 65 second incubation at 50° C. The oligonucleotides used are presented hereinbelow as SEQUENCE ID NOS. 35 through 50, and are specific for the 5' end of HGBV-C. Reactions are run in a buffer containing 50 mM EPPS pH 7.8, 100 mM KCl, 10 mM $MgCl_2$, 1 mM DTT, 10 mM $NH_4Cl$, 100 μm NAD, 10 μg/ml BSA, $5 \times 10^{11}$ each oligonucleotide listed hereinabove, 1 μm 2'-deoxyguanosine 5'triphosphate, 0.5 units Thermus DNA polymerase (Molecular Biology Resources, Inc., "MBR"), and 3400 units *Thermus thermohilus* DNA ligase. Reaction volume is 50 μl and each reaction is overlaid with 25 μl of mineral oil prior to cycling.

Following amplification, reactions are diluted 1:1 with $IM_X$® diluent buffer (available from Abbott Laboratories, Abbott Park, Ill.), or other suitable buffer. The LCR amplification products are detected via a sandwich immnunoassay performed using the Abbott $IM_X$® automated immunoassay system.

Example 4. Internal ribosome entry site in 5' NTR of GBV-B

Several positive strand RNA viruses, such as picornaviruses and pestiviruses, possess large 5' nontranslated regions (NTRs). These large NTRs control the initiation of cap-independent translation by functioning as internal ribosome entry sites (IRESs) (Pelletier and Sonenberg, *Nature* (London) 334:320–325). The IRES is thought to form a specific RNA structure which allows ribosomes to enter and begin translation of an RNA without using the cellular machinery required for cap-dependent translation initiation. The large 5' NTR of HCV has been shown to possess an IRES (Wang et al. *J. Virol.* 67:3338–3344, 1993). Due to the high level of sequence conservation between the 5' NTRs of GBV-B and HCV, it was reasoned that GBV-B may also contain an IRES.

To test for IRES function in GB V-B, the 5' NTR of this virus was used to replace the 5' NTR of hepatitis A virus (HAV) in the pLUC-HAV-CAT plasmid described by Whetter et al. (*J. Virol.* 68:5253–5263, 1994). The 5' NTR of GBV-B was amplified from a plasmid clone using SEQUENCE ID NO. 58 (UTR-B.1) and SEQUENCE ID. NO. 59 (NTR-B-a1) as primers Briefly, a 50 μl PCR was set up using a Perkin-Elmer PCR kit as described by the manufacturer with 1 μM primers, 2 mM $MgCl_2$ an d approximately 10 ng of plasmid. This reaction was amplified for 20 cycles (94° C., 20 sec; 55° C., 30 sec; 72° C., 30 sec) followed by a final extension at 72° C. for 10 min. The completed reaction then was held at 4° C. This product was extracted with phenol:chloroform and precipitated as described in the art. The 3' terminal adenosine residues added by the AmpliTaq® polymerase were removed from this product by incubation with T4 DNA polymerase and deoxynucleotide triphosphates as described (Sambrook et al., *Molecular Cloning: A Laboratory Manual*, Cold Spring Harbor Press, 1989). After heat inactivation, the product was digested with Xba I and gel purified as described in the art. The purified product was ligated to pHAV-CAT1 (Whetter et al. *J. Virol.* 68:5253–5263, 1994) that had been cut with HindIII, end-filled with Klenow polymerase and deoxynucleotide triphosphates, heat-inactivated, digested with Xba I, treated with bacterial alkaline phosphatase, extracted with phenol:chloroform, and precipitated as described in the art. The constructed plasmid, pGBB-CAT1, was digested with Sac I, blunt-ended with T4 DNA polymerase and deoxynucleotide triphosphates, heat-inactivated, and digested with Not I as described in the art. The 1.3 kbp product from these reactions was gel purified and cloned into pLUC-HAV-CAT (Whetter et al. *J. Virol.* 68:5253–5263, 1994) that had been digested with HindIII, end-filled with Klenow polymerase and deoxynucleotide triphosphates, heat-inactivated, digested with Not I, treated with bacterial alkaline phosphatase, extracted with phenol:chloroform, and precipitated as described in the art. The resultant plasmid, pLUC-GBB-CAT was used in in vitro transcription-translation experiments to test for an IRES function.

An in vitro transcription-translation assay was performed using the TNT™ T7 coupled reticulocyte lysate system from Promega (Madison, Wisc.) as described by the manufacturer. The plasmids tested were pLUC-GBB-CAT (described above), pLUC-HAV-CAT (positive control from Whetter et al. *J. Virol.* 68:5253–5263, 1994), and pLUC-Δ355–532 (negative control from Whetter et al. *J. Virol.* 68:5253–5263, 1994). The products (labeled with $^{35}$S-methionine) were run on a 10% Laemmli gel as described in the art. The gel was fixed in 10% methanol, 20% acetic acid for 10 minutes, dried down and exposed to a PhosphoImager® screen (Molecular Dynamics, Sunnyvale, Calif.). The products were visualized with the PhosphoImager® (data not shown).

All three reactions contained a band consistent with the size expected for luciferase (the LUC gene in the plasmid). LUC expression, which is a measure of the level of translation that initiates from the 5' end of the mRNA, appeared to be equivalent in the three reactions. Thus, equivalent amounts of RNA templates were present in a translatable form in these three reactions. The pLUC-HAV-CAT and the pLUC-GBB-CAT reactions also had a band consistent with the size expected for chloramphenicol acetyltransferase (the CAT gene in the plasmid). This band is not seen in the pLUC-Δ355–532 negative control. CAT expression measures the level of internal translation initiation. Approximately equivalent levels of CAT expression are found in pLUC-HAV-CAT and pLUC-GBB-CAT-programmed lysates. Because translation of the CAT gene requires the existence of an IRES in this plasmid construct, the 5' NTR of GBV-B must be providing this function. Therefore, similar to HCV, GBV-B's 5'NTR contains an IRES. Further studies of these plasmids, both in vitro and in vivo are ongoing to better characterize the IRES in GBV-B.

The present invention is intended to be limited only by the appended claims.

We claim:

1. A composition of matter comprising an oligonucleotide consisting of SEQ ID NO: 51 and complements thereof.

2. A composition of matter comprising an oligonucleotide consisting of SEQ ID NO: 53 and complements thereof.

3. A composition of matter comprising an oligonucleotide consisting of SEQ ID NO: 54 and complements thereof.

4. A composition of matter comprising an oligonucleotide consisting of SEQ ID NO: 55 and complements thereof.

5. A composition of matter comprising an oligonucleotide consisting of SEQ ID NO: 56 and complements thereof.

6. A composition of matter comprising an oligonucleotide consisting of SEQ ID NO: 57 and complements thereof.

7. A composition of matter comprising an oligonucleotide consisting of SEQ ID NO: 87 and complements thereof.

8. A method of detecting target HGBV-C nucleotide in a test sample, comprising:
   (a) contacting the test sample with at least one HGBV-C specific oligonucleotide selected from the group consisting of SEQ ID NO:51, SEQ ID NO:53, SEQ ID NO:54, SEQ ID NO:55, SEQ ID NO:56, SEQ ID NO:57, SEQ ID NO:87, and complements thereof; and
   (b) detecting the presence of the target HGBV nucleotide in the test sample.

9. The method of claim 8 wherein the HGBV-C specific oligonucleotide is selected from the group consisting of SEQ ID NO: 2, SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 13, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, and SEQ ID NO: 86, and complements thereof.

10. A method of detecting target HGBV-C nucleotide in a test sample, comprising:
    a. contacting the test sample with at least one HGBV-C specific oligonucleotide selected from the group consisting of SEQ ID NO: 51, SEQ ID NO: 53, SEQ ID NO: 54, SEQ ID NO: 55, SEQ ID NO: 56, SEQ ID NO: 57, SEQ ID NO: 87, and complements thereof; and
    b. detecting the presence of the target HGBV-C nucleotide in the test sample.

11. The method of claim 10 wherein the target HGBV-C nucleotide is attached to a solid phase.

12. A method for amplifying the 5' NTR cDNA of hepatitis GB virus (HGBV) in a test sample, the method comprising:
    (a) performing reverse transcription by contacting the test sample with at least one random primer to obtain cDNA;
    (b) amplifying the cDNA obtained from step (a) by using HGBV specific oligonucleotide primers as sense and antisense primers in a first-stage PCR to obtain amplified cDNA wherein the sense primer is selected from the group consisting of SEQ ID NO: 51, SEQ ID NO: 53, and SEQ ID NO: 56, and the antisense primer is selected from the group consisting of SEQ ID NO: 54, SEQ ID NO: 55, SEQ ID NO: 57, and SEQ ID NO: 87;
    (c) detecting the presence of the amplicon in the test sample.

13. The method of claim 12 wherein step (b) is performed by the polymerase chain reaction.

14. The method of claim 12 wherein the test sample is attached to a solid phase.

15. The method of claim 12, wherein step (c) further comprises utilizing a detectable label capable of generating a measurable signal.

16. The method of claim 12, wherein the detectable label is attached to a solid phase.

17. A method of detecting target HGBV-C in a test sample suspected of containing the target, comprising:
    (a) performing reverse transcription by contacting the test sample with at least one primer selected from the group consisting of SEQ ID NO: 54, SEQ ID NO: 55, and SEQ ID NO: 57, and SEQ ID NO: 87 to obtain cDNA;
    (b) contacting the test sample with at least one HGBV-C specific oligonucleotides selected from the group consisting of SEQ ID NO: 51, SEQ ID NO: 53, SEQ ID NO: 56 as a sense primer, and with at least one HGBV-C specific oligonucleotide selected from the group consisting of SEQ ID NO: 54, SEQ ID NO: 55, SEQ ID NO: 57, and SEQ ID NO 87 as an antisense primer, and amplifying same; and
    (c) detecting the HGBV target in the test sample.

18. The method of claim 17, wherein the amplification of step (a) is performed by the polymerase chain reaction.

19. The method of claim 17, wherein the test sample is attached to a solid phase.

20. The method of claim 17, wherein step (c) further comprises utilizing a detectable label capable of generating a measurable signal.

21. The method of claim 20, wherein the detectable label is attached to a solid phase.

22. An HGBV-C oligonucleotide useful as a primer for the GAP Ligase Chain Reaction, wherein the HGBV-C oligonucleotide is selected from the group consisting of SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 43, SEQ ID NO: 44, SEQ ID NO: 45, SEQ ID NO: 46, SEQ ID NO: 47, SEQ ID NO: 48, SEQ ID NO: 49 and SEQ ID NO: 50, and complements thereof.

23. A test kit useful for detecting target HGBV-C nucleotide in a test sample, comprising a container containing at least one HGBV-C specific oligonucleotide selected from the group consisting of SEQ ID NO: 51, SEQ ID NO: 53, SEQ ID NO: 54, SEQ ID NO: 55, SEQ ID NO: 56, SEQ ID NO: 57, SEQ ID NO: 87, and complements thereof.

* * * * *

SEQUENCE LISTING ( 1 ) GENERAL INFORMATION:

( i i i ) NUMBER OF SEQUENCES: 89

( 2 ) INFORMATION FOR SEQ ID NO:1:

( i ) SEQUENCE CHARACTERISTICS:
( A ) LENGTH: 589 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
ACCGACGCCT ATCAAAATAG ACGTGATGGC CCCGCGCCGA ACTGGCGACC GGCCAAAAGG    60
TGGTGGATGG GTGATGACAG GGTTGGTAGG TCGTAAATCC CGGTCATCCT GGTAGCCACT   120
ATAGGTGGGT CTTAAAGGGA GGCTACGGTC CCTCTCGCGC TTACGGAGAG AAAGCGCACG   180
GTTCACAGGT GTTGGCCCTA CCGGTGTAAT AAGGGCCCGG CGCTAGGCAC GCCGTTAAAC   240
CGAGACCGTT ACCCTCCTGG GCAAACGACG CCCACGTACG GCCCACGTCG CCCTTCAATG   300
TCTCTCTTGA CCAATAGGCA ATGCCGGCGA GTTGACAAGG GCCAGTGGGG GCCGGCGGAC   360
AGGGGAAGGA CCCCTGTCGC TGCCCTTCCC GGAGGGACGG GAAATGCATG GGGCCACCCA   420
```

```
GCTCCGCGGC  GGCCTACAGC  CGGGGTAGCC  CAAGAACCTT  CGGGTGAGGG  CGGGTGGCAT      480

TTCTTTTCCT  ATACCAATCA  YGGCAGTCCT  TCTGCTCTTA  CTCGTTGTGG  AGGCCGGGGC      540

CATYCTGGCC  CCGGCCACCC  ATGCTTGTAG  CGCTAAAGGG  CAATATTTC                   589
```

( 2 ) INFORMATION FOR SEQ ID NO:2:

( i ) SEQUENCE CHARACTERISTICS:
        ( A ) LENGTH: 589 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
ACCGACGCCT  ATCAAAGTAG  ACGTGATGGC  CCCGCGCCAA  ACTGGCGACC  GGCCAAAAGG       60

TGGTGGATGG  GTGATGACAG  GGTTGGTAGG  TCGTAAATCC  CGGTCATCCT  GGTAGCCACT      120

ATAGGTGGGT  CTTAAAGGGA  GGCTACGGTC  CCTCTCGCGC  TTATGGAGAG  AAAGCGCACG      180

GTCCACAGGT  GTTGGCCCTA  CCGGTGTAAT  AAGGGCCCGG  CGCTAGGCAC  GCCGTTAAAC      240

CGAGACCGTT  ACCCCTCTGG  GCAAACGACG  CCCACGTACG  GCCCACGTCG  CCCTTCAATG      300

TCTCTCTTGA  CCAATAGGCA  ATGCCGGCGA  GTTGACAAGG  GCCAGTGGGG  GCCGGGCGGT      360

GGGGGAAGGA  CCCCCACCGC  TGCCCTTCCC  GAGGGGCGG   GAAATGCATG  GGGCCACCCA      420

GCTCCGCGGC  GGCCTACAGC  CGGGGTAGTC  CAAGAACCTT  CGGGTGAGGA  CGGGTGGCAT      480

TTCTTTCCTT  ATACCGATCA  TGGCAGTCTT  TCTGCTCTTA  CTCGTGGTGG  AGGCCGGGGC      540

CATTCTGGCC  CCGGCCACAC  ATGCTTGTAG  TGCTAAAGGG  CAATACTTC                   589
```

( 2 ) INFORMATION FOR SEQ ID NO:3:

( i ) SEQUENCE CHARACTERISTICS:
        ( A ) LENGTH: 591 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
ACCGACGCCT  ATCGAAGTAG  ACGTGATGGC  CCCGCGCCGA  ACCGGCGACC  GGCCAAAAGG       60

TGGTGGATGG  GTGATGCCAG  GGTTGGTAGG  TCGTAAATCC  CGGTCATCTT  GGTAGCCACT      120

ATAGGTGGGT  CTTAAGGGGA  GGTAACGGTC  CCTCTCGCGC  TTGTGGAGAG  AAAGCGCACG      180

GTCCACAGGT  GTTGGTCCTA  CCGGTGTGAA  TAAGGACCCG  GCGTTAGGCT  CGCCGTTAAA      240

CCGAGCCCGT  TAACCCCCTG  GGCAAACGAC  GCCCATGTAC  GGCCTACGTC  GCCCTTCAAT      300

GTCTCTCTTG  ACCAATAGGC  AATGCCGGCG  AGTTGACAAG  GGCCAGTGGG  GGCCGGGCGG     360

AGGGGAAGG   ACCTCCTCCG  CAGCCCTTCC  CGGGGGTGCG  GGAAATGCAT  GGGGCCACCC     420

AGCTCCGCGG  CGGCCTACAG  CCGGGGTAGC  CCAAGAGCCT  TCGGGTGAGG  GCGGGTGGCA      480

TTTTCTCTTC  CTATACCGAT  CATGGCAGTC  CTTCTGCTCT  TCTTCGTTGT  GGAGGCCGGG      540

GCCATTCTGG  CCCCGGCCAC  ACACGCTTGT  AGCGCAAAGG  GGCAATACTT  C                591
```

( 2 ) INFORMATION FOR SEQ ID NO:4:

( i ) SEQUENCE CHARACTERISTICS:
        ( A ) LENGTH: 589 base pairs
        ( B ) TYPE: nucleic acid
        ( C ) STRANDEDNESS: single -continued ( D ) TOPOLOGY: linear ( i i ) MOLECULE TYPE: DNA (genomic)

( x i ) SEQUENCE DESCRIPTION: SEQ ID NO:4:

| ACCGACGCCT | ACTGAAGTAG | ACGCAATGGC | CCCGCGCCGA | ACCGGCGACC | GGCCAAAAGG | 60 |
| TGGTGGATGG | GTGATGCCAG | GGTTGGTAGG | TCGTAAATCC | CGGTCATCTT | GGTAGCCACT | 120 |
| ATAGGTGGGT | CTTAAGGGGA | AGCAAAGGTC | CCTCTTGTGC | CTGTGGAGGG | AACGCGCACG | 180 |
| GTCCACAGGT | GTTGGTCCTA | CCGGTGTAAT | AAGGACCCGG | CGCTAGGCAC | GCCGTTAAAC | 240 |
| CGAGTCCGTT | ATCCCCTGG | GCAAACGACG | CCCATGTACG | GCCTACGTCG | CCCTTCAATG | 300 |
| TCTCTCTTGA | CCAATAGGCT | TAGCCGGCGA | GTTGGCAAGG | GCCAGTGGGG | GCCGGGCGGG | 360 |
| GGGGGAAGGA | CCCCCCTCGC | TGCCCTTCCC | GGGGGAGCGG | AAAATGCATG | GGGCCACCCA | 420 |
| GCTCCGCGGC | GGCCTACAGC | CGGGGTAGCC | CAAGAGCCTT | CGGGTGAGGG | CGGGTGGCAT | 480 |
| TTCTTTTCCT | ATACCGATCA | TGGCAGTCCT | TCTGCTCTTA | CTCGTTGTGG | AGGCCGGGGC | 540 |
| CATCTTGGCC | CCGGCCACCC | ATGCTTGTAG | CGCGAAGGGG | CAATATTTC | | 589 |

( 2 ) INFORMATION FOR SEQ ID NO:5:

( i ) SEQUENCE CHARACTERISTICS:
( A ) LENGTH: 591 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

| ACCGACGCCT | ATCTAAGTAG | ACGCAATGAC | TCGGCGCCGA | CTCGGCGACC | GGCCAAAAGG | 60 |
| TGGTGGATGG | GTGATGACAG | GGTTGGTAGG | TCGTAAATCC | CGGTCACCTT | GGTAGCCACT | 120 |
| ATAGGTGGGT | CTTAAGAGAA | GGTTAAGATT | CCTCTTGTGC | CTGCGGCGAG | ACCGCGCACG | 180 |
| GTCCACAGGT | GCTGGCCTTA | CCGGTGCAAA | TAAAGGCCCG | ACGTCAGGCT | CGTCGTTAAA | 240 |
| CCGAGCCCGT | TACCCACCTG | GGCAAACGAC | GCCACGTAC | GGTCCACGTC | GCCCTTCAAT | 300 |
| GTCTCTCTTG | ACCAATAGGC | TTAGCCGGCG | AGTTGACAAG | GACCAGTGGG | GGCCGGGGT | 360 |
| TTGGGGAAGG | ACCCCAAGCC | CTGCCCTTCC | CGGTGGGCCG | GGAAATGCAT | GGGGCCACCC | 420 |
| AGCTCCGCGG | CGGCCTGCAG | CCGGGGTAGC | GCAAGAATCC | TTCGGGTGAG | GGCGGGTGGC | 480 |
| ATTTTTCTTT | TCTATACCAT | CATGGCAGTC | CTTCTGCTCC | TTCTCGTGGT | TGAGGCCGGG | 540 |
| GCCATCCTGG | CCCCGGCCAC | CCACGCGTGT | CGAGCGAATG | GGCAATATTT | C | 591 |

( 2 ) INFORMATION FOR SEQ ID NO:6:

( i ) SEQUENCE CHARACTERISTICS:
( A ) LENGTH: 589 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

| ACCGACGCCT | ACTAAAGTAG | ACGCAATGGC | TCAGCGCCGA | ACCGGCGACC | GGCCAAAAGG | 60 |
| TGGTGGATGG | GTGATGACAG | GGTTGGTAGG | TCGTAAATCC | CGGTCATCCT | GGTAGCCATT | 120 |
| ATAGGTGGGT | CTTAAGGGGA | AGCAAAGATC | CCTCTTGCGC | TTATGGAAGG | AAAGCGCACG | 180 |
| GTCCACAGGT | GTTGGCCTAC | CGGTGTAATA | AGGCCCGGC | GATAGGCACG | CCGTTAAACC | 240 |

-continued

| | | | | | |
|---|---|---|---|---|---|
| GAGACCGTTA | TCCCTCTGGG | CAAACGACGC | TCACGTACGG | TCCACGTCGC | CCTTCAATGC | 300 |
| CTCTCTTGGC | CAATAGGTTT | ATCCGGCGAG | TTGACAAGGA | CCAGTGAGGG | CCGGGCAGGA | 360 |
| GGGGGAGGGA | CCCCCACTGC | CGCCCTTCCC | GAGGGAGCGG | GAAATGCATG | GGGCCACCCA | 420 |
| GCTCCGCGGC | GGCCTACAGC | CGGGGTAGCC | CAAGAGCCTT | CGGGTGAGGG | CGGGTGGCAT | 480 |
| TTTTCTTCCT | ATACCGATCA | TGGCAGTCCT | TCTGCTTCTA | CTCGTTGTGG | AGGCCGGGGC | 540 |
| CATTCTGGCC | CCGGCCACCC | ATGCTTGTAG | CGCGAAGGGG | CAATATTTC | | 589 |

( 2 ) INFORMATION FOR SEQ ID NO:7:

( i ) SEQUENCE CHARACTERISTICS:
    ( A ) LENGTH: 593 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

| | | | | | |
|---|---|---|---|---|---|
| ACCGACGCCT | ATCTAAGTAG | ACGCAATGAC | TCGGCGCCAA | CTCGGCGACC | GGCCAAAAGG | 60 |
| TGGTGGATGG | GTGATGACAG | GGTTGGTAGG | TCGTAAATCC | CGGTCACCTT | GGTAGCCACT | 120 |
| ATAGGTGGGT | CTTAAGAGAA | GGTTAAGATT | CCTCTTGTGC | CTGCGGCGAG | ACCGCGCACG | 180 |
| GTCCACAGGT | GTTGGCCCTA | CCGGTGTGAA | TAAGGGCCCG | ACGTCAGGCT | CGTCGTTAAA | 240 |
| CCGAGCCCGT | CACCCACCTG | GGCAAACGTC | GCCCACGTAC | GGTCCACGTC | GCCCTTCAAT | 300 |
| GTCTCTCTTG | ACCAATAGGC | TTAGCCGGCC | GAGTTGACAA | GGACCAGTGG | GGGTCGGGGG | 360 |
| CTTGGGGAGG | GACCCCAAGT | CCTGCCCTTC | CCGGTGGGCC | GGGAAATGCA | TGGGGCCACC | 420 |
| CAGCTCCGCG | GCGGCCTGCA | GCCGGGGTAG | CCCAAGAATC | CTTCGGGTGA | GGGCGGGTGG | 480 |
| CATTTTCTCT | TTTCTATACC | ATCATGGCAG | TCCTTCTGCT | CCTTCTCGTG | GTCGAGGCCG | 540 |
| GGGCCATTCT | GGCCCCGGCC | ACCCACGCTT | GTCGAGCGAA | TGGGCAATAC | TTC | 593 |

( 2 ) INFORMATION FOR SEQ ID NO:8:

( i ) SEQUENCE CHARACTERISTICS:
    ( A ) LENGTH: 590 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

| | | | | | |
|---|---|---|---|---|---|
| ACCGACGCCT | ATCTAAGTAG | ACGCGATGAC | TCGGCGCCGA | CTCGGCGACC | GGCCAAAAGG | 60 |
| TGGTGGATGG | GTGATGACAG | GGTTGGTAGG | TCGTAAATCC | CGGTCACCTT | GGTAGCCACT | 120 |
| ATAGGTGGGT | CTTAAGAGAA | GGTTAAGATT | CCTCTCGTGC | CTGCGGCGAG | ACCGCGCACG | 180 |
| GTCCGCAGGT | GTAGGCCCTA | CCGGTGTGAA | TAAGGGCCCG | ACGTCAGGCT | CGTCGTTAAA | 240 |
| CCGAGCCCGT | CACCCACCTG | GGCTAACGAC | GCCCACGTAC | GGTCCACGTC | GCCCTTCAAT | 300 |
| GTCTCTCTTG | ACCAATAGGC | TTAGCCGGCG | AGTTGACAAG | GACCAGTGGG | GGCCGGGGC | 360 |
| TTGGAGAAGG | ACTCCAAGTC | CTGCCCTTCC | CGGTGGGCCG | GGAAATGCAT | GGGGCCACCC | 420 |
| AGCTCCGCGG | CGGCCTGCAG | CCGGGGTAGC | CCAAGAACCT | TCGGGTGAGG | GCGGGTGGCA | 480 |
| TTTCTTTTTC | CTATACCATC | ATGGCAGTCC | TTCTGCTCTT | TCTCGTGGTT | GAGGCGGGG | 540 |
| CCATTTTGGC | CCCGGCCACC | CACGCTTGTC | GAGCGAATGG | GCAATATTTC | | 590 |

( 2 ) INFORMATION FOR SEQ ID NO:9:

(i) SEQUENCE CHARACTERISTICS:
    (A) LENGTH: 592 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:9:

| | | | | | | |
|---|---|---|---|---|---|---|
| ACCGACGCCT | ATCTAAGTAG | ACGCAATGAC | TCGGCGCCGA | CTCGGCGACC | GGCCAAAAGG | 60 |
| TGGTGGATGG | GTGATGACAG | GGTTGGTAGG | TCGTAAATCC | CGGTCATCCT | GGTAGCCACT | 120 |
| ATAGGTGGGT | CTTAAGAGAA | GGTCAAGATT | CCTCTTGTGC | CTGCGGCGAG | ACCGCGCACG | 180 |
| GTCCACAGGT | GTTGGCCCTA | CCGGTGTGAA | TAAGGGCCCG | ACGTCAGGCT | CGTCGTTAAA | 240 |
| CCGAGCCCGT | CACCCACCTG | GGCAAACGAC | GCCCACGTAC | GGTCCACGTC | GCCCTTCAAT | 300 |
| GTCTCTCTTG | ACCAATAGGT | TTATCCGGCG | AGTTGACAAG | GACCAGTGGG | GGCCGGGGGT | 360 |
| TACGGGGAAG | GACCCCGGAC | CCCGCCCTTC | CCGGTGGGCC | GGGAAATGCA | TGGGGCCACC | 420 |
| CAGCTCCGCG | GCGGCCTGCA | GCCGGGGTAG | CCCAAGAATC | CTTCGGATGA | GGGCGGGTGG | 480 |
| CATTTCTCTT | TTCTATACCA | TCATGGCAGT | CCTTCTGCTC | CTTCTCGTGG | TTGAGGCCGG | 540 |
| GGCCATTCTG | GCCCCGGCCA | CCCACGCTTG | TCGAGCGAAC | GGGCAATATT | TC | 592 |

(2) INFORMATION FOR SEQ ID NO:10:

(i) SEQUENCE CHARACTERISTICS:
        (A) LENGTH: 592 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

| | | | | | | |
|---|---|---|---|---|---|---|
| ACCGACGCCT | ATCTAAGTAG | ACGCAATGAC | TCGGCGCCGA | CTCGGCGACC | GGCCAAAAGG | 60 |
| TGGTGGATGG | GTGATGACAG | GGTTGGTAGG | TCGTAAATCC | CGGTCATCCT | GGTAGCCACT | 120 |
| ATAGGTGGGT | CTTAAGAGAA | GGTCAAGATT | CCTCTTGTGC | CTGCGGCGAG | ACCGCGCACG | 180 |
| GTCCACAGGT | GTTGGCCCTA | CCGGTGTGAA | TAAGGGCCCG | ACGTCAGGCT | CGTCGTTAAA | 240 |
| CCGAGCCCGT | CACCCACCTG | GGCAAACGAC | GCCCACGTAC | GGTCCACGTC | GCCCTTCAAT | 300 |
| GTCTCTCTTG | ACCAATAGGT | TTATCCGGCG | AGTTGACAAG | GACCAGTGGG | GGCCGGGGGT | 360 |
| TACGGGGAAG | GACCCCGGAC | CCCGCCCTTC | CCGGTGGGCC | GGGAAATGCA | TGGGGCCACC | 420 |
| CAGCTCCGCG | GCGGCCTGCA | GCCGGGGTAG | CCCAAGAATC | CTTCGGATGA | GGGCGGGTGG | 480 |
| CATTTCTCTT | TTCTATACCA | TCATGGCAGT | CCTTCTGCTC | CTTCTCGTGG | TTGAGGCCGG | 540 |
| GGCCATTCTG | GCCCCGGCCA | CCCACGCTTG | TCGAGCGAAC | GGGCAATATT | TC | 592 |

(2) INFORMATION FOR SEQ ID NO:11:

(i) SEQUENCE CHARACTERISTICS:
        (A) LENGTH: 592 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

| | | | | | | |
|---|---|---|---|---|---|---|
| ACCGACGCCT | ATCTAAGTAG | ACGCAATGAC | TCGGCGCCGA | CTCGGCGACC | GGCCAAAAGG | 60 |
| TGGTGGATGG | GTGATGACAG | GGTTGGTAGG | TCGTAAATCC | CGGTCACCTT | GGTAGCCACT | 120 |

| | | | | | | |
|---|---|---|---|---|---|---|
| ATAGGTGGGT | CTTAAGAGAA | GGTTAAGATT | CCTCTTGTGC | CTGCGGCGAG | ACCGCGCACG | 180 |
| GTCCACAGGT | GTTGGCCCTA | CCGGTGTGAA | TAAGGGCCCG | ACATCAGGCT | TGTCGTTAAA | 240 |
| CCGAGCCCGT | CATCCGCCTG | GGCTAACGAC | GCCCACGTAC | GGTCCACGTC | GCCCTTCAAT | 300 |
| GTCTCTCTTG | ACCAATAGGT | TCATCCGGCG | AGTTGACAAG | GACCAGTGGG | GGCCGGGGGT | 360 |
| TATGGGGAAG | GACCCCAAAC | CCTGCCCTTC | CCGGCGGACC | GGGAAATGCA | TGGGGCCACC | 420 |
| CAGCTCCGCG | GCGGCCTGCA | GCCGGGGTAG | CCCAAGAATC | CTTCGGGTGA | GGGCGGGTGG | 480 |
| CATTTTCCTT | TTCTATACCA | TCATGGCAGT | CCTTCTGCTC | CTTCTCGTGG | TTGAGGCCGG | 540 |
| GGCCATTCTG | GCCCCGGCCA | CCCACGCTTG | TCGAGCGAAT | GGGCAATATT | TC | 592 |

( 2 ) INFORMATION FOR SEQ ID NO:12:

( i ) SEQUENCE CHARACTERISTICS:
          ( A ) LENGTH: 591 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:12:

| | | | | | | |
|---|---|---|---|---|---|---|
| ACCGACGCCT | ATCTAAGTAG | ACGCAATGAC | TCGGCGCCGA | CTCGGCGACC | GGCCAAAAGG | 60 |
| TGGTGGATGG | GTGATGACAG | GGTTGGTAGG | TCGTAAATCC | CGGTCACCTT | GGTAGCCACT | 120 |
| ATAGGTGGGT | CTTAAGAGAA | GGTTAAGATT | CCTCTTGTGC | CTGCGGCGAG | ACCGCGCACG | 180 |
| GTCCACAGGT | GCTGGCCTTA | CCGGTGCAAA | TAAGGCCCG | ACGTCAGGCT | CGTCGTTAAA | 240 |
| CCGAGCCCGT | TACCCACCTG | GGCAAACGAC | GCCCACGTAC | GGTCCACGTC | GCCCTTCAAT | 300 |
| GTCTCTCTTG | ACCAATAGGC | TTAGCCGGCG | AGTTGACAAG | GACCAGTGGG | GGCCGGGGGT | 360 |
| TTGGGGAAGG | ACCCAAGCC | CTGCCCTTCC | CGGTGGGCCG | GGAAATGCAT | GGGGCCACCC | 420 |
| AGCTCCGCGG | CGGCCTGCAG | CCGGGGTAGC | GCAAGAATCC | TTCGGGTGAG | GGCGGGTGGC | 480 |
| ATTTTCTTT | TCTATACCAT | CATGGCAGTC | CTTCTGCTCC | TTCTCGTGGT | TGAGGCCGGG | 540 |
| GCCATCCTGG | CCCCGGCCAC | CCACGCGTGT | CGAGCGAATG | GGCAATATTT | C | 591 |

( 2 ) INFORMATION FOR SEQ ID NO:13:

( i ) SEQUENCE CHARACTERISTICS:
          ( A ) LENGTH: 591 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:13:

| | | | | | | |
|---|---|---|---|---|---|---|
| ACCGACGCCT | ATCTAAGTAG | ACGCAATGAC | TCGGCGCCAA | CTCGGCGACC | GGCCAAAAGG | 60 |
| TGGTGGATGG | GTGATGACAG | GGTTGGTAGG | TCGTAAATCC | CGGTCACCTT | GGTAGCCACT | 120 |
| ATAGGTGGGT | CTTAAGAGAA | GGTTAAGATT | CCTCTTGTGC | CTGCGGCGAG | ACCGCGCACG | 180 |
| GTCCACAGGT | GTTGGCCCTA | CCGGTGGGAA | TAAGGGCCCG | ACGTCAGGCT | CGTCGTTAAA | 240 |
| CCGAGCCCGT | CACCCACCTG | GGCAAACGAC | GCCCACGTAT | GGTCCACGTC | GCCCTTCAAT | 300 |
| GCCTCTCTTG | GCCAATAGGT | TTATCCGGCG | AGTTGACAAG | GACCAGTGGG | GGCCGGGGGT | 360 |
| TCGGGGAAGG | ACCTCGTACC | CTGCCCTTCC | CGGTGGAACG | GGAAATGCAT | GGGGCCACCC | 420 |
| AGCTCCGCGG | CGGCCTGCAG | CCGGGGTAGC | CCAAGAACCC | TTTGGGTGAG | GGCGGGTGGC | 480 |
| ATATCTTTTT | CCTATACCAT | CATGGCAGTC | CTTCTGCTCC | TTTTCGTGGT | TGAGGCCGGG | 540 |

| GCCATTCTGG | CCCCGGCCAC | CCACGCTTGT | CGAGCGAACG | GGCAATATTT | C | 591 |

( 2 ) INFORMATION FOR SEQ ID NO:14:

( i ) SEQUENCE CHARACTERISTICS:
        ( A ) LENGTH: 593 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

| ACCGACGCCT | ATCTAAGTAG | ACGCAATGAC | TCGGCGCCGA | CTCGGCGACC | GGCCAAAAGG | 60 |
| TGGTGGATGG | GTGATGACAG | GGTTGGTAGG | TCGTAAATCC | CGGTCACCTT | GGTAGCCACT | 120 |
| ATAGGTGGGT | CTTAAGAGAA | GGTTAAGATT | CCTCTTGTGC | CTGCGGCGAG | ACCGCGCACG | 180 |
| GTCCACAGGT | GTTGGCCCTA | CCGGTGTGAA | TAAGGGCCCG | ACGTCAGGCT | CGTCGTTAAA | 240 |
| CCGAGCCCGT | TACCCACCTG | GGCAAACGAC | GCCCACGTAC | GGTCCACGTC | GCCCTTCAAT | 300 |
| GTCTCTCTTG | ACCAATAGGA | TTCGTCCGGC | GAGTTGACAA | GGACCAGTGG | GGGCCGGGGG | 360 |
| TCATGGGGAA | GGACCCCAGA | CCCTGCCCTT | CCCGGTGGGG | CGGGAAATGC | ATGGGGCCAC | 420 |
| CCAGCTCCGC | GGCGGCCTGC | AGCCGGGGTA | GCCCAAAAAA | CCTTCGGGTG | AGGGCGGGTG | 480 |
| GCATTTCTTT | TTCCTATACC | ATCATGGCAG | TCCTTCTGCT | CTTTCTCGTG | GTGGAGGCCG | 540 |
| GGGCCATCTT | GGCCCCGGCC | ACCCATGCTT | GTCGAGCGAA | TGGGCAATAT | TTC | 593 |

( 2 ) INFORMATION FOR SEQ ID NO:15:

( i ) SEQUENCE CHARACTERISTICS:
        ( A ) LENGTH: 590 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

| ACCGACGTCT | ATCTAAGTAG | ACGCAATGAC | TCGGCGCCGA | CTCGGCGACC | GGCCAAAAGG | 60 |
| TGGTGGATGG | GTGATGCCAG | GGTTGGTAGG | TCGTAAATCC | CGGTCATCTT | GGTAGCCACT | 120 |
| ATAGGTGGGT | CTTAAGAGAA | GGTTAAGATT | CCTCTTGTGC | CTGCGGCGAG | AACACGCACG | 180 |
| GTCCACAGGT | GGTGGCCCTA | CCGGTGTGAA | TAAGGGCCCG | ACGTCAGGCT | CGTCGTTAAA | 240 |
| CTGAGCCCGC | ACCCCACCTG | GGCAAACGAC | GCCCACGTAC | GGTCCACGTC | GCCCTTCAAT | 300 |
| GTCTCCCTTG | ACCAATAGGT | TTATCCGGCG | AGTTGACAAG | GACCAGTGGG | GGCCGGGGC | 360 |
| CTGGGAAGGA | CCCCAGTCCC | TGCCCTTCCC | GGTGGGACGG | GAAATGCATG | GGCCACCCA | 420 |
| GCTCCGCGGC | GGCCTGCAGC | CGGGGTAGCC | CAAGAATCCT | TCGGGTGAGG | GCGGTGGCA | 480 |
| TTTTTCTTTT | CTATACCATC | ATGGCGGTCC | TTCTGCTCTT | TCTCGTGGTT | GAGGCCGGGG | 540 |
| CCATTCTGGC | CCCGGCCACC | CACGCTTGTC | GAGCGAATGG | GCAATATTTC | | 590 |

( 2 ) INFORMATION FOR SEQ ID NO:16:

( i ) SEQUENCE CHARACTERISTICS:
        ( A ) LENGTH: 593 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

| | | | | | |
|---|---|---|---|---|---|
| ACCGACGCCT | ATCTAAGTAG | ACGCAATGAC | TCGGCGCCGA | CCCGGCGACC | GGCCAAAAGG | 60 |
| TGGTGGATGG | GTGATGCCAG | GGTTGGTAGG | TCGTAAATCC | CGGTCATCTT | GGTAGCCACT | 120 |
| ATAGGTGGGT | CTTAAGGGAA | GGTTAAGATT | CCTCTTGTGC | CTGTGGCGAG | ACAGCGCACG | 180 |
| GTCCACAGGT | GTTGGCCCTA | CCGGTGTGAA | TAAGGGCCCG | ACGTCAGGCT | CGTCGTTAAA | 240 |
| CCGAGACCGA | CACCCACCTG | GGCAAACGAC | GCCCACGTAC | GGTCCACGTC | GCCCTTCAAT | 300 |
| GTCTCTCTTG | ACCAATAGGG | CTTTGCCCGG | CGAGTTGACA | AGGACCAGTG | GGGGCGGGG | 360 |
| GCAGGGGAA | GGACCCCCTC | GCTCCGCCCT | TCCCGGTGGG | ACGGGAAATG | CATGGGGCCA | 420 |
| CCCAGCTCCG | CGGCGGCCTG | CAGCCGGGGT | AGCCCAAGAG | CCTTCGGGTG | AGGGCGGGTG | 480 |
| GCATTCTTTT | CCTTATACCG | ATCATGGCAG | TCCTTCTGCT | TCTCTTCGTG | GTTGAGGCCG | 540 |
| GGGCCATTCT | GGCCCCGGCC | ACCCACGCTT | GTCGAGCTGA | TGGGCAATAT | TTC | 593 |

( 2 ) INFORMATION FOR SEQ ID NO:17:

( i ) SEQUENCE CHARACTERISTICS:
        ( A ) LENGTH: 593 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

| | | | | | |
|---|---|---|---|---|---|
| ACCGACGCCT | ATCTAAGTAG | ACGCAATGAC | TCGGCGCCGA | CCCGGCGACC | GGCCAAAAGG | 60 |
| TGGTGGATGG | GTGATGCCAG | GGTTGGTAGG | TCGTAAATCC | CGGTCATCTT | GGTAGCCACT | 120 |
| ATAGGTGGGT | CTTAAGGGAA | GGTTAAGATT | CCTCTTGTGC | CTGTGGCGAG | ACAGCGCACG | 180 |
| GTCCACAGGT | GTTGGCCCTA | CCGGTGTGAA | TAAGGGCCCG | ACGTCAGGCT | CGTCGTTAAA | 240 |
| CCGAGACCGA | CACCCACCTG | GGCAAACGAC | GCCCACGTAC | GGTCCACGTC | GCCCTTCAAT | 300 |
| GTCTCTCTTG | ACCAATAGGG | CTTTGCCCGG | CGAGTTGACA | AGGACCAGTG | GGGGCGGGG | 360 |
| GCAGGGGAA | GGACCCCCTC | GCTCCGCCCT | TCCCGGTGGG | ACGGGAAATG | CATGGGGCCA | 420 |
| CCCAGCTCCG | CGGCGGCCTG | CAGCCGGGGT | AGCCCAAGAG | CCTTCGGGTG | AGGGCGGGTG | 480 |
| GCATTCTTTT | CCTTATACCG | ATCATGGCAG | TCCTTCTGCT | TCTCTTCGTG | GTTGAGGCCG | 540 |
| GGGCCATTCT | GGCCCCGGCC | ACCCACGCTT | GTCGAGCTGA | TGGGCAATAT | TTC | 593 |

( 2 ) INFORMATION FOR SEQ ID NO:18:

( i ) SEQUENCE CHARACTERISTICS:
        ( A ) LENGTH: 593 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

| | | | | | |
|---|---|---|---|---|---|
| ACCGACGCCT | ATCTAAGTAG | ACGCAATGAC | TCGGCGCCGA | CCCGGCGACC | GGCCAAAAGG | 60 |
| TGGTGGATGG | GTGATGCCAG | GGTTGGTAGG | TCGTAAATCC | CGGTCATCTT | GGTAGCCACT | 120 |
| ATAGGTGGGT | CTTAAGGGAA | GGTCAAGATT | CCTCTTGTGC | CTGTGGCGAG | ACAGCGCACG | 180 |
| GTCCACAGGT | GTTGGCCCTA | CCGGTGTGAA | TAAGGGCCCG | ACGTCAGGAT | CGTCGTTAAA | 240 |
| CTGAGACCGA | CACCCACCTG | GGCAAACGAC | GCCCATGTAC | GGTCCACGTC | GCCCTTCAAT | 300 |
| GTCTCTCTTG | ACCAATAGGG | CGTTGCCCGG | CGAGTTGACA | AGGACCAGTG | GGGGCGGGG | 360 |

```
GCAGGGGGAA  GGACCCCCTC  GCTCCGCCCT  TCCCGGTGGG  ACGGGAAATG  CATGGGGCCA    420

CCCAGCTCCG  CGGCGGCCTG  CAGCCGGGGT  AGCCCAAGAA  CCTTCGGGTG  AGGGCGGGTG    480

GCATTCTTCT  TCTTATACCG  ATCATGGCAG  TCCTTCTGCT  TTTCTTCGTG  GTTGAGGCCG    540

GGGCCATTCT  GGCCCCGGCC  ACCCACGCTT  GTCGAGCTGA  TGGGCAATAT  TTC           593
```

( 2 ) INFORMATION FOR SEQ ID NO:19:

( i ) SEQUENCE CHARACTERISTICS:
    ( A ) LENGTH: 592 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:19:

```
ACCGACGCCT  ATCTAAGTAG  ACGCAATGAC  TCGGCGCCGA  CCCGGCGACC  GGCCAAAAGG     60

TGGTGGATGG  GTGATGCCAG  GGTTGGTAGG  TCGTAAATCC  CGGTCATCTT  GGTAGCCACT    120

ATAGGTGGGT  CTTAAGGGAA  GGTTAAGATT  CCTCTTGTGC  CTGTGGCGAG  ACAGCGCACG    180

GTCCACAGGT  GTTGGCCCTA  CCGGTGGGAA  TAAGGGCCCG  ACGTCAGGCT  CGTCGTTAAA    240

CCGAGACCGA  CACCCACCTG  GGCAAACGAC  GCCACGTAC   GGTCCACGTC  GCCCTTCAAT    300

GTCTCTCTTG  ACCAATAGGC  TTTGCCGGCG  AGTTGACAAG  GACCAGTGGG  GGCCGGGGT    360

GGAGGGAAGG  ACCCTCTCAC  CCTGCCCTTC  CGGTGGGAC   GGGAAATGCA  TGGGCCACC    420

CAGCTCCGCG  GCGGCCTGCA  GCCGGGGTAG  CCCAAGAGCC  TTCGGGTGAG  GCGGGTGGC    480

ATTTTTCTTT  TCTATACCGA  TCATGGCAGT  CCTTCTGCTC  TTCTTCGTGG  TTGAGGCCGG    540

GGCCATTCTG  GCCCCGGCCA  CCCACGCTTG  CCGAGCTGAT  GGACAATATT  TC            592
```

( 2 ) INFORMATION FOR SEQ ID NO:20:

( i ) SEQUENCE CHARACTERISTICS:
    ( A ) LENGTH: 591 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

```
ACCGACGCCT  ATCTAAGTAG  ACGCAATGAC  TCGGCGCCGA  CCCGGCGACC  GGCCAAAAGG     60

TGGTGGATGG  GTGATGCCAG  GGTTGGTAGG  TCGTAAATCC  CGGTCATCTT  GGTAGCCACT    120

ATAGGTGGGT  CTTAAGGGAA  GGTTAAGATT  CCTCTTGTGC  CTGTGGCGAG  ACAGCGCACG    180

GTCCACAGGT  GTTGGCCCTA  CCGGTGTGAA  TAAGGGCCCG  ACGTCAGGCT  CGTCGTTAAA    240

CTGAGACCGA  CACCCACCTG  GGCAAACGAC  GCCATGTAC   GGTCCACGTC  GCCCTTCAAT    300

GTCTCTCTTG  ACCAATAGGC  TTTGCCGGCG  AGTTGACAAG  GACCAGTGGG  GGCCGGGGT    360

GGGGGGAAGG  ACCCCCCACC  CTGCCCTTCC  GGTGGGACG   GGAAATGCAT  GGGGCCACCC   420

AGCTCCGCGG  CGGCCTGCAG  CCGGGGTAGC  CCAAGAGCCT  TCGGGTGAGG  GCGGGTGGCA   480

TTTTCCTCTT  TCATACCGAT  CATGGCAGTC  CTTCTGCTCT  TCTTCGTGGT  TGAGGCCGGG    540

GCCATTCTGG  CCCCGGCCAC  CCACGCTTGT  CGGGCTGATG  GGCAATATTT  C             591
```

( 2 ) INFORMATION FOR SEQ ID NO:21:

( i ) SEQUENCE CHARACTERISTICS:
    ( A ) LENGTH: 592 base pairs
    ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:21:

| | | | | | | |
|---|---|---|---|---|---|---|
| ACCGACGCCT | ATCTAAGTAG | ACGCAATGAC | TCTGTTCCGA | CCCGGCGACC | GGCCAAAAGG | 60 |
| TGGTGGATGG | GTGATGCCAG | GGTTGGTAGG | TCGTAAATCC | CGGTCATCTT | GGTAGCCACT | 120 |
| ATAGGTGGGT | CTTAAGGGAA | GGTTAAGATT | CCTCTTGTGC | CTGTGGCGAG | ACAGCGCACG | 180 |
| GTCCACAGGT | GTTGGCCCTA | CCGGTGTGAA | TAAGGGCCCG | ACGTCAGGCT | CGTCGTTAAA | 240 |
| CCGAGACCGA | CACCCACCTG | GGCAAACGAC | GCCCACGTAC | GGTCCACGTC | GCCCTTCAAT | 300 |
| GTCTCTCTTG | ACCAATAGGC | TTTGCCGGCG | AGTTGACAAG | GACCAGTGGG | GGCCGGGTGC | 360 |
| TGGGGGAAGG | ACCCCCTTGC | ACCGCCTTC | CCGGTGGGAC | GGGAAATGCA | TGGGGCCACC | 420 |
| CAGCTCCGCG | GCGGCCTGCA | GCCGGGGTAG | CCCAAGAGCC | TTCGGGTGAG | GGCGGGTGGC | 480 |
| ATTTCTCTTT | CCCTGACTAA | TCATGGCAGT | CCTTCTGCTC | TTCTTCGTGG | TTGAGGCCGG | 540 |
| GGCCATTCTG | GCCCCGGCCA | CCCACGCTTG | TCGGGCGAAT | GGGCAATACT | TC | 592 |

(2) INFORMATION FOR SEQ ID NO:22:

(i) SEQUENCE CHARACTERISTICS:
(A) LENGTH: 591 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:22:

| | | | | | | |
|---|---|---|---|---|---|---|
| ACCGACGCCT | ATCTAAGTAG | ACGCAATGAC | TCGGCGCCGA | CCCGGCGACC | GGCCAAAAGG | 60 |
| TGGTGGATGG | GTGATGCCAG | GGTTGGTAGG | TCGTAAATCC | CGGTCATCTT | GGTAGCCACT | 120 |
| ATAGGTGGGT | CTTAAGGGAA | GGTTAAGATT | CCTCTTGTGC | CTGTGGCGAG | ACGGCGCACG | 180 |
| GTCCACAGGT | GTTGGCCCTA | CCGGTGTGAA | TAAGGGCCCG | ACGTCAGGCT | CGTCGTTAAA | 240 |
| CCGAGACCGA | CACCCACCTG | GGCAAACGAC | GCCCACGTAC | GGTCCACGTC | GCCCTTCAAT | 300 |
| GTCTCTCTTG | ACCAATAGGC | TTTGCCGGCG | AGTTGACAAG | GACCAGTGGG | GGCCGGGTGC | 360 |
| TGGGGGAAGG | ACCCCCTTGC | ACCGCCTTC | CCGGTGGGAC | GGGAAATGCA | TGGGGCCACC | 420 |
| CAGCTCCGCG | GCGGCCTGCA | GCCGGGGTAG | CCCAAGAGCC | TTCGGGTGAG | GGCGGGTGGC | 480 |
| ATTTTCTTTT | CCTGACTAAT | CATGGCAGTC | CTTCTGCTCT | TCTTCGTGGT | TGAGGCCGGG | 540 |
| GCCATTCTGG | CCCCGGCCAC | CCACGCTTGT | CGGGCGAATG | GGCAATACTT | C | 591 |

(2) INFORMATION FOR SEQ ID NO:23:

(i) SEQUENCE CHARACTERISTICS:
(A) LENGTH: 592 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:23:

| | | | | | | |
|---|---|---|---|---|---|---|
| ACCGACGCCT | ATCTAAGTAG | ACGCAATGAC | TCGGCGCCGA | CCCGGCGACC | GGCCAAAAGG | 60 |
| TGGTGGATGG | GTGATGCCAG | GGTTGGTAGG | TCGTAAATCC | CGGTCATCTT | GGTAGCCACT | 120 |
| ATAGGTGGGT | CTTAAGGGAA | GGTTAAGATT | CCTCTTGTGC | CTGTGGCGAG | ACAGCGCACG | 180 |
| GTCCACAGGT | GTTGGCCCTA | CCGGTGTGAA | TAAGGGCCCG | ACGTCAGGCT | CGTCGTTAAA | 240 |

| | | | | | | |
|---|---|---|---|---|---|---|
| CCGAGACCGA | CACCCACCTG | GGCAAACGAT | CGCCCACGTA | CGGTCCACGT | CGCCCTTCAA | 300 |
| TGTCTCTCTT | GACCAATAGG | CTTTGCCGGC | GAGTTGACAA | GGACCAGTGG | GGGCCGGGGG | 360 |
| CTGGGAGAAG | GACTCCCACG | CCCCGCCCTT | CCCGGGGGGA | CGGGAAATGC | ATGGGGCCAC | 420 |
| CCAGCTCCGC | GGCGGCCTGC | AGCCGGGGTA | GTCCAAGAGC | CTTCGGGTGA | GGACGGGTGG | 480 |
| CATTTCTTTT | TCTACACCGA | TCATGGCAGT | CCTTCTGCTC | TTCTTCGTGG | TTGAGGCCGG | 540 |
| GGCCATTCTG | GCCCCGGCCA | CCCACGCTTG | TCGAGCTGGT | GGGCAATATT | TC | 592 |

( 2 ) INFORMATION FOR SEQ ID NO:24:

( i ) SEQUENCE CHARACTERISTICS:
            ( A ) LENGTH: 593 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:24:

| | | | | | | |
|---|---|---|---|---|---|---|
| ACCGACGCCT | ATCTAAGTAG | ACGCAATGAC | TCGGCGCCGA | CCCGGCGACC | GGCCAAAAGG | 60 |
| TGGTGGATGG | GTGATGCCAG | GGTTGGTAGG | TCGTAAATCC | CGGTCATCTT | GGTAGCCACT | 120 |
| ATAGGTGGGT | CTTAAGGGAA | GGTTAAGATT | CCTCTTGTGC | CTGTGGCGAG | ACAGCGCACG | 180 |
| GTCCACAGGT | GTTGGCCCTA | CCGGTGGGAA | TAAGGGCCCG | ACGTCAGGCT | CGTCGTTAAA | 240 |
| CCGAGACCGA | CCCCCACCTG | GGCAAACGGC | GCTCATGTAC | GGTCCACGTC | GCCCTTCAAT | 300 |
| GTCTCTCTTG | ACCAATAGGC | TTTGCCGGCG | AGTTGACAAG | GACCAGTGAG | GGCCGGGGGC | 360 |
| AGGGGGGAGG | GACCCCCCTG | TCCCGCCCTT | CCCGGTGGGA | CGGGAAATGC | ATGGGGCCAC | 420 |
| CCAGCTCCGC | GGCGGCCTGC | AGCCGGGGTA | GCCCAAGAAA | CCTTCGGGTG | AGGGCGGGTG | 480 |
| GCATTTTCTT | TTCTATACCA | ATCATGGCAG | TCCTTCTGCT | CTTCTTCGTG | GTTGAGGCCG | 540 |
| GGGCCATCTT | GGCCCCGGCC | ACCCACGCTT | GTCGGGCTGA | TGGGCAATAT | TTC | 593 |

( 2 ) INFORMATION FOR SEQ ID NO:25:

( i ) SEQUENCE CHARACTERISTICS:
            ( A ) LENGTH: 595 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:25:

| | | | | | | |
|---|---|---|---|---|---|---|
| ACCGACGCCT | ATCTAAGTAG | ACGCAATGAC | TCGGCGCCGA | CTCGGCGACC | GGCCAAAAGG | 60 |
| TGGTGGATGG | GTGATGCCAG | GGTTGGTAGG | TCGTAAATCC | CGGTCATCTT | GGTAGCCACT | 120 |
| ATAGGTGGGT | CTTAAGAGAA | GGTTAAGATT | CCTCTTGTGC | CTGCGGCGAG | ACCGCGCACG | 180 |
| GTCCACAGGT | GTTGGCCCTA | CCGGTGTAAT | AAGGGCCGA | CGTCAGGCTC | GTTGCTTAAA | 240 |
| CCGAAGCCCG | TCACCCACCT | GGCAGCGAAC | GCCACGTAC | GGTCCACGTC | GCCCTTCAAT | 300 |
| GCCTCTCTTG | GCCAATAGGA | GATTCCTCGG | CGAGTTGGCA | AGGACCAGTG | GGGGCCGGGG | 360 |
| GTCACAGGGA | AGGACCCTGG | ACCCTGCCCA | TCCCGGTGGG | CCGGGAAATC | GATGGGGCCA | 420 |
| CCCAGCTCCG | CGGCCCGGCC | TGCAGCCGGG | GTAGCCCAAG | AATCTTCGGG | TGAGGGCGGG | 480 |
| TGGCATTTCT | CTTTCCTATA | CCATCATGGC | AGTCCTTCTG | CTCCTTCTCG | TGGTTGAGGC | 540 |
| CGGGGCCATT | CTGGCCCCGG | CCACCCACGC | TTGTAGAGCG | AATGGGCAAT | ATTTC | 595 |

( 2 ) INFORMATION FOR SEQ ID NO:26:

( i ) SEQUENCE CHARACTERISTICS:
        ( A ) LENGTH: 9126 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
CCCCCCCCC  GGCACTGGGT  GCAAGCCCCA  GAAACCGACG  CCTACTGAAG  TAGACGTAAT      60
GGCCCCGCGC  CGAACCGGCG  ACCGGCCAAA  AGGTGGTGGA  TGGGTGATGA  CAGGGTTGGT     120
AGGTCGTAAA  TCCCGGTCAT  CCTGGTAGCC  ACTATAGGTG  GGTCTTAAGG  GGAGGCTACG     180
GTCCCTCTTG  CGCATATGGA  GGAAAAGCGC  ACGGTCCACA  GGTGTTGGTC  CTACCGTGT      240
AATAAGGACC  CGGCGCTAGG  CACGCCGTTA  AACCGAGCCC  GTTACTCCCC  TGGGCAAACG     300
ACGCCCACGT  ACGGTCCACG  TCGCCCTTCA  ATGTCTCTCT  TGACCAATAG  GCGTAGCGG      360
CGAGTTGACA  AGGACCAGTG  GGGGCCGGGC  GGGAGGGGGA  AGGACCCCCA  CCGCTGCCCT     420
TCCCGGGGAG  GCGGGAAATG  CATGGGGCCA  CCCAGCTCCG  CGGCGGCCTA  CAGCCGGGT      480
AGCCCAAGAA  CCTTCGGGTG  AGGGCGGGTG  GCATTTCTTT  TCCTATACCG  ATCATGGCAG     540
TCCTTCTGCT  CCTACTCGTG  GTGGAGGCCG  GGCTATTTT   AGCCCCGGCC  ACCCATGCTT     600
GTAGCGCGAA  AGGGCAATAT  TTBCTCACAA  ACTGTTGCGC  CCTGGAGGAC  ATAGGCTTCT     660
GCCTGGAGGG  CGGATGCCTG  GTGGCTCTGG  GGTGCACCAT  TTGCACCGAC  CGCTGCTGGC     720
CACTGTATCA  GGCGGGTTTG  GCCGTGCGGC  CCGGCAAGTC  CGCCGCCCAG  TTGGTGGGG      780
AACTCGGTAG  TCTCTACGGG  CCCTTGTCGG  TCTCGGCTTA  TGTGGCCGGG  ATCCTGGGC      840
TTGGGGAGGT  CTACTCGGGG  GTCCTCACCG  TCGGGGTGGC  GTTGACGCGC  AGGGTCTACC     900
CGGTCCCGAA  CCTGACGTGT  GCAGTAGAGT  GTGAGTTGAA  GTGGGAAAGT  GAGTTTTGGA     960
GATGGACTGA  ACAGCTGGCC  TCAAACTACT  GGATTCTGGA  ATACCTCTGG  AAGGTGCCTT    1020
TCGACTTTTG  GCGGGGAGTG  ATGAGCCTTT  CTCCTCTCTT  GGTGTGCGTG  GCGGCCCTCC    1080
TCCTGCTGGA  GCAGCGTATT  GTCATGGTCT  TCCTCCTGGT  CACTATGGCG  GGCATGTCAC    1140
AAGGCGCGCC  CGCCTCAGTG  TTGGGGTCAC  GGCCTTTCGA  GGCCGGGCTG  ACTTGGCAGT    1200
CTTGTTCTTG  CAGGTCGAAC  GGGTCCCGCG  CGCCGACAGG  GGAGAGGGTT  TGGGAACGTG    1260
GGAACGTCAC  ACTTTTGTGT  GACTGCCCCA  ACGGTCCTTG  GGTGTGGGTC  CCGGCCCTTT    1320
GCCAGGCAAT  CGGATGGGGC  GACCCTATCA  CTCATTGGAG  CCACGGACGA  AATCAGTGGC    1380
CCCTTTCTTG  TCCCAATTT   GTCTACGGCG  CCGTTTCAGT  GACCTGCGTG  TGGGGTTCTG    1440
TGTCTTGGTT  TGCTTCCACT  GGGGGTCGCG  ACTCCAAGGT  TGATGTGTGG  AGTTTGGTTC    1500
CAGTTGGCTC  TGCCAGCTGT  ACCATAGCCG  CACTGGGATC  TTCGGATCGC  GACACAGTGG    1560
TTGAGCTCTC  CGAATGGGGA  ATCCCCTGCG  CCACTTGTAT  CCTGGACAGG  CGGCCTGCCT    1620
CGTGTGGCAC  CTGTGTGAGG  GACTGCTGGC  CCGAGACCGG  GTCGGTACGT  TTCCCATTCC    1680
ACAGGTGTGG  CGCGGGACCG  AGGCTGACCA  GAGACCTTGA  GGCTGTGCCC  TTCGTCAATA    1740
GGACAACTCC  CTTCACCATA  AGGGGCCCC   TGGGCAACCA  GGGGCGAGGC  GACCCGGTGC    1800
GGTCGCCCTT  GGGTTTTGGG  TCCTACACCA  TGACCAAGAT  CCGAGACTCC  TTACACTTGG    1860
TGAAATGTCC  CACCCCAGCC  ATTGAGCCTC  CCACCGGAAC  GTTTGGGATC  TTCCCAGGAG    1920
TCCCCCCCCT  TAACAACTGC  ATGCTTCTCG  GCACTGAGGT  GTCAGAGGTA  TTGGGTGGGG    1980
CGGGCCTCAC  TGGGGGGTTT  TACGAACCTC  TGGTGCGGCG  GTGTTCAGAG  CTGATGGGTC    2040
```

```
GGCGGAATCC  GGTCTGCCCG  GGGTTTGCAT  GGCTCTCTTC  GGGACGGCCT  GATGGGTTCA      2100

TACATGTACA  GGGCCACTTG  CAGGAGGTGG  ATGCGGGCAA  CTTCATTCCG  CCCCCACGCT      2160

GGTTGCTCTT  GGACTTTGTA  TTTGTCCTGT  CATACCTGAT  GAAGCTGGCA  GAGGCACGGT      2220

TGGTCCCGCT  GATCCTCCTC  CTGCTATGGT  GGTGGGTGAA  CCAGTTGGCG  GTCCTTGKAC      2280

TGSCGGCTGC  KCRCGCCGCC  GTGGCTGGAG  AGGTGTTTGC  GGGCCCTGCC  TTGTCCTGGT      2340

GTCTGGGCCT  ACCCTTCGTG  AGTATGATCC  TGGGGCTAGC  AAACCTGGTG  TTGTACTTCC      2400

GCTGGATGGG  TCCTCAACGC  CTGATGTTCC  TCGTGTTGTG  GAAGCTCGCT  CGGGGGGCTT      2460

TCCCGCTGGC  ATTACTGATG  GGGATTTCCG  CCACTCGCGG  CCGCACCTCT  GTGCTTGGCG      2520

CCGAATTCTG  CTTTGATGTC  ACCTTTGAAG  TGGACACGTC  AGTCTTGGGT  TGGGTGGTTG      2580

CTAGTGTGGT  GGCTTGGGCC  ATAGCGCTCC  TGAGCTCTAT  GAGCGCGGGG  GGGTGGAAGC      2640

ACAAAGCCAT  AATCTATAGG  ACGTGGTGTA  AAGGGTACCA  GGCYCTTCGC  CAGCGCGTGG      2700

TGCGTAGCCC  CCTCGGGGAG  GGGCGGCCCA  CCAAGCCGCT  GACGATAGCC  TGGCGTCTGG      2760

CCTCTTACAT  CTGGCCGGAC  GCTGTGATGT  TGGTGGTTGT  GGCCATGGTC  CTCCTCTTCG      2820

GCCTTTTCGA  CGCGCTCGAT  TGGGCCTTGG  AGGAGCTCCT  TGTGTCGCGG  CCTTCGTTGC      2880

GTCGTTTGGC  AAGGGTGGTG  GAGTGTTGTG  TGATGGCGGG  CGAGAAGGCC  ACTACCGTCC      2940

GGCTTGTGTC  CAAGATGTGC  GCGAGAGGGG  CCTACCTGTT  TGACCACATG  GGGTCGTTCT      3000

CGCGCGCGGT  CAAGGAGCGC  TTGCTGGAGT  GGGACGCGGC  TTTGGAGMCC  CTGTCATTCA      3060

CTAGGACGGA  CTGCCGCATC  ATACGAGACG  CCGCCAGGAC  TCTGAGCTGC  GGCCAATGCG      3120

TCATGGGCTT  GCCCGTGGTG  GCTAGGCGCG  GCGATGAGGT  CCTGGTTGGG  GTCTTTCAGG      3180

ATGTGAACCA  CTTGCCTCCG  GGGTTTGYTC  CTACAGCGCC  TGTTGTCATC  CGTCGGTGCG      3240

GAAAGGGCTT  CCTCGGGGTC  ACTAAGGCTG  CCTTGACTGG  TCGGGATCCT  GACTTACACC      3300

CAGGAAACGT  CATGGTTTTG  GGGACGGCTA  CCTCGCGCAG  CATGGGAACG  TGCTTAAACG      3360

GGTTGCTGTT  CACGACATTC  CATGGGGCTT  CTTCCCGAAC  CATTGCGACA  CCTGTGGGGG      3420

CCCTTAACCC  AAGGTGGTGG  TCGGCCAGTG  ATGACGTCAC  GGTCTATCCC  CTCCCCGATG      3480

GAGCTAACTC  GTTGGTTCCC  TGCTCGTGTC  AGGCTGAGTC  CTGTTGGGTC  ATYCGATCCG      3540

ATGGGGCTCT  TTGCCATGGC  TTGAGCAAGG  GGGACAAGGT  AGAACTGGAC  GTGGCCATGG      3600

AGGTTGCTGA  CTTTCGTGGG  TCGTCTGGGT  CTCCTGTCCT  ATGCGACGAG  GGGCACGCTG      3660

TAGGAATGCT  CGTGTCCGTC  CTTCATTCGG  GGGGAGGGT   GACCGCGGCT  CGATTCACTC      3720

GGCCGTGGAC  CCAAGTCCCA  ACAGACGCCA  AGACTACCAC  TGAGCCACCC  CCGGTGCCAG      3780

CTAAAGGGGT  TTTCAAAGAG  GCTCCTCTTT  TCATGCCAAC  AGGGGCGGGG  AAAAGCACAC      3840

GCGTCCCTTT  GGAATATGGA  AACATGGGGC  ACAAGGTCCT  GCTTCTCAAC  CCGTCGGTTG      3900

CCACTGTGAG  GGCCATGGGC  CCTTACATGG  AGAAGCTGGC  GGGGAAACAT  CCTAGCATTT      3960

TCTGTGGACA  CGACACAACA  GCTTTCACAC  GGATCACGGA  CTCTCCATTG  ACGTACTCTA      4020

CCTATGGGAG  GTTTCTGGCC  AACCCGAGGC  AGATGCTGAG  GGGAGTTTCC  GTGGTCATCT      4080

GTGATGAGTG  CCACAGTCAT  GACTCAACTG  TGTTGCTGGG  TATAGGCAGG  GGCAGGGAGC      4140

TGGCGCGGGG  GTGTGGAGTG  CAATTAGTGC  TCTACGCTAC  TGCGACTCCC  CCGGGCTCGC      4200

CTATGACTCA  GCATCCATCC  ATAATTGAGA  CAAAGCTGGA  CGTCGGTGAG  ATCCCCTTTT      4260

ATGGGCATGG  TATCCCCCTC  GAGCGTATGA  GGACTGGTCG  CCACCTTGTA  TTCTGCCATT      4320

CCAAGGCGGA  GTGCGAGAGA  TTGGCCGGCC  AGTTCTCCGC  GCGGGGGTT   AATGCCATCG      4380

CCTATTATAG  GGGTAAGGAC  AGTTCCATCA  TCAAAGACGG  AGACCTGGTG  GTTTGTGCGA      4440
```

```
CAGACGCGCT  CTCTACCGGG  TACACAGGAA  ACTTCGATTC  TGTCACCGAC  TGTGGGTTAG   4500
TGGTGGAGGA  GGTCGTTGAG  GTGACCCTTG  ATCCCACCAT  TACCATTTCC  TTGCGGACTG   4560
TCCCTGCTTC  GGCTGAATTG  TCGATGCAGC  GGCGCGGACG  CACGGGAGA   GGTCGGTCGG   4620
GCCGCTACTA  CTACGCTGGG  GTCGGTAAGG  CTCCCGCGGG  GGTGGTGCGG  TCTGGTCCGG   4680
TCTGGTCGGC  AGTGGAAGCT  GGAGTGACCT  GGTATGGAAT  GGAACCTGAC  TTGACAGCAA   4740
ACCTTCTGAG  ACTTTACGAC  GACTGCCCTT  ACACCGCAGC  CGTCGCAGCT  GACATTGGTG   4800
AAGCCGCGGT  GTTCTTTGCG  GGCCTCGCGC  CCCTCAGGAT  GCATCCGAT   GTTAGCTGGG   4860
CAAAAGTTCG  CGGCGTCAAT  TGGCCCCTCC  TGGTGGGTGT  TCAGCGGACG  ATGTGTCGGG   4920
AAACACTGTC  TCCCGGCCCG  TCGGACGACC  CTCAGTGGGC  AGGTCTGAAA  GGCCCGAATC   4980
CTGCCCCACT  ACTGCTGAGG  TGGGGCAATG  ATTTGCCATC  AAAAGTGGCC  GGCCACCACA   5040
TAGTTGACGA  TCTGGTCCGT  CGGCTCGGTG  TGGCGGAGGG  ATACGTGCGC  TGTGATGCTG   5100
GRCCCATCCT  CATGGTGGGC  TTGGCCATAG  CGGGCGGCAT  GATCTACGCC  TCTTACACTG   5160
GGTCGCTAGT  GGTGGTAACA  GACTGGAATG  TGAAGGGAGG  TGGCAATCCC  CTTTATAGGA   5220
GTGGTGACCA  GGCCACCCCT  CAACCCGTGG  TGCAGGTCCC  CCCGGTAGAC  CATCGGCCGG   5280
GGGGGGAGTC  TGCGCCAGCG  GATGCCAAGA  CAGTGACAGA  TGCGGTGGCA  GCCATCCAGG   5340
TGAACTGCGA  TTGGTCTGTG  ATGACCCTGT  CGATCGGGGA  AGTCCTCACC  TTGGCTCAGG   5400
CTAAGACAGC  CGAGGCCTAC  GCAGCTACTT  CCAGGTGGCT  CGCTGGCTGC  TACACGGGGA   5460
CGCGGGCCGT  CCCCACTGTA  TCAATTGTTG  ACAAGCTCTT  CGCCGGGGGT  TGGGCCGCCG   5520
TGGTGGGTCA  CTGTCACAGC  GTCATTGCTG  CGGTGGTGGC  TGCCTATGGG  GTTTCTCGAA   5580
GTCCTCCACT  GGCCGCGGCG  GCATCCTACC  TCATGGGGTT  GGGCGTCGGA  GGCAACGCAC   5640
AGGCGCGCTT  GGCTTCAGCT  CTTCTACTGG  GGGCTGCTGG  TACGGCTCTG  GGGACCCCTG   5700
TCGTGGGACT  CACCATGGCG  GGGGCCTTCA  TGGGCGGTGC  CAGCGTGTCC  CCCTCCCTCG   5760
TCACTGTCCT  ACTTGGGGCT  GTGGGAGGTT  GGGAGGGCGT  TGTCAACGCT  GCCAGTCTCG   5820
TCTTCGACTT  CATGGCTGGG  AAACTTTCAA  CAGAAGACCT  TTGGTATGCC  ATCCCGGTAC   5880
TCACTAGTCC  TGGRGCGGGC  CTCGCGGGGA  TTGCCCTTGG  TCTGGTTTTG  TACTCAGCAA   5940
ACAACTCTGG  CACTACCACA  TGGCTGAACC  GTCTGCTGAC  GACGTTGCCA  CGGTCATCTT   6000
GCATACCCGA  CAGCTACTTC  CAACAGGCTG  ACTACTGCGA  CAAGGTCTCG  GCAATGCTGC   6060
GCCGCCTGAG  CCTTACTCGC  ACCGTGGTGG  CCCTGGTCAA  CAGGGAGCCT  AAGGTGGATG   6120
AGGTCCAGGT  GGGGTACGTC  TGGGATCTGT  GGGAGTGGGT  AATGCGCCAG  GTGCGCATGG   6180
TGATGTCTAG  ACTCCGGGCC  CTCTGCCCTG  TGGTGTCACT  CCCCTTGTGG  CACCGCGGGG   6240
AGGGGTGGTC  CGGTGAATGG  CTTCTCGATG  GGCACGTGGA  GAGTCGTTGT  CTGTGCGGGT   6300
GTGTAATCAC  CGGCGACGTC  CTCAATGGGC  AACTCAAAGA  TCCAGTTTAC  TCTACCAAGC   6360
TGTGCAGGCA  CTACTGGATG  GGAACTGTGC  CGGTCAACAT  GCTGGGCTAC  GGGGAAACCT   6420
CACCTCTTCT  CGCCTCTGAC  ACCCCGAAGG  TGGTACCCTT  CGGGACGTCG  GGGTGGGCTG   6480
AGGTGGTGGT  GACCCCTACC  CACGTGGTGA  TCAGGCGCAC  GTCCTGTTAC  AAACTGCTTC   6540
GCCAGCAAAT  TCTTTCAGCA  GCTGTAGCTG  AGCCCTACTA  CGTTGATGGC  ATTCCGGTCT   6600
CTTGGGAGGC  TGACGCGAGA  GCGCCGGCCA  TGGTCTACGG  TCCGGGCCAA  AGTGTTACCA   6660
TTGATGGGGA  GCGCTACACC  CTTCCGCACC  AGTTGCGGAT  GCGGAATGTG  GCGCCCTCTG   6720
AGGTTTCATC  CGAGGTCAGC  ATCGAGATCG  GGACGGAGAC  TGAAGACTCA  GAACTGACTG   6780
AGGCCGATTT  GCCACCAGCG  GCTGCTGCCC  TCCAAGCGAT  AGAGAATGCT  GCGAGAATTC   6840
```

-continued

| | | | | | | |
|---|---|---|---|---|---|---|
| TCGAACCGCA | CATCGATGTC | AYCATGGAGG | ATTGCAGTAC | ACCCTCTCTC | TGTGGTAGTA | 6900 |
| GCCGAGAGAT | GCCTGTGTGG | GGAGAAGACA | TACCCCGCAC | TCCATCGCCT | GCACTTATCT | 6960 |
| CGGTTACGGA | GAGCAGCTCA | GATGAGAAGA | CCCTGTCGGT | GACCTCCTCG | CAGGAGGACA | 7020 |
| CCCCGTCCTC | AGACTCATTT | GAAGTCATCC | AAGAGTCTGA | TACTGCTGAA | TCAGAGGAAA | 7080 |
| GCGTCTTCAA | CGTGGCTCTT | TCCGTACTAA | AAGCATTATT | TCCACAGAGC | GTTGCCACAC | 7140 |
| GAAAGCTAAC | GGTTAAGATG | TCTTGCTGTG | TTGAGAAGAG | CGTAACACGC | TTCTTTTCTT | 7200 |
| TAGGGTTGAC | CGTGGCTGAC | GTGGCTAGCC | TGTGTGAGAT | GGAGATCCAG | AACCATACAG | 7260 |
| CCTATTGTGA | CAAGGTGCGC | ACTCCGCTCG | AATTGCAAGT | GGGTGCTTG | GTGGGCAATG | 7320 |
| AACTTACCTT | TGAATGTGAC | AAGTGTGAGG | CACGCCAAGA | GACCCTTGCC | TCCTTCTCCT | 7380 |
| ACATATGGTC | CGGGGTCCCA | CTTACTCGGG | CCACTCCGGC | CAAACCACCA | GTGGTGAGGC | 7440 |
| CGGTGGGGTC | CTTGTTGGTG | GCAGACACCA | CCAAGGTCTA | CGTGACCAAT | CCGGACAATG | 7500 |
| TTGGGAGGAG | GGTTGACAAG | GTGACTTTCT | GGCGCGCTCC | TCGGGTACAC | GACAAGTTCC | 7560 |
| TCGTGGACTC | GATCGAGCGC | GCTCGGAGAG | CTGCTCAAGG | CTGCCTAAGC | ATGGGTTACA | 7620 |
| CTTATGAGGA | GGCAATAAGG | ACTGTTAGGC | CGCATGCTGC | CATGGGCTGG | GGATCTAAGG | 7680 |
| TGTCGGTCAG | GGACTTGGCC | ACCCCTGCGG | GGAAGATGGC | TGTTCATGAC | CGGCTTCAGG | 7740 |
| AGATACTTGA | AGGGACTCCA | GTCCCTTTTA | CCCTGACTGT | CAAAAAGGAG | GTGTTCTTCA | 7800 |
| AAGATCGTAA | GGAGGAGAAG | GCCCCCCGCC | TCATTGTGTT | CCCCCCCCTG | GACTTCCGGA | 7860 |
| TAGCTGAAAA | GCTCATTCTG | GGAGACCCGG | GGCGGGTTGC | AAAGGCGGTG | TGGGGGGGGG | 7920 |
| CTTACGCCTT | CCAGTACACC | CCCAACCAGC | GGGTTAAGGA | GATGCTAAAG | CTGTGGGAAT | 7980 |
| CAAAGAAGAC | CCCGTGCGCC | ATCTGTGTGG | ATGCCACTTG | CTTCGACAGT | AGCATTACTG | 8040 |
| ARGAGGACGT | GGCACTAGAG | ACAGAGCTTT | ACGCCCTGGC | CTCGGACCAT | CCAGAATGGG | 8100 |
| TGCGCGCCCT | GGGGAAATAC | TRTGCCTCTG | GCACAATGGT | GACCCCGGAA | GGGGTGCCAG | 8160 |
| TGGGCGAGAG | GTATTGTAGG | TCCTCGGGTG | TGTTAACCAC | AAGTGCTAGC | AACTGTTTGA | 8220 |
| CCTGCTACAT | CAAAGTGAGA | GCCGCCTGTG | AGAGGATCGG | ACTGAAAAAT | GTCTCGCTTC | 8280 |
| TCATCGCGGG | CGATGACTGC | TTAATTGTGT | GCGAGAGGCC | TGTATGCGAC | CCTTGCGAGG | 8340 |
| CCCTGGGCCG | AGCCCTGGCT | TCGTACGGGT | ACGCGTGTGA | GCCCTCGTAT | CACGCTTCAC | 8400 |
| TGGACACAGC | CCCCTTCTGC | TCCACTTGGC | TTGCTGAGTG | CAATGCGGAT | GGGRAAAGGC | 8460 |
| ATTTCTTCCT | GACCACGGAC | TTTCGGAGAC | CACTCGCTCG | CATGTCGAGC | GAGTACAGTG | 8520 |
| ACCCTATGGC | TTCGGCCATT | GGTTACATTC | TCCTCTATCC | CTGGCRTCCC | ATCACACGGT | 8580 |
| GGGTCATCAT | CCCGCATGTG | CTAACATGCG | CTTCTTTCCG | GGGTGGTGGC | ACACSGTCTG | 8640 |
| ATCCGGTTTG | GTGTCAGGTT | CATGGTAACT | ACTACAAGTT | TCCCCTGGAC | AAACTGCCTA | 8700 |
| ACATCATCGT | GGCCCTCCAC | GGACCAGCAG | CGTTGAGGGT | TACCGCAGAC | ACAACCAAAA | 8760 |
| CAAAGATGGA | GGCTGGGAAG | GTTCTGAGCG | ACCTCAAGCT | CCCTGGTCTA | GCCGTCCACC | 8820 |
| GCAAGAAGGC | CGGGGCATTG | CGAACACGCA | TGCTCCGGTC | GCGCGGTTGG | GCGGAGTTGG | 8880 |
| CTAGGGGCCT | GTTGTGGCAT | CCAGGACTCC | GGCTTCCTCC | CCCTGAGATT | GCTGGTATCC | 8940 |
| CAGGGGGTTT | CCCTCTGTCC | CCCCCCTACA | TGGGGGTGGT | TCATCAATTG | GATTTCACAG | 9000 |
| CSCAGCGGAG | TCGCTGGCGG | TGGTTGGGGT | TCTTAGCCCT | GCTCATCGTA | GCGCTCTTTG | 9060 |
| GGTGAACTAA | ATTCATCTGT | TGCGGCCGGA | GTCAGACCTG | AGCCCCGTTC | AAAAGGGGAT | 9120 |
| TGAGAC | | | | | | 9126 |

( 2 ) INFORMATION FOR SEQ ID NO:27:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:27:

AAGAGGGACC GTTGCTTCCC 20

( 2 ) INFORMATION FOR SEQ ID NO:28:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:28:

TTAAGGGGAA GCAACGGTC 19

( 2 ) INFORMATION FOR SEQ ID NO:29:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:29:

TTAAGAGAAG GTTAAGATT 19

( 2 ) INFORMATION FOR SEQ ID NO:30:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:30:

AGAGGAATCT TAACCTTCT 19

( 2 ) INFORMATION FOR SEQ ID NO:31:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:31:

TTTCCCTCCA TAAGCGCG 18

( 2 ) INFORMATION FOR SEQ ID NO:32:

( i ) SEQUENCE CHARACTERISTICS:
    ( A ) LENGTH: 18 base pairs
    ( B ) TYPE: nucleic acid
    ( C ) STRANDEDNESS: single (D) TOPOLOGY: linear (i i) MOLECULE TYPE: DNA (genomic)

(x i) SEQUENCE DESCRIPTION: SEQ ID NO:32:

CGCGCTTATG GAGAGAAA     18

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:33:

TGTGCCTGYG GCGAGACM     18

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:34:

KGTCTCGCCR CAGGCACA     18

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:35:

CCCAGAAACC GACGCCTATC     20

(2) INFORMATION FOR SEQ ID NO:36:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:36:

ATAGGCGTCG GTTTCTGGG     19

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:37:

AAGTAGACGC AATGACTCGG 20

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

CCGAGTCATT GCGTCTACTT A 21

( 2 ) INFORMATION FOR SEQ ID NO:39:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

CACTATAGGT GGGTCTTAAG 20

( 2 ) INFORMATION FOR SEQ ID NO:40:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

TTAAGACCCA CCTATAGTG 19

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

GAAGGTTAAG ATTCCTCTTG 20

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

CAAGAGGAAT CTTAACCTTC T 21

( 2 ) INFORMATION FOR SEQ ID NO:43:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:43:

CGCAATGACT CGGCGCCGA 19

( 2 ) INFORMATION FOR SEQ ID NO:44:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

GGCGCCGAGT CATTGCG 17

( 2 ) INFORMATION FOR SEQ ID NO:45:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

GGCGACCGGC CAAAAGGTG 19

( 2 ) INFORMATION FOR SEQ ID NO:46:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

CACCTTTTGG CCGGTCGCCG GG 22

( 2 ) INFORMATION FOR SEQ ID NO:47:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

CCCCGGCCAC CCATGCTTGT A 21

( 2 ) INFORMATION FOR SEQ ID NO:48:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:48:

ACAAGCATGG GTGGCCGGGG 20

(2) INFORMATION FOR SEQ ID NO:49:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:49:

CGCGAAGGGG CAATATTTC 19

(2) INFORMATION FOR SEQ ID NO:50:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:50:

GAAATATTGC CCCTTCGCGC 20

(2) INFORMATION FOR SEQ ID NO:51:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:51:

CACTGGGTGC AAGCCCCAGA A 21

(2) INFORMATION FOR SEQ ID NO:52:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:52:

CAGGGCGCAA CAGTTTGTGA G 21

(2) INFORMATION FOR SEQ ID NO:53:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:53:

AGGGTTGGTA GGTCGTAAAT CCC    23

(2) INFORMATION FOR SEQ ID NO:54:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:54:

CACTGGTCCT TGTCAACTCG C    21

(2) INFORMATION FOR SEQ ID NO:55:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:55:

CCGTACGTGG GCGTCGTTTG C    21

(2) INFORMATION FOR SEQ ID NO:56:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:56:

CGGCCAAAAG GTGGTGGATG G    21

(2) INFORMATION FOR SEQ ID NO:57:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:57:

CGGAGCTGGG TGGCCCCATG C    21

(2) INFORMATION FOR SEQ ID NO:58:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:58:

CCACAAACAC TCCAGTTTGT TAC    23

(2) INFORMATION FOR SEQ ID NO:59:

(i) SEQUENCE CHARACTERISTICS:
  (A) LENGTH: 28 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:59:

| | | | |
|---|---|---|---|
| GCTCTAGACA | TGTGCTACGG | TCTACGAG | 28 |

(2) INFORMATION FOR SEQ ID NO:60:

(i) SEQUENCE CHARACTERISTICS:
    (A) LENGTH: 633 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:60:

| | | | | | |
|---|---|---|---|---|---|
| CACTGGGTGC | AAGCCCAGA | AACCGACGCC | TATCTAAGTA | GACGCAATGA | CTCGGCGCCG | 60 |
| ACTCGGCGAC | CGGCCAAAAG | GTGGTGGATG | GGTGATGACA | GGGTTGGTAG | GTCGTAAATC | 120 |
| CCGGTCACCT | TGGTAGCCAC | TATAGGTGGG | TCTTAAGAGA | AGGTTAAGAT | TCCTCTTGTG | 180 |
| CCTGCGGCGA | GACCGCGCAC | GGTCCACAGG | TGCTGGCCTT | ACCGGTGCAA | ATAAAGGCCC | 240 |
| GACGTCAGGC | TCGTCGTTAA | ACCGAGCCCG | TTACCCACCT | GGGCAAACGA | CGCCCACGTA | 300 |
| CGGTCCACGT | CGCCCTTCAA | TGTCTCTCTT | GACCAATAGG | CTTAGCCGGC | GAGTTGACAA | 360 |
| GGACCAGTGG | GCGCCGGGGG | TTTGGGGAAG | GACCCCAAGC | CCTGCCCTTC | CCGGTGGGCC | 420 |
| GGGAAATGCA | TGGGCCACC | CAGCTCCGCG | GCGGCCTGCA | GCCGGGTAG | CCCAAGAATC | 480 |
| CTTCGGGTGA | GGGCGGGTGG | CATTTTTCTT | TCCTATACCA | TCATGGCAGT | CCTTCTGCTC | 540 |
| CTTCTCGTGG | TTGAGGCCGG | GGCCATCCTG | GCCCCGGCCA | CCCACGCGTG | TCGAGCGAAT | 600 |
| GGGCAATATT | TCCTCACAAA | CTGTTGCGCC | CTG | | | 633 |

(2) INFORMATION FOR SEQ ID NO:61:

(i) SEQUENCE CHARACTERISTICS:
    (A) LENGTH: 366 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:61:

| | | | | | |
|---|---|---|---|---|---|
| AGGGTTGGTA | GGTCGTAAAT | CCCGGTCACC | TTGGTAGCCA | CTATAGGTGG | GTCTTAAGGG | 60 |
| GAGGTTAAGA | TTCCTCTTGT | GCCTGCGGCG | AGACCGCGCA | CGGTCCACAG | GTGTTGGCCC | 120 |
| TACCGGTGTG | AATAAGGGCC | CGACGTCAGG | CTCGTCGTTA | AACCGAGCCC | GTTCCCCGCC | 180 |
| TGGGCAAACG | ACGCCCACGT | ACGGTCCACG | TCGCCCTTCA | ATGTCTCTCT | TGACCAATAG | 240 |
| GTTCATCCGG | CGAGTTGACA | AGGACCAGTG | GGGGCCGGGG | GTCATGGGA | AGGACCCCAG | 300 |
| ACCCTGCCCT | TCCCGGCGGG | YCGGGAAATG | CATGGGGCCA | CCCAGCTCCG | GCATGGGGCC | 360 |
| ACCCAG | | | | | | 366 |

(2) INFORMATION FOR SEQ ID NO:62:

(i) SEQUENCE CHARACTERISTICS:
    (A) LENGTH: 349 base pairs (B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:62:

| | | | | | |
|---|---|---|---|---|---|
| AGGGTTGGTA | GGTCGTAAAT | CCCGGTCACC | TTGGTAGCCA | CTATAGGTGG | GTCTTAAGAG | 60
| AAGGTTAAGA | TTCCTCTTGT | GCCTGCGGCG | AGACCGCGCA | CGGTCCACAG | GTGTTGGCCC | 120
| TACCGGTGTT | AATAAGGGCC | CGACGTCAGG | CTCGTCGTTA | AACCGAGCCC | GTCACCCACC | 180
| TGGGCAAACG | ACGCCCACGT | ACGGTCCACG | TCGCCCTTCA | ATGTCTCTCT | TGACCAATAG | 240
| GCTTAGCCGG | CGAGTTGACA | AGGACCAGTG | GGGGCCGGGG | GCCTGGAGAG | GGACTCCAGG | 300
| TCCTGCCCTT | CCCGGTGGGC | CGGGAAATGC | ATGGGCCAC | CCAGCTCCG | | 349

(2) INFORMATION FOR SEQ ID NO:63:

(i) SEQUENCE CHARACTERISTICS:
(A) LENGTH: 632 base pairs
(B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:63:

| | | | | | |
|---|---|---|---|---|---|
| CACTGGGTGC | AAGCCCCAGA | AACCGACGCC | TATTTAAACA | GACGTTATGA | ACCGGCGCCG | 60
| ACCCGGCGAC | CGGCCAAAAG | GTGGTGGATG | GGTGATGCCA | GGGTTGGTAG | GTCGTAAATC | 120
| CCGGTCATCT | TGGTAGCCAC | TATAGGTGGG | TCTTAAGGGT | TGGTCAAGGT | CCCTCTGGCG | 180
| CTTGTGGCGA | GAAAGCGCAC | GGTCCACAGG | TGTTGGCCCT | ACCGGTGTGA | ATAAGGGCCC | 240
| GACGTCAGGC | TCGTCGTTAA | ACCGAGCCCA | TTACCCACCT | GGGCAAACGA | CGCCCACGTA | 300
| CGGTCCACGT | CGCCCTACAA | TGTCTCTCTT | GACCAATAGG | CTTTGCCGGC | GAGTTGACAA | 360
| GGACCAGTGG | GGGCCGGGCG | GCAGGGGAAG | GACCTCTGTC | GCTGCCCTTC | CCGGTGGGGT | 420
| GGGAAATGCA | TGGGGCCACC | CAGCTCCGCG | GCGGCCTGCA | GCCGGGGTAG | CCCAAGAGCC | 480
| TTCGGGTGAG | GGCGGGTGGC | ATTCTTCTTC | TTTAACCGAT | CATGGCAGTC | CTTCTGCTTC | 540
| TCCTCGTTGT | GGAGGCCGGG | GCCATTCTGG | CCCCGGCCAC | ACACGCTTGT | GGAGCGAATG | 600
| GGCAATATTT | CCTCACAAAC | TGTTGCGCCC | TG | | | 632

(2) INFORMATION FOR SEQ ID NO:64:

(i) SEQUENCE CHARACTERISTICS:
(A) LENGTH: 633 base pairs
(B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:64:

| | | | | | |
|---|---|---|---|---|---|
| CACTGGGTGC | AAGCCCCAGA | AACCGACGCC | TACTAAAGTA | GACGCAATGG | TCCAGCGCCG | 60
| AACCGGCGAC | CGGCCAAAAG | GTGGTGGATG | GGTGATGACA | GGGTTGGTAG | GTCGTAAATC | 120
| CCGGTCATCC | TGGTAGCCAC | TATAGGTGGG | TCTTAAGGGG | AAGCAAAGGT | CCCTCTTGCG | 180
| CCCATGGAGG | GAAAGCGCAC | GGTCCACAGG | TGTTGATCCT | ACCGGTGTAA | TAAGGATCCG | 240
| GCGATAGGCA | CGCCGTTAAA | CTGAGACCGT | TACCCCTCTG | GGTAAACGAC | GCCCACGTAC | 300
| GGTCCACGTC | GCCCTTCAAT | GTCTCTCTTG | ACCAATAGGC | TTAGCCGGCG | AGTTGACAAG | 360

-continued

| | | | | | |
|---|---|---|---|---|---|
| GACCAGTGGG | GGCCGGGCGG | GAGGGGGATG | GACCCCACC | GCTGCCCATT | CCGAGGGGGC | 420
| GGGAAATGCA | TGGGGCCACC | CAGCTCCGCG | GCGGCCTACA | GCCGGGGTAG | CCCAAGAGCC | 480
| TTCGGGTGAG | GGCGGGTGGC | ATTTTCTTT | CCTATACCGA | TCATGGCAGT | CCTTCTGCTC | 540
| TTACTCGTGG | CGGAGGCCGG | GGCCATCTTG | GCCCCGGCCA | CCCATGCTTG | TAGTGCGCAG | 600
| GGACAATATT | TCCTCACAAA | CTGTTGCGCC | CTG | | | 633

(2) INFORMATION FOR SEQ ID NO:65:

(i) SEQUENCE CHARACTERISTICS:
        (A) LENGTH: 632 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:65:

| | | | | | |
|---|---|---|---|---|---|
| CACTGGGTGC | AAGCCCAGA | AACCGACGCC | TACTAAAGTA | GACGCAATGG | CCCCGCGCCG | 60
| AACCGGCGAC | CGGCCAAAAG | GTGGTGGATG | GGTGATGACA | GGGTTGGTAG | GTCGTAAATC | 120
| CCGGTCATCC | TGGTAGCCAC | TATAGGTGGG | TCTTAAGGGG | AAGCAAAGGT | CCCTCTTGTG | 180
| CCTGTGGAGG | GAAAGCGCAC | GGTCCACAGG | TGTTGGTCCT | ACCGGTGTAA | TAAGGACCCG | 240
| GCGCTAGGCA | CGCCGTTAAA | CCGAGCCCGT | TATCCCCTG | GGCAAACGAC | GCCCACGTAC | 300
| GGCCTACGTC | GCCCTTCAAT | GTCTCTCTTG | ACCAATAGGC | GTAGCCGGCG | AGTTGACAAG | 360
| GGCCAGTGGG | GGCCGGGCAA | TGAGGGGAAG | GACCCCTCTT | GCTGCCCGAT | CCGGGGGAGC | 420
| GGGAAATGCA | TGGGGCCACC | CAGCTCCGCG | GCGGCCTACA | GCCGGGGTAG | CCCAAGAGCC | 480
| TTCGGGTGAG | GGCGGGTGGC | ATTTTCTTC | CTATACCGAT | CATGGCAGTC | CTTCTGCTTC | 540
| TACTCGTGGT | GGAGGCCGGG | GCCATTCTGG | CCCCGGCCAC | ACATGCTTGT | AGTGCTAAGG | 600
| GGCAATATTT | CCTCACAAAC | TGTTGCGCCC | TG | | | 632

(2) INFORMATION FOR SEQ ID NO:66:

(i) SEQUENCE CHARACTERISTICS:
        (A) LENGTH: 632 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:66:

| | | | | | |
|---|---|---|---|---|---|
| CACTGGGTGC | AAGCCCAGA | AACCGACGCC | TACTAAAGTA | GAYGCAATGG | CCCCGCGCCG | 60
| AACCGGCGAC | CGGCCAAAAG | GTGGTGGATG | GGTGATGACA | GGGTTGGTAG | GTCGTAAATC | 120
| CCGGTCATCC | TGGTAGCCAC | TATAGGTGGG | TCTTAAGGGG | AAGCAAAGGT | CCCTCTTGTG | 180
| CCTGTGGAGG | GAAAGCGCAC | GGTCCACAGG | TGTTGGTCCT | ACCGGTGTAA | TAAGGACCCG | 240
| GCGCTAGGCA | CGCCGTTAAA | CCGAGTCCGT | GAACCCCTG | GGCAAACGAC | GCCCATGTAC | 300
| GGTCTACGTC | GCCCTTCAAT | GTCTCTCTTG | ACCAATAGGC | GTAGCCGGCG | AGTTGGCAAA | 360
| GACCAGTGGG | GGCCGGGCGA | GAGGGGAAG | GACCCCCTC | GCTGCCCGTT | CCGGGGTGC | 420
| GGAAAATGCA | TGGGGCCACC | CAGCTCCGCG | GCGGCCTACA | GCCGGGGTAG | CCCAAGAGCC | 480
| TTCGGGTGAG | GGCGGGTGGC | ATTACTCTTC | CTATACCAAT | CATGGCAGTT | CTTCTGCTTC | 540
| TACTCGTTGT | GGAGGCCGGG | GCCATTTTGG | CCCCGGCCAC | CCATGCTTGT | AGTGCTGGGG | 600
| GGCAATATTT | CCTCACAAAC | TGTTGCGCCC | TG | | | 632

( 2 ) INFORMATION FOR SEQ ID NO:67:

( i ) SEQUENCE CHARACTERISTICS:
    ( A ) LENGTH: 633 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:67:

```
CACTGGGTGC  AAGCCCAGA   AACCGACGCC  TACTGAAGTA  GACGCAATGG  CCCAGCGCCG   60
AACCGGCGAC  CGGCCAAAAG  GTGGTGGATG  GGTGATGACA  GGGTTGGTAG  GTCGTAAATC  120
CCGGTCATCC  TGGTAGCCAC  TATAGGTGGG  TCTTAAGGGG  AGGCTAAGGT  CCCTCTTGTG  180
CTTATGGAAG  GAAAGCGCAC  GGTCCACAGG  TGTTGATCCT  ACCGGTGTAA  TAAGGATCCG  240
GCGATAGGCA  CGCCGTTAAA  CCGAGACCGT  TGCCCCTCTG  GGCAAACGAC  GCCCACGTAC  300
GGTCCACGTC  GCCCTTCAAT  GTCTCTCTTG  ACCAATAGGC  TTTGCCGGCG  AGTTGACAAG  360
GACCAGTGGG  GGCCGGGCGG  GAGGGGGAAG  GACCCCACC   GCTGCCCTTC  CGAGGGGGC   420
GGGAAATGCA  TGGGGCCACC  CAGCTCCGCG  GCGGCCTACA  GCCGGGGTAG  CCCAAGAGCC  480
TTCGGGTGAG  GGCGGGTGGC  ATTTTCTTTT  CCTATACCGA  TCATGGCAGT  CCTTCTGCTC  540
TCACTCGTGG  TGGAGGCCGG  GGCCATTCTG  GCCCCGGCCA  CCCATGCTTG  TAGTGCGAAG  600
GGGCAATATT  TCCTCACAAA  CTGTTGCGCC  CTG                                 633
```

( 2 ) INFORMATION FOR SEQ ID NO:68:

( i ) SEQUENCE CHARACTERISTICS:
    ( A ) LENGTH: 632 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:68:

```
CACTGGGTGC  AAGCCCAGA   AACCGACGCC  TACTAAAGTA  GACGCAATGG  CCCAGCGCCG   60
AACCGGCGAC  CGGCCAAAAG  GTGGTGGATA  GGTGATGACA  GGGTTGGTAG  GTCGTAAATC  120
CCGGTCATCC  TGGTAGCCAC  TATAGGTGGG  TCTTAAGGGG  AGGCTAAGGT  CCCTCTTGTG  180
CTTATGGAAG  GAAAGCGCAC  GGTCCACAGG  TGTTGATCCT  ACCGGTGTAA  TAAGGATCCG  240
GCGATAGGCA  CGCCGTTAAA  CCGAGACCGT  TGCCCCTCTG  GGCAAACGAC  GCCCACGTAC  300
GGTCCACGTC  GCCCTTCAAT  GTCTCTCTTG  ACCAATAGGC  TTTGCCGGCG  AGTTGACAAG  360
GACCAGTGGG  GGCCGGGCGG  GAGGGGGAAG  GACCCCACC   GCTGCCCTTC  CGAGGGGGC   420
GGGAAATGCA  TGGGGCCACC  CAGCTCCGCG  GCGGCCTACA  GCCGGGGTAG  CCCAAGAGCC  480
TTCGGGTGAG  GGCGGGTGGC  ATTTCTCTTC  CTATACCGAT  CATGGCAGTC  CTTCTGCTCT  540
TACTCGTGGT  GGAGGCCGGG  GCCATTCTGG  CCCCGGCCAC  CCATGCTTGT  AGTGCGAAGG  600
GGCAATATTT  CCTCACAAAC  TGTTGCGCCC  TG                                  632
```

( 2 ) INFORMATION FOR SEQ ID NO:69:

( i ) SEQUENCE CHARACTERISTICS:
    ( A ) LENGTH: 632 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:69:

```
CACTGGGTGC AAGCCCCAGA AACCGACGCC TACTAAAGTA GACGCAATGG TCCAGCGCCG      60
AACCGGCGAC CGGCCAAAAG GTGGTGGATG GGTGATGACA GGGTTGGTAG GTCGTAAATC     120
CCGGTCATCC TGGTAGCCAC TATAGGTGGG TCTTAAGGGG AAGCAAGGC  CCCTCTTGTG     180
CCTATGGAGG GAAAGCGCAC GGTCCACAGG TGTTGATCCT ACCGGTGTAA TAAGGATCCG     240
GCGATAGGCA CGCCGTTAAA CCGAGACCGT TACCCCTCTG GGTAAACGAC GCCCACGTAC     300
GGTCCACGTC GCCCTACAAT GTCTCTCTTG ACCAATAGGC TTAGCCGGCG AGTTGACAAG     360
GACCAGTGGG GGCCGGGCGG GAGGGGGATG GACCCCCACC GCTGCCCATT CCGAGGGGGC     420
GGGAAATGCA TGGGCCACC  CAGCTCCGCG GCGGCCTACA GCCGGGGTAG CCCAAGAGCC     480
TTCGGGTGAG GGCGGGTGGC ATTTTCTTTC CTATACCGAT CATGGCAGTC CTTCTGCTCT     540
TACTCGTTGT GGAGGCCGGG GCCATTCTGG CCCCGGCCAC CCATGCTTGT GGTGCGCAGG     600
GACAATATTT CCTCACAAAC TGTTGCGCCC TG                                   632
```

( 2 ) INFORMATION FOR SEQ ID NO:70:

( i ) SEQUENCE CHARACTERISTICS:
        ( A ) LENGTH: 633 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:70:

```
CACTGGGTGC AAGCCCCAGA AACCGACGCC TACTAAAGTA GACGCAATGG TCCAGCGCCG      60
AACCGGCGAC CGGCCAAAAG GTGGTGGATG GGTGATGACA GGGTTGGTAG GTCGTAAATC     120
CCGGTCATCC TGGTAGCCAC TATAGGTGGG TCTTAAGGGG AAGCAAAGGC CCCTCTTGTG     180
CCTATGGAGG GAAAGCGCAC GGTCCACAGG TGTTGATCCT ACCGGTGTAA TAAGGATCCG     240
GCGATAGGCA CGCCGTTAAA CCGAGACCGT TACCCCTCTG GGTAAACGAC GCCCACGTAC     300
GGTCCACGTC GCCCTACAAT GTCTCTCTTG ACCAATAGGC TTAGCCGGCG AGTTGACAAG     360
GACCAGTGGG GGCCGGGCGG GAGGGGGATG GACCCCCACC GCTGCCCATT CCGAGGGGGC     420
GGGAAATGCA TGGGCCACC  CAGCTCCGCG GCGGCCTACA GCCGGGGTAG CCCAAGAGCC     480
CTCGGGTGAG GGCGGGTGGC ATTTTCTTT  CCTATACCGA TCATGGCAGT CCTTCTGCTC     540
TTACTCGTTG TGGAGGCCGG GGCCATTCTG GCCCCGGCCA CCCATGCTTG TGGTGCGCAG     600
GGACAATATT TCCTCACAAA CTGTTGCGCC CTG                                  633
```

( 2 ) INFORMATION FOR SEQ ID NO:71:

( i ) SEQUENCE CHARACTERISTICS:
        ( A ) LENGTH: 632 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:71:

```
CACTGGGTGC AAGCCCCAGA AACCGACGCC TACTAAAGTA GACGCAATGG TCCAGCGCCG      60
AACCGGCGAC CGGCCAAAAG GTGGTGGATG GGTGATGACA GGGTTGGTAG GTCGTAAATC     120
CCGGTCATCC TGGTAGCCAC TATAGGTGGG TCTTAAGGGG AAGCAAAGGC CCCTCTTGTG     180
CCTATGGAGG GAAAGCGCAC GGTCCACAGG TGTTGATCCT ACCGGTGTAA TAAGGATCCG     240
```

| | | | | | | |
|---|---|---|---|---|---|---|
| GCGATAGGCA | CGCCGTTAAA | CCGAGACCGT | TACCCCTCTG | GGTAAACGAC | GCCCACGTAC | 300 |
| GGTCCACGTC | GCCCTACAAT | GTCTCTCTTG | ACCAATAGGC | TTAGCCGGCG | AGTTGACAAG | 360 |
| GACCAGTGGG | GGCCGGGCGG | GAGGGGGATG | GACCCCCACC | GCTGCTCATT | CCGAGGGGGC | 420 |
| GGGAAATGCA | TGGGGCCACC | CAGCTCCGCG | GCGGCCTACA | GCCGGGGTAG | CCCAAGAGCC | 480 |
| TTCGGGTGAG | GGCGGGTGGC | ATTTTCTTTC | CTATACCGAT | CATGGCAGTC | CTTCTGCTCT | 540 |
| TACTCGTTGT | GGAGGCCGGG | GCCATCCTGG | CCCCGGCCAC | CCATGCTTGT | GGTGCGCAGG | 600 |
| GACAATATTT | CCTCACAAAC | TGTTGCGCCC | TG | | | 632 |

( 2 ) INFORMATION FOR SEQ ID NO:72:

( i ) SEQUENCE CHARACTERISTICS:
        ( A ) LENGTH: 633 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:72:

| | | | | | | |
|---|---|---|---|---|---|---|
| CACTGGGTGC | AAGCCCCAGA | AACCGACGCC | TACTAAAGTA | GACGCAATGG | TCCAGCGCCG | 60 |
| AACCGGCGAC | CGGCCAAAAG | GTGGTGGATG | GGTGATGACA | GGGTTGGTAG | GTCGTAAATC | 120 |
| CCGGTCATCC | TGGTAGCCAC | TATAGGTGGG | TCTTAAGGGG | AAGCAAGGC | CCCTCTTGTG | 180 |
| CCTATGGAGG | GAAAGCGCAC | GGTCCACAGG | TGTTGATCCT | ACCGGTGTAA | TAAGGATCTG | 240 |
| GCGATAGGCA | CGCCGTTAAA | CCGAGACCGT | TACCCCTCTG | GGTAAACGAC | GCCCACGTAC | 300 |
| GGTCCACGTC | GCCCTACAAT | GTCTCTCTTG | ACCAATAGGC | TTAGCCGGCG | AGTTGACAAG | 360 |
| GACCAGTGGG | GGCCGGGCGG | GAGGGGGATG | GACCCCCACC | GCTGCCCATT | CCGAGGGGGC | 420 |
| GGGAAATGCA | TGGGGCCACC | CAGCTCCGCG | GCGGCCTACA | GCCGGGGTAG | CCCAAGAGCC | 480 |
| TTCGGGTGAG | GGCGGGTGGC | ACTTTTCTTT | CCTATACCGA | TCATGGCAGT | CCTTCTGCTC | 540 |
| TTACTCGTTG | TGGAGGCCGG | GGCCATTCTG | GCCCCGGCCA | CCCATACTTG | TGGTGCGCAG | 600 |
| GGACAATATT | CCTCACAAA | CTGTTGCGCC | CTG | | | 633 |

( 2 ) INFORMATION FOR SEQ ID NO:73:

( i ) SEQUENCE CHARACTERISTICS:
        ( A ) LENGTH: 630 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:73:

| | | | | | | |
|---|---|---|---|---|---|---|
| CACTGGGTGC | AAGCCCCAGA | AACCGACGCC | TATCAAAATA | GACGTGATGG | CCCTGCGCCG | 60 |
| AACCGGCGAC | CGGCCAAAAG | GTGGTGGATG | GGTGATGCCA | GGGTTGGTAG | GTCGTAAATC | 120 |
| CCGGTCATCT | TGGTAGCCAC | TATAGGTGGG | TCTTAAGGGG | AGGCAACGGT | CCCTCTCGCG | 180 |
| CTTACGGAGA | GAAGGCGCAC | GGTCCACAGG | TGTTGGTCCT | ACCGGTGTGA | ATAAGGACTC | 240 |
| GGCGTTAGGC | TCGCCGTTAA | ACCGAGCCCG | TTAACCCCCT | GGGCAAACGA | CGCCCACGTA | 300 |
| CGGTCTACGT | CGCCCTTCAA | TGTCTCTCTT | GACCAATAGG | CAATGCCGGC | GAGTTGACAA | 360 |
| GGACCAGTGG | GGGCCGGGTG | GGGGAAGGA | CCCCCCTCAC | TGCCCTTCCC | GGGGGTGCGG | 420 |
| GAAATGCATG | GGGCCACCCA | GCTCCGCGGC | GGCCTACAGC | CGGGGTAGCC | CAAGAACCTT | 480 |
| CGGGTGAGGG | CGGGTGGCAT | TTTTCTTCCT | ATACCGATCA | TGGCAGTCCT | CCTGCTCTTC | 540 |

```
TTCGTGGTGG AGGCCGGGGC CATTTTGGCC CCGGCCACCC ATGCTTGCAG TGCAAAGGG      600

CAATACTTCC TCACAAACTG TTGCGCCCTG                                      630
```

( 2 ) INFORMATION FOR SEQ ID NO:74:

( i ) SEQUENCE CHARACTERISTICS:
        ( A ) LENGTH: 633 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:74:

```
CACTGGGTGS AAGCCCCAGA AACCGACGCC TACTAAAGTA GACGCAATGG CCCCGCGCCG      60

AACCGGCGAC CGGCCAAAAG GTGGTGGATG GGTGATGACA GGGTTGGTAG GTCGTAAATC     120

CCGGTCATCC TGGTAGCCAC TATAGGTGGG TCTTAAGGGG AAGCAAAGGT CCCTCTTGTG     180

CCTGTGGAGG GAAAGCGCAC GGTCCACAGG TGTTGGTCCT ACCGGTGTAA TAAGGACCCG     240

GCGTTAGGCA CGCCGTTAAA CCGAGCCCGT TATCTCCCTG GGCAAACGAC GCCCACGTAC     300

GGCCAACGTC GCCCTTCAAT GTCTCTCTTG ACCAATAGGC TTAGCCGGCG AGTTGACAAT     360

GGCCAGTGGG GGCCGGGCGA GAGGGGGAAG GACCCCCCTC GCTGCCATT  CCGGGGGAGC     420

GGGAAATGCA TGGGCCACC  CAGCTCCGCG GCGGCCTACA GCCGGGGTAG CCCAAGAACC     480

TTCGGGTGAG GGCGGGTGGC ATTTTCTTT  CCTATACCGA TCATGGCAGT CCTTCTGCTC     540

TTACTCGTTG TGGAGGCCGG GGCCATTTTG GCCCCGGCCA CCCATGCTTG TAGTGCTAAA     600

GGGCAATATT TCCTCACAAA CTGTTGCGCC CTG                                  633
```

( 2 ) INFORMATION FOR SEQ ID NO:75:

( i ) SEQUENCE CHARACTERISTICS:
        ( A ) LENGTH: 589 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:75:

```
ACCGACGCCT ATCAAAGTAG ACGTGATAGC CCCGCGCCAA ACTGGCGACA GGCCAAAAGG      60

TGGTGGATGG GTGATGACAG GGTTGGTAGG TCGTAAATCC CGGTCATCCT GGTAGCCACT     120

ATAGGTGGGT CTTAAGGGC  GGCTACGGTC CCTCTCGCGC TTATGGAGAG AAAGCGCACG     180

GTCCACAGGT GTTGGcCCTA CCGGTGTAAT AAGGGCCCGG CGCTAGGCAC GCCGTTAAAC     240

CGAGACCGTT ACCCCCTGG  GCAAACGACG CCCACGTACG GCCCACGTCG CCCTTCAATG     300

TCTCTCTTGA CCAATAGGCT ATGCCGGCGA GTTGACAAGG GCCAGTGGGG GCCGGGCGGC     360

AGGGGAAGGA CCCCTGTCGC TGCCCTTCCC GGGGGGCGG  GAAATGCATG GGCCACCCA     420

GCTCCGCGGC GCCCTACAGC CGGGGTAGTC CAAGAACCTT CGGGTGAGGA CGGGTGGCAT     480

TTCTTTTCCT ATACCGATCA TGGCAGTCTT TCTGCTCTTA CTCGTGGTGG AGGCCGGGGC     540

CATTCTGGCC CCGGCCACAC ACGCTTGTAG TGCTAAAGGG CAATACTTC                 589
```

( 2 ) INFORMATION FOR SEQ ID NO:76:

( i ) SEQUENCE CHARACTERISTICS:
        ( A ) LENGTH: 632 base pairs
        ( B ) TYPE: nucleic acid
        ( C ) STRANDEDNESS: double -continued (D) TOPOLOGY: linear (ii) MOLECULE TYPE: DNA (genomic)

(xi) SEQUENCE DESCRIPTION: SEQ ID NO:76:

| CACTGGGTGC | AAGCCCCAGA | AACCGACGCC | TATCAAAGTA | GACGTGATGG | CCCCGCGCCA | 60 |
| AACTGGCGAC | CGGCCAAAAG | GTGGTGGATG | GGTGATGACA | GGGTTGGTAG | GTCGTAAATC | 120 |
| CCGGTCATCC | TGGTAGCCAC | TATAGGTGGG | TCTTAAAGGG | CGGCTACGGT | CCCTCTCGCG | 180 |
| CTTATGGAGA | GAAAGCGCAC | GGTCCACAGG | TGTTGGCCCT | ACCGGTGTAA | TAAGGGCCCG | 240 |
| GCGCTAGGCA | CGCCGTTAAA | CCGAGACCGT | TACCCCCTG | GGCAAACGAC | GCCCACGTAC | 300 |
| GGCCCACGTC | GCCCTTCAAT | GTCTCTCTTG | ACCAATAGGC | TATGCCGGCG | AGTTGACAAG | 360 |
| GGCCAGTGGG | GGCCGGGCGG | CAGGGGAAGG | ACCCTGTCG | CTGCCCTTCC | CGGGGGGCG | 420 |
| GGAAATGCAT | GGGGCCACCC | AGCTCCGCGG | CGCCCTACAG | CCGGGGTAGT | CCAAGAACCT | 480 |
| TCGGGTGAGG | ACGGGTGGCA | TTTTCTTTTC | CTATACCGAT | CATGGCCGTC | CTTCTGCTCT | 540 |
| TACTCGTGGT | GGAGGCCGGG | GCCATTCTGG | CCCCGGCCAC | ACACGCTTGT | GGTGCTAAAG | 600 |
| GGCAATACTT | CCTCACAAAC | TGTTGCGCCC | TG | | | 632 |

(2) INFORMATION FOR SEQ ID NO:77:

(i) SEQUENCE CHARACTERISTICS:
(A) LENGTH: 632 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:77:

| CACTGGGTGC | AAGCCCCAGA | AACCGACGCC | TATCAAAATA | GACGTGATGG | CCCTGCGCCG | 60 |
| AACCGGCGAC | CGGCCAAAAG | GTGGTGGATG | GGTGATGCCA | GGGTTGGTAG | GTCGTAAATC | 120 |
| CCGGTCATCT | TGGTAGCCAC | TATAGGTGGG | TCTTAAGGGG | AGGCAACGGT | CCCTCTCGCG | 180 |
| CTTACGGAGA | GAAGGCGCAC | GGTCCACAGG | TGTTGGTCCT | ACCGGTGTGA | ATAAGGACTC | 240 |
| GGCGTTAGGC | TCGCCGTTAA | ACCGAGCCCG | TTAACCCCT | GGGCAAACGA | CGCCCACGTA | 300 |
| CGGTCTACGT | CGCCCTTCAA | TGTCTCTCTT | GACCAATAGG | CAATGCCGGC | GAGTTGACAA | 360 |
| GGACCAGTGG | GGGCCGGGTG | GGGGGGGAAG | GACCCCCTC | ACTGCCCTTC | CGGGGGTGC | 420 |
| GGGAAATGCA | TGGGGCCACC | CAGCTCCGCG | GCGGCCTACA | GCCGGGGTAG | CCCAAGAACC | 480 |
| TTCGGGTGAG | GGCGGGTGGC | ATTTTTCTTC | CTATACCGAT | CATGGCAGTC | CTCCTGCTCT | 540 |
| TCTTCGTGGT | GGAGGCCGGG | GCCATTTTGG | CCCCGGCCAC | CCATGCTTGC | AGTGCAAAGG | 600 |
| GGCAATACTT | CCTCACAAAC | TGTTGCGCCC | TG | | | 632 |

(2) INFORMATION FOR SEQ ID NO:78:

(i) SEQUENCE CHARACTERISTICS:
(A) LENGTH: 436 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:78:

| GGTGCAAGCC | CCAGAAACCG | ACGCCTATTT | AAACAGACGT | TATGAACCGG | CGCCGACCCG | 60 |
| GCGACCGGCC | AAAAGGTGGT | GGATGGGTGA | TGCCAGGGTT | GGTAGGTCGT | AAATCCCGGT | 120 |

| | | | | | |
|---|---|---|---|---|---|
|CATCTTGGTA|GCCACTATAG|GTGGGTCTTA|AGGGTTGGTC|AAGGTCCCTC|TAGCGCTTGT| 180
|GGCGAGAAAG|CGCACGGTCC|ACAGGTGTTG|GCCCTACCGG|TGTGAATAAG|GGCCCGACGT| 240
|CAGGCTCGTC|GTTAAACCGA|GCCCATTACC|CACCTGGGCA|AACAACGCCC|ACGTACGGTC| 300
|CACGTCGCCC|TACAATGTCT|CTCTTGACCA|ATAGGCTTTG|CCGGCGAGTT|GACAAGGACC| 360
|AGTGGGGGCT|GGGCGGCAGG|GGAAGGACCC|CTGTCGCTGC|CCTTCCCGGT|GGGGTGGGGA| 420
|ATGCATGGGG|CCACCC| | | | | 436

( 2 ) INFORMATION FOR SEQ ID NO:79:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:79:

| | | | | | |
|---|---|---|---|---|---|
|AGGGTTGGTA|GGTCGTAAAT|CCCGGTCACC|TTGGTAGCCA|CTATAGGTGG|GTCTTAAGAG| 60
|AAGGTTAAGA|TTCCTCTTGT|GCCTGCGGCG|AGACCGCGCA|CGGTCCACAG|GTGTTGGCCC| 120
|TACCGGTGGG|AATAAGGGCC|CGACGTCAGG|CTCGTCGTTA|AACCGAGCCC|GTCACCCACC| 180
|TGGGCAAACG|ACGCCCACGT|ATGGTCCACG|TCGCCCTTCA|ATGCCTCTCT|TGGCCAATAG| 240
|GTTTATCCGG|CGAGTTGACA|AGGACCAGTG|GGGGCCGGGG|GTTCGGGGAA|GGACCTCGTA| 300
|CCCTGCCCTT|CCCGGTGGAA|CGGGAAATGC|ATGGGCCAC|CCAGCTCCG| | 349

( 2 ) INFORMATION FOR SEQ ID NO:80:

( i ) SEQUENCE CHARACTERISTICS:
        ( A ) LENGTH: 355 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:80:

| | | | | | |
|---|---|---|---|---|---|
|AGGGTTGGTA|GGTCGTAAAT|CCCGGTCATC|TTGGTAGCCA|CTATAGGTGG|GTCTTAAGGG| 60
|GAGGTAAAGG|TCCCTCTTGC|GCTTATGGAG|GAACAGCGCA|CGGTCCACAG|GTGTTGGTCC| 120
|TACCGGTGTA|ATAAGGACCC|GGCGCTAGGC|ACGCCGTTAA|ACCGAGCCCG|TTACCCTCCT| 180
|GGGCAAACGA|CGCCCACGTA|CGGTCCACGT|CGCCCTTCAA|TGTCTCTCTT|GACCAATAGG| 240
|TTCTACCGGC|GAGTTGACAA|GGACCAGTGG|GGGCCGGGCG|GGAGGGGAA|GGACCCCAC| 300
|CGTCGCCCTT|CCCGGAGGGG|CGGGAAATGC|ATGGGCCAC|CCAGCTCCGG|CATGG| 355

( 2 ) INFORMATION FOR SEQ ID NO:81:

( i ) SEQUENCE CHARACTERISTICS:
        ( A ) LENGTH: 636 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:81:

| | | | | | |
|---|---|---|---|---|---|
|CACTGGGTGC|AAGCCCCAGA|AACCGACGCC|TATCTAAGTA|GACGCAATGA|CTCGGCGCCG| 60
|ACTCGGCGAC|CGGCCAAAAG|GTGGTGGATG|GGTGATGCCA|GGGTTGGTAG|GTCGTAAATC| 120
|CCGGTCATCT|TGGTAGCCAC|TATAGGTGGG|TCTTAAGAGA|AGGTTAAGAT|TCCTCTTGTG| 180

```
CCTGCGGCGA  GACCGCGCAC  GGTCCACAGG  TGTTGGCCCT  ACCGGTGTAA  TAAGGGCCCG     240

ACGTCAGGCT  CGTCGTTAAA  CCGAGCCCGT  CACCCACCTG  GGCGAACGAC  GCCCACGTAC     300

GGTCCACGTC  GCCCTTCAAT  GCCTCTCTTG  GCCAATAGGA  GATTCCTCCG  GCGAGTTGGC     360

AAGGACCAGT  GGGGCCGGG   GGTCACAGGG  AAGGACCCTG  GACCCTGCCC  ATCCCGGTGG     420

GCCGGGAAAT  GCATGGGGCC  ACCCAGCTCC  GCGGCGGCCT  GCAGCCGGGG  TAGCCCAAGA     480

ATCCTTCGGG  TGAGGGCGGG  TGGCATTTCT  CTTTCCTATA  CCATCATGGC  AGTCCTTCTG     540

CTCCTTCTCG  TGGTTGAGGC  CGGGGCCATT  CTGGCCCCGG  CCACCCACGC  TTGTAGAGCG     600

AATGGGCAAT  ATTTCCTCAC  AAACTGTTGC  GCCCTG                                 636
```

( 2 ) INFORMATION FOR SEQ ID NO:82:

( i ) SEQUENCE CHARACTERISTICS:
        ( A ) LENGTH: 633 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:82:

```
CACTGGGTGC  AAGCCCCAGA  AACCGACGCC  TATCTAAGTA  GACGCAATGA  CTCGGCGCCG      60

ACCCGGCGAC  CGGCCAAAAG  GTGGTGGATG  GGTGATGCCA  GGGTTGGTAG  GTCGTAAATC     120

CCGGTCATCT  TGGTAGCCAC  TATAGGTGGG  TCTTAAGGGA  AGGTTAAGAT  TCCTCTTGTG     180

CCTGTGGCGA  GACAGCGCAC  GGTCCACAGG  TGTTGGCCCT  ACCGGTGTGA  ATAAGGGCCC     240

GACGTCAGGC  TCGTCGTTAA  ACCGAGACCG  ACACCCACCT  GGGCAAACGA  CGCCCACGTA     300

CGGTCCACGT  CGCCCTTCAA  TGTCTCTCTT  GACCAATAGG  CTTTGCCGGC  GAGTTGACAA     360

GGACCAGTGG  GGGCCGGGGG  CTGGGAGAAG  GACTCCACG   CCCCGCCCTT  CCGGGGGGA      420

CGGGAAATGC  ATGGGGCCAC  CCAGCTCCGC  GGCGGCCTGC  AGCCGGGTA   GTCCAAGAGC     480

CTTCGGGTGA  GGACGGGTGG  CATTTCTTTT  TCTACACCGA  TCATGGCAGT  CCTTCTGCTC     540

TTCTTCGTGG  TTGAGGCCGG  GGCCATTCTG  GCCCCGGCCA  CCCACGCTTG  TCGAGCTGGT     600

GGGCAATATT  TCCTCACAAA  CTGTTGCGCC  CTG                                    633
```

( 2 ) INFORMATION FOR SEQ ID NO:83:

( i ) SEQUENCE CHARACTERISTICS:
        ( A ) LENGTH: 631 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:83:

```
CACTGGGTGC  AAGCCCCAGA  AACCGACGCC  TATCAAAATA  GACGTGATGG  CCCCGCGCCG      60

AACTGGCGAC  CGGCCAAAAG  GTGGTGGATG  GGTGATGACA  GGGTTGGTAG  GTCGTAAATC     120

CCGGTCATCC  TGGTAGCCAC  TATAGGTGGG  TCTTAAGGG   AGGCTACGGT  CCCTCTCGCG     180

CTTACGGAGA  GAAAGCGCAC  GGTTCACAGG  TGTTGGCCCT  ACCGGTGTAA  TAAGGGCCCG     240

GCGCTAGGCA  CGCCGTTAAA  CCGAGACCGT  TACCCTCCTG  GGCAAACGAC  GCCCACGTAC     300

GGCCCACGTC  GCCCTTCAAT  GTCTCTCTTG  ACCAATAGGC  AATGCCGGCG  AGTTGACAAG     360

GGCCAGTGGG  GGCCGGCGGA  CAGGGGAAGG  ACCCCTGTCG  CTGCCCTTCC  CGGAGGGACG     420

GGAAATGCAT  GGGGCCACCC  AGCTCCGCGG  CGGCCTACAG  CCGGGGTAGC  CCAAGAACCT     480
```

```
TCGGGTGAGG  GCGGGTGGCA  TTTCTTTTCC  TATACCAATC  ATGGCAGTCC  TTCTGCTCTT    540

ACTCGTTGTG  GAGGCCGGGG  CCATYCTGGC  CCCGGCCACC  CATGCTTGTA  GCGCTAAAGG    600

GCAATATTTC  CTCACAAACT  GTTGCGCCCT  G                                    631
```

(2) INFORMATION FOR SEQ ID NO:84:

(i) SEQUENCE CHARACTERISTICS:
        (A) LENGTH: 633 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:84:

```
CACTGGGTGY  RARCCCCAGA  AACCGACGCC  TATCTAAGTA  GACGCAATGA  CTCGGCGCCG     60

ACTCGGCGAC  CGGCCAAAAG  GTGGTGGATG  GGTGATGACA  GGGTTGGTAG  GTCGTAAATC    120

CCGGTCACCT  TGGTAGCCAC  TATAGGTGGG  TCTTAAGAGA  AGGTTAAGAT  TCCTCTTGTG    180

CCTGCGGCGA  GACCGCGCAC  GGTCCACAGG  TGCTGGCCTT  ACCGGTGCAA  ATAAAGGCCC    240

GACGTCAGGC  TCGTCGTTAA  ACCGAGCCCG  TTACCCACCT  GGGCAAACGA  CGCCCACGTA    300

CGGTCCACGT  CGCCCTTCAA  TGTCTCTCTT  GACCAATAGG  CTTAGCCGGC  GAGTTGACAA    360

GGACCAGTGG  GGGCCGGGGG  TTTGGGGAAG  GACCCCAAGC  CCTGCCCTTC  CCGGTGGGCC    420

GGGAAATGCA  TGGGGCCACC  CAGCTCCGCG  GCGGCCTGCA  GCCGGGGTAG  CGCAAGAATC    480

CTTCGGGTGA  GGGCGGGTGG  CATTTTTCTT  TTCTATACCA  TCATGGCAGT  CCTTCTGCTC    540

CTTCTCGTGG  TTGAGGCCGG  GGCCATCCTG  GCCCCGGCCA  CCCACGCGTG  TCGAGCGAAT    600

GGGCAATATT  TCCTCACAAA  CTGTTGCGCC  CTG                                  633
```

(2) INFORMATION FOR SEQ ID NO:85:

(i) SEQUENCE CHARACTERISTICS:
        (A) LENGTH: 634 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:85:

```
CACTGGGTGC  AAGCCCCAGA  AACCGACGCC  TATCTAAGTA  GACGCAATGA  CTCGGCGCCA     60

ACTCGGCGAC  CGGCCAAAAG  GTGGTGGATG  GGTGATGACA  GGGTTGGTAG  GTCGTAAATC    120

CCGGTCACCT  TGGTAGCCAC  TATAGGTGGG  TCTTAAGAGA  AGGTTAAGAT  TCCTCTTGTG    180

CCTGCGGCGA  GACCGCGCAC  GGTCCACAGG  TGTTGGCCCT  ACCGGTGTGA  ATAAGGGCCC    240

GACGTCAGGC  TCGTCGTTAA  ACCGAGCCCG  TCACCCACCT  GGGCAAACGT  CGCCCACGTA    300

CGGTCCACGT  CGCCCTTCAA  TGTCTCTCTT  GACCAATAGG  CTTAGCCGGC  GAGTTGACAA    360

GGACCAGTGG  GGGTCGGGGG  CTTGGGGAGG  GACCCCAAGT  CCTGCCCTTC  CCGGTGGGCC    420

GGGAAATGCA  TGGGGCCACC  CAGCTCCGCG  GCGGCCTGCA  GCCGGGGTAG  CCCAAGAATC    480

CTTCGGGTGA  GGGCGGGTGG  CATTTTCTCT  TTTCTATACC  ATCATGGCAG  TCCTTCTGCT    540

CCTTCTCGTG  GTCGAGGCCG  GGGCCATTCT  GGCCCCGGCC  ACCCACGCTT  GTCGAGCGAA    600

TGGGCAATAC  TTCCTCACAA  ACTGTTGCGC  CCTG                                 634
```

(2) INFORMATION FOR SEQ ID NO:86:

( i ) SEQUENCE CHARACTERISTICS:
   ( A ) LENGTH: 633 base pairs
   ( B ) TYPE: nucleic acid
   ( C ) STRANDEDNESS: double
   ( D ) TOPOLOGY: linear ( i i ) MOLECULE TYPE: DNA (genomic)

( x i ) SEQUENCE DESCRIPTION: SEQ ID NO:86:

| | | | | | | |
|---|---|---|---|---|---|---|
| CACTGGGTGC | AAGCCCCAGA | AACCGACGCC | TATCTAAGTA | GACGCGATGA | CTCGGCGCCG | 60 |
| ACTCGGCGAC | CGGCCAAAAG | GTGGTGGATG | GGTGATGACA | GGGTTGGTAG | GTCGTAAATC | 120 |
| CCGGTCACCT | TGGTAGCCAC | TATAGGTGGG | TCTTAAGAGA | AGGTTAAGAT | TCCTCTCGTG | 180 |
| CCTGCGGCGA | GACCGCGCAC | GGTCCGCAGG | TGTAGGCCCT | ACCGGTGTGA | ATAAGGGCCC | 240 |
| GACGTCAGGC | TCGTCGTTAA | ACCGAGCCCG | TCACCCACCT | GGGCTAACGA | CGCCCACGTA | 300 |
| CGGTCCACGT | CGCCCTTCAA | TGTCTCTCTT | GACCAATAGG | CTTAGCCGGC | GAGTTGACAA | 360 |
| GGACCAGTGG | GGGCCGGGGG | CTTGGAGAAG | GACTCCAAGT | CCTGCCCTTC | CCGGTGGGCC | 420 |
| GGGAAATGCA | TGGGCCACC | CAGCTCCGCG | GCGGCCTGCA | GCCGGGGTAG | CCCAAGAACC | 480 |
| CTTCGGGTGA | GGGCGGGTGG | CATTTCTTTT | TCCTATACCA | TCATGGCAGT | CCTTCTGCTC | 540 |
| TTTCTCGTGG | TTGAGGCCGG | GGCCATTTTG | GCCCCGGCCA | CCCACGCTTG | TCGAGCGAAT | 600 |
| GGGCAATATT | TCCTCACAAA | CTGTTGCGCC | CTG | | | 633 |

( 2 ) INFORMATION FOR SEQ ID NO:87:

( i ) SEQUENCE CHARACTERISTICS:
      ( A ) LENGTH: 20 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:87:

AGCAGAAGGA CTGCCATGAT                                         20

( 2 ) INFORMATION FOR SEQ ID NO:88:

( i ) SEQUENCE CHARACTERISTICS:
      ( A ) LENGTH: 26 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:88:

GGNRMKRTYC CYTTTTATGG GCATGG                                  26

( 2 ) INFORMATION FOR SEQ ID NO:89:

( i ) SEQUENCE CHARACTERISTICS:
      ( A ) LENGTH: 26 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:89:

ACNACNAGGT CNCCRTCYTT GATGAT                                  26